US007273613B1

(12) United States Patent
Harley et al.

(10) Patent No.: US 7,273,613 B1
(45) Date of Patent: Sep. 25, 2007

(54) DIAGNOSTICS AND THERAPY OF EPSTEIN-BARR VIRUS IN AUTOIMMUNE DISORDERS

(75) Inventors: John B. Harley, Oklahoma City, OK (US); Judith A. James, Edmond, OK (US); Kenneth M. Kaufman, Oklahoma City, OK (US)

(73) Assignees: The Board of Regents, The University of Oklahoma, Norman, OK (US); Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/500,904

(22) Filed: Feb. 9, 2000

(51) Int. Cl.
C07K 5/00 (2006.01)
A61K 39/00 (2006.01)
C12Q 1/70 (2006.01)

(52) U.S. Cl. ............... 424/186.1; 435/975; 435/7.1; 530/300; 530/324; 530/327; 530/326

(58) Field of Classification Search ............. 424/185.1, 424/320.1; 435/5, 6, 7.1; 536/23.5, 326, 536/350
See application file for complete search history.

(56) References Cited

U.S. PATENT DOCUMENTS

| | | |
|---|---|---|
| 4,554,101 A | 11/1985 | Hopp |
| 4,654,419 A | 3/1987 | Vaughan |
| 4,707,358 A | 11/1987 | Kieff |
| 4,784,942 A | 11/1988 | Harley |
| 4,865,970 A | 9/1989 | Brot et al. |
| 5,312,752 A | 5/1994 | Woltz et al. |
| 5,354,691 A | 10/1994 | Van Eden et al. |
| 5,637,454 A | 6/1997 | Harley |
| 5,679,774 A | 10/1997 | Wolf |
| 5,723,283 A | 3/1998 | Classen |
| 5,726,286 A | 3/1998 | Alderson |
| 5,874,531 A | 2/1999 | Strominger et al. |
| 5,965,353 A | 10/1999 | Middeldorp |

FOREIGN PATENT DOCUMENTS

| | | |
|---|---|---|
| EP | 0 113 431 B1 | 7/1984 |
| EP | 0 313 156 A1 | 4/1989 |
| WO | WO86/01210 | 2/1986 |
| WO | WO 86/01210 | 2/1986 |
| WO | WO88/09932 | 6/1988 |
| WO | WO 88/09932 | 6/1988 |
| WO | WO91/11718 | 8/1991 |
| WO | WO 91/11718 | 8/1991 |
| WO | WO 91/17171 | 11/1991 |
| WO | WO91/17171 | 11/1991 |
| WO | WO91/18920 | 12/1991 |
| WO | WO93/21223 | 10/1993 |
| WO | WO 94/02445 | 2/1994 |
| WO | WO94/02445 | 2/1994 |
| WO | WO94/02509 | 2/1994 |
| WO | WO 94/02509 | 2/1994 |
| WO | WO 94/06912 | 3/1994 |
| WO | WO94/06912 | 3/1994 |
| WO | WO 94/21669 | 9/1994 |
| WO | WO94/21669 | 9/1994 |
| WO | WO 96/37225 | 11/1996 |
| WO | WO96/37225 | 11/1996 |
| WO | WO98/30586 A | 7/1998 |

OTHER PUBLICATIONS

White et al. 1994. Medical Virology. Fourth edition. Acedemic Press. pp. 154-155 and 343-347.*
Carson. 1992. Genetic factors in the etiology and pathogenesis of autoimmunity. FASEB Journal. vol. 6. No. 10. Abstract only.*
Rhodes et al. 1985. Human immune responses to synthetic peptides from the epstein-barr nuclear antigen. The Journal of Immunology. vol. 134. No. 1, pp. 211-216.*
Petersen et al. 1990. Altered immune response to glysine-rich sequences of Epstein-Barr nuclear antigen-1 in patients with rheumatoid arthritis and systemic lupus erythematosus. Arthritis and Rheumatism. vol. 33. No. 7, pp. 993-1000.*
Marchini et al. Journal of Autoimmunity. 1994; 7: 179-191.*
Alexander, et al., "Anti-Ro/SS-A Antibodies in the Pathophysiology of Congenital Heart Block in Neonatal Lupus Syndrome, and Experimental Model," *Arth. And Rheum.* 35:176-189 (1992).
Arbuckle, et al., "Shared early autoantibody recognition events in the development of anti-Sm B/B' in human lupus," *Scand. J. Immunol.* 50(5):447-55 (1999).

(Continued)

*Primary Examiner*—Bruce R. Campell
*Assistant Examiner*—Bao Qun Li
(74) *Attorney, Agent, or Firm*—Fulbright & Jaworski, LLP

(57) ABSTRACT

Data consistent with autoimmune disease being caused by Epstein-Barr virus are shown. Based on this evidence, an effective vaccine would prevent the autoimmune disease in those vaccinated, modified or administered so that the vaccine is not itself capable of inducing autoimmune disease. In the case of anti-Sm, structures to be avoided in an Epstein-Barr virus-derived vaccine have been identified. Differences have been identified in the immune responses to Epstein-Barr infection between individuals who develop a specific autoimmune disease and those who do not. These differences are used to distinguish those who are at greater risk for developing specific autoimmune diseases from those who are a lesser risk. Assuming Epstein-Barr virus causes autoimmune disease and that Epstein-Barr virus remains latent in the patient for life, reactivation of the virus from the latent state is important in generating or maintaining the autoimmune response that culminates in autoimmune disease. Cells infected with latent virus may also encourage autoimmunity. Based on the understanding that reactivation or latency are important to produce or sustain autoimmunity, then therapies directed against Epstein-Barr virus will also be effective therapies for the autoimmune manifestations of disease for which Epstein-Barr virus is responsible.

2 Claims, 11 Drawing Sheets

OTHER PUBLICATIONS

Baraket, et al., "Mapping of epitopes on U1 snRNP polypeptide A with synthetic peptides and autoimmune sera," *Clin. Exp. Immunol.* 86:71-78 (1991).

Baraket, et al., "Recognition of Synthetic Peptides of Sm-D Autoanigen by Lupus Sera," *Clin. Exp. Immunol.* 81:256-262 (1990).

Ben-Chetrit, et al., "Isolation and Characterization of a cDNA Encoding the 60-kD Component of the Human SS-A/Ro Ribonucleoprotein Autoantigen," *J. Clin. Inv.* 83:1284-1292 (1989).

Blank, et al., "Induction of Experimental Anti-phospholipid Syndrome Associated with SLE Following Immunization with Human Monoclonal Pathogenic Anti-DNA Idiotype," *J. Autoimmunity* 5:495-509 (1992).

Blank, et al., "Induction of SLE-Like Disease in Naive Mice with a Monoclonal anti-DNA Antibody Derived from a Patient with Polymyositis carrying the 16/6 id," *J. Autoimmunity* 1:683-591 (1988).

Blank, et al., Induction of Systemic Lupus Erythematosus in Naive Mice with T-cell Lines Specific for Human Anti-DNA Antibody SA-1 (16/6 Id+) and for Mouse Tuberculosis Antibody TB/68 (16/6 id+) *Clin. Immunol. Immunopathol.* 60:471-483 (1991).

Blank, et al., "Sex Hormone Involvement in the Induction of Experimental Systemic Lupus Erythematosus by a Pathogenic anti-DNA Idiotype in Naive Mice," *J. Rheumatol.* 17:311-317 (1990).

Blank, et al., "The Effect of the Immunomodulator Agent AS101 on Interleukin-2 Production in Systemic Lupus Erythematosus (SLE) Induced in Mice by Pathogenic Anti-DNA Antibody," *Clin. Exp. Immunol.* 79:443-447 (1990).

Bray, et al., "Antibodies Against Epstein-Barr Nuclear Antigen (EBNA) in Multiple Sclerosis CSF, and Two Pentapeptide Sequence Identities Between EBNA and Myelin Basic Protein," *Arch. Neurol.* 42:1798-1804 (1992).

Bray, et al., "Epstein-Barr Virus Infection and Antibody Synthesis in Patients With Multiple Sclerosis," *Arch. Neurology* 40:406-408 (1983).

Buyon, "Neonatal Lupus Syndrome," *Curr. Opin. In Rheum.* 6:523-529 (1994).

Chambers, et al., "Genomic Structure and Amino Acid Sequence domains of the Human La Autoantigen," *J. Biol. Chem.* 263:18043-18051 (1988).

Chambers, et al., "Isolation and analysis of cDNA Clones Expressing Human Lupus La Antigen," *Proc. Natl. Acad. Sci. USA* 82:2115-2119 (1985).

Chan, et al., "Ribonucleoprotein SS-B/La belongs to a Protein Family with Consensus Sequences for RNA Binding," *Nucl. Acids Res.* 17:2233-2244 (1989).

Cohen, "The Self, the World and Autoimmunity—Autoimmunity—In Which the Immune System Recognizes and ATtaks the Self's Own Tissues—Is Not as Simple as it Seemed. Self-recognition Appears to be at the Heart of Health as Well as of Certain Diseases," *Scientific American* 258:52-60 (1988).

Craft, et al., "Murine and Drosophila B Proteins of SM snRNPS," *Mol. Biol. Rep.* 15:159 (1991).

Crone, et al., "Viral Transcription is Necessary and Sufficient for Vesicular Stomatis Virus to Inhibit Maturation of Small Nuclear Ribonucleoproteins," *Journal of Virology* 63(10):4172-4180 (1989).

Dalldorf, et al., "The Lymphomas of Brazilian Children," *J. Am. Med. Assn.* 208:1365-8 (1969).

Deacon, et al., "Detection of Epstein-Barr Virus Antigens and DNA in Major and Minor Salivary Glands Using Immunocytochemistry and Polymerase Chain Reaction: Possible Relationship with Sjogren's Syndrome," *J. Pathol.* 163:351-360 (1991).

Deacon, et al., "Frequency of EBV DNA Detection in Sjogren's Syndrome," *Am J. Med.* 92:453-454 (1992).

Depolo, et al., "Continuing Coevolution of Virus and Defective Interfering Particles and of Viral Genome Sequences During Undiluted Passages: Virus Mutants Exhibiting Nearly Complete Resistance to Formerly Dominant Defective Interfering Particles," *J. of Virology* 61:454-464 (1987).

Deutscher, et al., "Molecular Analysis of the 60-kDa Human Ro Ribonucleoprotein," *Proc. Natl. Acad. Sci. USA* 85:9479-83 (1988).

Dyrberg & Oldstone, "Peptides as Probes to Study Molecular Mimicry and Virus-Induced Autoimmunity," *Current Topics in Microbiology and Immunology* 130:25-37 (1986).

Elkon, et al., "Epitope Mapping of Recombinant HeLa SmB and B' Peptides Obtained by the Polymerase Chain Reaction," *J. Immun.* 145:636-643 (1990).

Esquivel, et al., "Induction of Autoimmunity in Good and Poor Responder Mice with Mouse Thyroglobulin and Lipopolysaccharide," *J. Exp. Med.* 145:1250-1263 (1977).

Evans & Niederman, "Epstein-Barr virus", in Viral Infections in Humans, 3rd ed. Evans, A.S. ed. pp. 265-292 (Flenum, New York City 1989).

Evans, "E.B. Virus Antibody in Systemic Lupus Erythematosus" *Lancet* 1:1023-4 (1971).

Evans, et al., "E.B.V. Antibodies in Systemic Lupus Erythematosus," *Lancet* 325-324 (1973).

Evans, et al., "Raised Antibody Titres to E.B. Virus in Systemic Lupus Erythematosus," *Lancet* 1:167-168 (1971).

Ferris & Donaldson, *Veterinary Microbiology* 18(3-4):243-258 (1988).

Finerty, et al., "Immunization of Cottontop Tamarins and Rabbits with a Candidate Vaccine Against the Epstein-Barr Virus Based on the Major Viral Envelope Glycoprotein gp340 and Alum," *Vaccine* 12:1180-1184 (1994).

Finerty, et al., "Protective Immunization Against Epstein-Barr Virus-Induced Disease in Cottontop Tamarins Using the Virus Envelope glycoprotein gp340 Produced from a Bovine Papillomavirus Expression Vector," *J. Gen. Virol.* 73:449-453 (1992).

Fox, "Sjogren's Syndrome," *Current Opin. Rheum.* 7:409-416 (1995).

Fox, et al., "Detection of Epstein-Barr Virus-Associated Antigens and DNA in Salivary Gland Biopsies from Patients with Sjogen's Syndrome," *J. Immunol.* 137:3162-3168 (1986).

Fox, et al., "Potential Role of Epstein-Barr Virus in Sjogren's Syndrome and Rheumatoid Arthritis," *J. Rheumatol.* 19:18-24 (1992).

Fricke, et al., "Induction of Experimental Systemic Lupus Erythematosus in Mice by Immunization with a Monoclonal Anti-La Autoantibody," *Intern. Immunol.* 2:225-230 (1990).

Fritz, et al., "Small Nuclear U-Ribonucleoproteins in *Xenopus laevis* Development," *J. Mol. Biol.* 178:273-285 (1984).

Gaither, et al., "Implications of Anti-Ro/Sjogren's Syndrome a Antigen Autoantibody in Normal Sera for Autoimmunity," *J. Clin. Invest.* 79:841-846 (1987).

Gaither, et al., "Affinity Purification and Immunoassay of Anti-Ro/SSA" *Peptides Biol. Fluids* 33:413-416 (1985).

Gallione, et al., "Nucleotide Sequences of the mRNA's Encoding the Vesicular Stomatitis Virus N and NS Proteins," *Virology* 39-529-535 (1981).

*Gautam, et al., "A viral peptide with limited homology to a self peptide can induce clinical signs of experimental autoimmune encephalomyelitis," *J. Immunol.* 161:60-64 (1998).

Gergely, et al., "E.B.V. Antibodies in Systemic Lupus Erythematosus," *Lancet* 1:325-326 (1973).

Hurd, et al., "Formation of Leukocyte Inclusions in Normal Polymorphonuclear Cells Incubated with Synovial Fluid," *Arthritis Rheum.* 13:724-733 (1970).

Inoue, et al., "Analysis of Antibody Titers to Epstein-Barr Virus Nuclear Antigens in Sera of Patients with Sjogren's Syndrome and with Rheumatoid Arthritis," *J. Infect. Dis.* 164:22-28 (1991).

Ishii, et al., "Cycloheximide-Induced Apoptosis in Burkitt Lymphoma (BJA-B) Cells with and Without Epstein-Barr Virus Infection," *Immunol. Cell Biol.* 73:463-468 (1995).

James & Harley, "Linear Epitope Mapping of a Sm B/B' Polypeptide," *J. Immunol.* 148:2074-2079 (1992).

James & Harley, "Peptide Autoantigenicity of the Small Nuclear Ribonucleoprotein C," *Clin. And Exp. Rheum.* 13:299-305 (1995).

*James & Harley, "A model of peptide-induced lupus autoimmune B cell epitope spreading is strain specific and is not H-2 restricted in mice," *J. Immunol.* 160(1):502-8 (1998).

*James, et al., "An increased prevalence of Epstein-Barr virus infection in young patients suggests a possible etiology for systemic lupus erythematosus," *J. Clin. Invest.* 100:3019-26 (1997).

*James, et al., "Lupus humoral autoimmunity after short peptide immunization," *Ann. N. Y. Acad. Sci.* 815:124-7 (1997).

James, et al., "Immunoglobulin Epitope Spreading and Autoimmune Disease After Peptide Immunization: Sm B/B'-derived PPPGMRPP and PPPGIRGP Induce Spliceosome Autoimmunity," *J. Exp. Med.* 181:453-461 (1995).

James, et al., "Basic Amino Acids Predominate in the Sequential Autoantigenic Determinants of the Small Nuclear 70K Ribonucleoprotein," *Scand. J. Immunol.* 39:557-566 (1994).

James, et al., "Inbred Mice Strains Differ in Their Capacity to Develop Spliceosomal Autoimmunity After Peptide Immunization," *Arthritis Rheum.* 38:S226 (1995).

James, et al., "Lupus Humoral Autoimmunity After Short Peptide Immunization[a]," *Arthritis Rheum.* 39:S216 (1996).

James, et al., "Sequential Autoantigenic Determinants of the Small Nuclear Ribonucleoprotein Sm D Shared by Human Lupus Autoantibodies and MRL *lpr/lpr* Antibodies," *Clin. Exp. Immunol.* 98:419-426 (1994).

Karameris, et al., "Detection of the Epstein Barr Viral Genome by an in situ Hybridization Method in Salivary Gland Biopsies from Patients with Secondary Sjorgren's Syndrome," *Clin. Exp. Rheum.* 10:327-332 (1992).

Kaufman, et al., "In Vivo Binding of Gram-Negative Bacterial Peptides to Hla-B27: A Possible Relationship to Anklosing spondylitis Pathogenesis," *Arthritis Rheum.* 39:S298 (1996).

Kieff & Liebowitz, Epstein-Barr virus and its replication. In Virology, 2nd ed. Fields et al., eds. pp. 1889-1921 (Raven Press, New York 1990).

Kitagawa, et al., "Detection of Antibodies to the Epstein-Barr Virus Nuclear Antigens in the Sera from Patients with Systemic Lupus Erythematosus," *Immunol. Lett.* 17:249-252 (1988).

Klippel, et al., "Epstein-Barr Virus Antibody and Lymphocyte Tubuloreticular Structures in Systemic Lupus Erythematosus," *Lancet*, 2:1057-1058 (1973).

Kurilla, et al., "The Leader RNA of Vesicular Stomatis Virus is Bound by a Cellular Protein Reactive with Anti-La Lupus Antibodies," *Cell* 34:837-845 (1983).

Kuzushima, et al., "Establishment of Anti-Epstein-Barr Virus (EBV) Cellular Immunity by Adoptive Transfer of Virus-Specific Cytotoxic T Lymphocytes from an HLA-matched Sibling to a Patient with Severe chronic Active EBV Infection," *Clin. Exp. Immunol.* 103:192-198 (1996).

Larsen, et al., "Epstein-Barr Nuclear Antigen and Viral Capsid Antigen Antibody Titers in Multiple Sclerosis," *Neurology* 35:435-438 (1985).

Lazarovits, et al., "Anti-B Cell Antibodies for the Treatment of Monoclonal Epstein-Barr Virus-Induced Lymphoproliferative Syndrome After Multivisceral Transplantation," *Clin. Invest. Med.* 17:621-625 (1994).

Lee, et al., "Cardiac Immunoglobulin Deposition in Congenital heart Block Associated with Maternal Anti-Ro Autoantibodies," *Am. J. of Med.* 83:793-796 (1987).

Lee, et al., "The Recognition of Human 60-kDa Ro Ribonucleoprotein Particle by Antibodies Associated with Cutaneous Lupus and Neonatal Lupus," *J. Investigative Dermatology* 107(1):225-228 (1996).

Leff, "Maverick Herpes Receptor Sparks Search for KS Drug," *Bio World Today* 8(17):1 (1997).

*Nicholson, "A T cell receptor antagonist peptide induces T cells that mediate bystander suppression and prevent autoimmune encephalomyelitis induced with multiple myelin antigens," *Proc. Natl. Acad. Sci. USA* 94:9279-9284 (1997).

Newell & Stevens, "E.B. Virus Antibody in Systemic Lupus Erythematosus," *Lancet* 1:652 (1971).

Newkrik, et al., "Detection of Cytomegalovirus, Epstein-Barr Virus and Herpes Virus-6 in Patients with Rheumatoid Arthritis With or Without Sjogren's Syndrome," *Br. J. Rheum.* 33:317-322 (1994).

Ohosone, et al., "Molecular Cloning of cDNA Encoding Sm Autoantigen: Derivation of a cDNA for a B Polypeptide of the U Series of Small Nuclear Ribonucleoprotein Particles," *Proc. Natl. Acad. Sci. USA* 86:4249-4253 (1989).

Palfi, et al, "Purification of the Major UsnRNPs from Broad Bean Nuclear Extracts and Characterization of their Protein Constiuents," *Nucleic Acids Res.* 17:1445-1458 (1989).

Petersen, et al, "Altered Immune Response to Glycine-Rich Sequences of Epstein-Barr Nuclear Antigen-1 in Patients with Rheumatoid Arthritis and Systemic Lupus Erythematosus," *Arthritis Rheum.* 33:993-1000 (1990).

Pettersson, et al., "The Structure of Mammalian Small Nuclear Ribonuceoproteins," *J. Biol. Chem.* 259:5907-5914 (1984).

Pflugfelder, et al., "Amplification of Epstein-Barr Virus Genomic Sequences in Blood Cells, Lacrimal Glands, and Tears from Primary Sjogren's Syndrome Patients," *Ophthalmology* 97:976-984 (1990).

Pflugfelder, et al., "Epstein-Barr Virus and the Lacrimal Gland Pathology of Sjogren's Syndrome," *Am. J. Pathol.* 143:49-64 (1993).

Phillips, et al., "Viruses and Systemic Lupus Erthematosus," *Lancet* 1:1449 (1973).

Query, et al., "A Common RNA Recognition Motif Identified within a Defined U1 RNA Binding of the 70K U1 snRNP Protein," *Cell* 57:89-101 (1989).

Ravirajan & Staines, "Involvement in Lupus Disease of Idiotypes Id.F-423 and Id.IV-228 Defined, Respectively, Upon Foetal and Adult MRL/Mp-Ipr/Ipr DNA-binding Monoclonal Autoantibodies" *Immunology* 74:342-347 (1991).

Reichlin, et al., "Autoantibodies to the URNP Particles: Relationship to Clinical Diagnosis and Nephritis," *Clin. Exp. Immunol.* 83:286-290 (1991).

Reichlin, et al., "Concentration of Autoantibodies to native 60-kd Ro/SS-A and Denatured 52-kd Ro/SS-A in Eluates from the Heart of a Child Who Died with Congenital Complete Heart Block," *Arth. And Rheum.* 37-1698-1703 (1994).

Renz, et al., "Expression of the Major Human Ribonucleoprotein (RNP) Autoantigens in *Escherichia coli* and their Use in an EIA for Screening Sera from Patients with Autoimmune Disease," *Clin. Chem.* 35:1861-1863(1989).

Reuter, et al., "Immunization of Mice with Purified U1 Small Nuclear Ribonucleoprotein (RNP) Induces a Pattern of Antibody Specificieites Characterstic of the Anti-Sm and Anti-RNP Autoimmune Resposne of Patients with Lupus Erythematosus, As Measured by Monoclonal Antibodies," *PNAS* 83:8689-8693 (1986).

Rhodes, et al., "Autoantibodies in Infectious Mononucleosis Have Specificity for the Clycine-Alanine Repeating Region of the Epstein-Barr Virus Nuclear Antigen," *J. Exp. Med.*, 165:1026-1040 (1987).

Rhodes, et al., "Human Immune Responses to Synthetic Peptides from the Epstein-Barr Nuclear Antigen," *J. Immunol.* 134:211-216 (1985).

Sillikens, et al., "cDNA Cloning of the Human U1 snRNA-Associated A Protein: Extensive Homology Between U1 and U2 snRNP-Specific Proteins," *EMBO Journal* 6:3841-3848 (1987).

Sillikens, et al., "Human U1 snRNP-specific C Protein: Complete cDNA and Protein Sequence and Identification of a Multigene Family in Mammals," *Nucleic Acids Res.* 16:8307-21 (1988).

Singh, et al., "Decreased Incidence of Viral Infections in Liver Transplant Recipients—Possible Effects of FK506?," *Digestive Dis. Sci.* 39:15-18 (1994).

Spritz, et al., "The Human U1-70K s.n. RNP Proein: cDNA Cloning, Chromosomal Localization, Expression, Alternative Splicing and RNA-binding," *Nucleic Acid Res.* 15:10373-91 (1987).

Sturgess, et al., "Characteristics and Epitope Mapping of a Cloned Human Autoantigen La," *J. Immun.* 3212-3218 (1988).

Sumaya, et al., "Increased Prevalence and Titer of Epstein-Barr Virus Antibodies in Patients with Multiple Sclerosis," *Ann. Neurol.* 17:371-377 (1985).

Suzuki, et al., "Viral Interleukin 10 (IL-10), the Human Herpes Virus 4 Cellular IL-10 Homologue, Induces Local Anergy to Allogeneic and Syngeneic Tumors," *J. Exp. Med.* 182:477-486 (1995).

Takeda, et al., "Antigenic Domains on the U1 Small Nuclear Ribonucleoprotein-associated 70kD Polypeptide; a comparison of regions selectively recognized by Human and Mouse Autoantibodies and by Monoclonal Antibodies," Chem. Abstracts 116(1): ab. No. 4803a (Jan. 6, 1992).

Tan, et al., "The 1982 Revised Criteria for the Classification of Systemic Lupus Erythematosus," *Arthritis Rheum.* 25:1271-1277 (1982).

Arbuckle, et al., "Shared early autoantibody recoginition events in the development of anti-Sm B/B' in human lupus," *Scand. J. Immunol.* 50(5):447-55 (1999).

Banerjee, et al., "Complete Nucleotide Sequence of the mRNA Coding for the N Protein of Vesicular Stomatitis Virus (New Jersey Serotype)," *Virology* 137:432-438 (1984).

Barakat, et al., "IgG Antibodies From Patients with Primary Sjogren's Syndrome and systemic Lupus Erythematosus Recognize Different Epitopes in 60-kD SSA/Ro Protein," *Clin. Exp. Immunol.* 89:38-45 (1992).

Barakat, et al., "Recognition of Synthetic Peptides of Sm-D Autoantigen by Lupus Sera," *Clin. Exp. Immunol.* 81:256-262 (1990).

Chambers, et al., "Isolation and anlaysis of cDNA Clones Expressing Human Lupus La Antigen," *Proc. Natl. Acad. Sci. USA* 82:2115-2119 (1985).

Cunningham, et al., "Human Monoclonal Antibodies Reactive with Antigens of the Group A Streptococcus and Human Heart," *Journal of Immunology* 141(8):2760-2766 (1988).

Dickey, "Human Autoantibody Producing Grafts in SCID Mice," presented to the Oklahoma Lups Association, Inc., Sep. 1, 1989.

Evans & Niederman, "Epstein-Barr virus". in Viral Infections in Humans, 3rd ed. Evans, A.S. ed. pp. 265-292 (Plenum, New York City 1989).

Evans & Rothfield, "E.B. Virus and Other Viral Antibodies in Systemic Lupus Erythematosus," *Lancet* 1:1127-1128 (1973).

Geysen, et al., "Strategies for Epitope Analysis Using Peptide Synthesis," *J. of Immunol. Meth.* 102:259-274 (1987).

Geysen, et al., "Use of Peptide Synthesis to Probe Viral Antigens for Epitopes to a Resolution of a Single Amino Acid," *Proc. Natl. Acad. Sci. USA* 81:3998-4002 (1984).

Grabowski, et al., "Drosphila AP3, a Presumptive DNA Repair Protein, is Homologous to Human Ribosomal Associated Protein PO," *Nucleic Acids Research* 19(15):4297 (1991).

Gu, et al., "First EBV Vaccine Trial in Humans Using Recombinant Vaccinia Virus Expressing the Major Membrane Antigen," *Dev. Biol. Stand.* 84:171-177 (1995).

Guldner, et al., "Epitope mapping with a recombinant human 68-kDa (U1) ribonucleoprotein antigen reveals heterogeneous autoantibody profiles in human autoimmune sera." *The Journal of Immunology* 141(2):469-475 (1988).

Gutierrez, et al., "Switching Viral Latency to Viral Lysis: A Novel Therapeutic Approach for Epstein-Barr Virus-Associated Neoplasia," *Cancer Res.* 56:969-972 (1996).

Haahr, et al., "A Putative New Retrovirus Associated with Multiple Sclerosis and the Possible Involvement of Epstein-Barr Virus in This Disease," *Ann. N. Y. Acad. Sci.* 724:148-156 (1996).

Hahn, "Suppression of Autoimmune Diseases with Anti-idiotypic Antibodies: Murine Lupus Nephritis as a Model" *Springer Seminars in Immunopathology*, 7(1):25-34 (1984).

Hardgrave, et al, "Antibodies to Vesicular Stomatitis Virus Proteins in Patients with Systemic Lupus Erythematosus and in Normal Subjects," *Arthritis and Rheumatism* 36(7):962-970 (1993).

Harley & Gaither, "Autoantibodies" *Rheum. Dis. Clin. N. Amer.* 14:43-56 (1992).

Harley & James, "Review Articles: Autoepitopes in Lupus," *J. Lab. Clin. Med.* 126(6):509-516 (1995).

Harley, et al., "Epstein-Barr virus infection may be an environmental risk factor for systemic lupus erythematosus in children and teenagers," *Arthritis Rheum.* 42(8):1782-3 (1999).

Harley, et al, "Gene Interaction at HLA-DQ Enhances Autoantibody Production in Primary Sjorgren's Syndrome," *Science* 232:1145-1147 (1986).

Harley, et al., "Anti-Ro (SS-A) and Anti-La (SS-8) in Patients with Sjogren's Syndrome," *Arthritis Rheum.* 29:196-206 (1986).

Herbert, et al., Dictionary of Immunology 3rd Ed. Blackwell Scientific Publications Oxford UK p. 14 (1985).

Heslop, et al., "Long-Term Restoration of Immunity Against Epstein-Barr Virus Infection by Adoptive Transfer of Gene-Modified Virus-Specific T Lymphocytes," *Nature Med.* 2:551-555 (1996).

Hinterberger, "Isolation of Small Nuclear Ribonucleoproteins Containing U1, U2, U4, U5, and U6 RNAs," *J. Biol. Chem.* 258:2604-2613 (1983).

Hollinger, et al., "Seroepidemiologic Studies in Systemic Lupus Erythematosus," *Bact. Proc.* 131:174 (1970).

Horsfall, et al., "Ro and La Antigens and Maternal Anti-La Idiotype on the Surface of Myocardial Fibers in Congenital heart Block," *J. of Autoimmun.* 4:165-176 (1991).

Huang, et al., "Human Anti-Ro Autoantibodies Bind Peptides Accessible to the Surface of the Native Ro Autoantigen," *Scand. J. Immunol.* 41:220-228 (1995).

Huang, et al., "Immunization with Vesicular Stomatitis Virus Nucleocapsid Protein induces Autoantibodies to the 60-kD Ro Ribonucleoprotein Particle," *J. Invest. Med.* 43:151-158 (1995).

James & Harley, "Human Lupus Anti-Spliceosome A Protein Autoantibodies Bind Contiguous Surface Structures and Segregate into Two Sequential Epitope Binding Patterns," *J. Immunol.* 4018-4026 (1994).

James & Harley, "Sequential Fine Specificity of the Small Nuclear Ribonuclear Protein C," *Clinical Res.* 41(2):PA393 (1993).

James & Harley, "A model of peptide-induced lupus autoimmune B cell eptiope spreading is strain specific and is not H-2 restricted in mice," *J. Immunol.* 160(1):502-8 (1998).

James, et al., "Basic Amino Acid Predominate in the Sequential Autoantigenic Determinants of the Small Nuclear 70K Ribonucleoprotein," *Scand. J. Immunol.* 39:557-566 (1994).

Kalush, et al., "Neonatal Lupus Erythematosus with Cadian Involvement in Offspring of Mothers with Experimental Systemic Lupus Erythematosus," *J. of Clin. Immunol.* 14:314-321 (1994).

Kuzushima, et al., "Establishment of Anti-Eptein-Barr Virus (EBV) Cellular Immunity by Adoptive Transfer of Virus-Specific Cytotoxic T Lymphocytes from an HLA-matched Sibling to a Patient with Severe chronic Active EBV Infection," *Clin. Exp. Immunol.* 103:192-198 (1996).

Lehman, et al., "Spreading of T-Cell Autoimmunity to Cryptic Determinants of an Autoantigen," *Nature* 356:155-157 (1992).

Lerner & Steitz, "Antibodies to Small Nuclear PNAs Complexed with Proteins are Produced by Patients with Systemic Lupus Erythematosus," *Proc. Natl. Acad. Sci. USA* 76:5495-5499 (1979).

Lerner, et al., "Are snRNPs Involved in Splicing?" *Nature* 283:220-224 (1980).

Levitskaya, "Inhibition of Antigen Processing by the Internal Repeat Region of the Epstein-Barr Virus Nuclear Antigen-1," *Nature* 375:685-688 (1995).

Maddison, et al., "Quantitation of Precipitating Antibodies to Certain SolubleNuclear Antigens in SLE," *Arthritis Rheum.* 20:819-824 (1977).

Maitland, "Frequency of EBV-DNA Detection in Sjogren's Syndrome," *Am. J. Med.* 96:97 (1994).

Manfredi, et al., "Molecular Anatomy of an Autoantigen: T and B Eptiopes on the Nicotinic Acetylcholine Receptor in Myasthenia Gravis," *J. Lab. Clin. Med.* 120:13-21 (1992).

Mariette, et al., "Detection of Epstein-Barr Virus DNA by in Situ Hybridization and Polymerase Chain Reaction in Patients with Sjogren's Syndrome," *Am. J. Med.*, 90:286-294 (1991).

Matter, et al., "Molecular Characterization of Ribonucleoprotein Antigens Bound by Antinuclear Antibodies," *Arthritis Rheum.* 25:1278-1283 (1982).

Mattioli, et al. "Physical Association of Two Nuclear Antigens and Mutual Occurence of Their Antibodies: The relationship of the SM and RNA protein (MO) Systems in SLE Sera," *J. Immunol.* 110:1318-1324 (1973).

McAllister, et al., "cDNA Sequence of the rat U snRNP-associated Protein N: Description of a Potential Sm Eptiope," *EMBO J.* 8:1177-1181 (1989).

Mendlovic, et al., "Induction of an SLE-Like Disease in Mice by a Common Anti-DNA Idiotype," *Proc. Natl. Acad. Sci. USA* 85:2260-2264 (1988).

Mendlovic, et al., "The Genetic Regulation of the Induction of Experimental SLE," *Immunology* 69:228-236 (1990).

Mendlovic, et al., "The Role of Anti-Idiotypic Antibodies in the Induction of Experimental Systemic Lupus Erythematosus in Mice," *Eur. J. Immunol.* 19:729-732 (1989).

Miller, et al., "The Role of an Autoantigen, Histidyl-tRNA Synthetase, in the Induction and Maintenance of Autoimmunity," *Proc. Natl. Acad. Sci. USA* 87:9933-9937 (1990).

Miyashita, et al., "A Novel Form of Epstein-Barr Virus Latency in Normal B Cells In Vivo," *Cell*, 80:593-601 (1995).

Morgan, "Epstein-Barr Virus Vaccines," *Vaccine* 10:563-571 (1992).

Morgan, et al., "Validation of a First-Generation Epstein-Barr Virus Vaccine Preparation Suitable for Human Use," *J. Med. Virol.* 29:74-78 (1989).

Morland, et al., "Anti-idiotype and Immunosuppressant Treatment of Murine Lupus," *Clin. Exp. Immunol.* 83(1):126-132 (1991).

Morshed, et al., "Increased Expression of Epstein-Barr Virus in Primary Biliary Cirrhosis Patients," *Gastroenterol. Jpn.* 27(6):751-758 (1992).

Mosier, et al., "Transfer of a functional human immune system to mice with severe combined immunodeficiency," *Nature* 335:256-259 (1988).

Munves, et al., "Antibodies to Sm and RNP," *Arthritis Rheum.* 26:848-853 (1983).

Newkirk, et al., "Detection of Cytomegalovirus, Epstein-Barr Virus and Herpes Virus-6 in Patients with Rheumatoid Arthritis With or Without Sjogren's Syndrome," *Br. J. Rhuem.* 33:317-322 (1994).

Pflugfelder, et al., "Epstien-Barr Virus and the Lacrimal Gland Pathology of Sjogren's Syndrome," *Am. J. Pathol.* 143:49-64 (1993).

Phillips & Christian, "Myxovirus Antibody Increases in Human Connective Tissue Disease," *Science* 168:982-4 (1970).

Phillips, et al., "Viruses and Systemic Lupus Erythematosus," *Lancet* 1:1449 (1973).

Qualtiere & Pearson, "Radioimmune Precipitation Study Comparing the Epstein-Barr Virus Membrane Antigens Expressed on P3HR-1 Virus-Superinfected Raji Cells to those Expressed on Cells in a B-95 Virus-Transformed Produced Culture Activated with Tumor-Promoting Agent (TPA)," *Virology* 102:360-369 (1980).

Rokeach, et al., "Primary Structure of a Human Small Nuclear Ribonucleoprotein Polypeptide as Deduced by cDNA Analysis," *J. Biol. Chem.*, 264:5024-30 (1989).

Rokeach, et al., "Molecular Cloning of a cDNA Encoding the Human Sm-D Autoantigen," *Proc. Natl. Acad. Sci. USA* 85:4832-36 (1988).

Rose, et al., "Genetic Regulation in Autoimmune Thyroiditis," Talal N. ed. Autoimmunology Genetic Immunologic Virologic, and Clinical Aspects. New York: Academic Press, 63-87 (1977).

Rose, et al., "Studies on Experimental Thyroiditis," *Ann. NY Acad. Sci.* 124:201-209 (1965).

Rose, et al., "T-Cell Regulation in Autoimmune Thyroiditis," *Immunol. Reviews* 55:229-314 (1981).

Sabbatini, et al., "Autoantibodies from Patients with Systemic Lupus Erythematosus Bind a Shared Sequence of AmD and Epstein-Barr Virus-Encoded Nuclear Antigen EBNA I," *Eur. J. Immunol.* 23:1146-1152 (1993).

Saito, et al., "Detection of Epstein-Barr Virus DNA by Polymerase Chain Reaction in Blood and Tissue Biopsies from Patients with Sjogren's Syndrome," *J. Exp. Med.*, 169:2191-2198 (1989).

Sasaki, et al., "In Vitro Manipulation of Human Anti-DNA Antibody Production by Anti-idiotypic Antibodies Conjugated with Neocarzinostatin," *The Journal of Immunology* 142(4):1165-1165 (1989).

Schaack, "Molecular Mimicry in HLA-B-27-Related Arthritis," *Annals of Internal Medicine* 111(7):581-591 (1989).

Schmauss, et al., "A Comparison of snRNP-Associated Sm-Autoantigens: Human N, Rat N and Human B/B (abstract)," *Nuc. Acid Res.* 17:1733-43 (1989).

Scofield, "HLA-B27 Binding of Peptide From Its Own Sequence and Similar Peptides From Bacteria: Implications For Spondyloarthropathies," *Lancet*, 345:1542-1544 (1995).

Scofield, "A Common Autoepitope Near the carboxyl Terminus of the 60-kD Ro Ribonucleoprotein: Sequence Similarity with a Viral Protein," Journal of Clinical Immunology 11(6):378-388 (1991).

Scofield, "Autoimmune Thyroid Disease in Systemic Lupus Erythematosus and Sjogren's Syndrome," *Clin. Exp. Rheum.* 14:321-330 (1996).

Scofield, et al., "Immunization with Short Peptides from the Sequence of the Systemic Lupus Erythematosus-Associated 60-kDa Ro Autoantigen Results in Anti-Ro Ribonucleoprotein Autoimmunity," *J. Immunology* 4059-4066 (1996).

Scofield, et al., "Autoantigenicity of Ro/SSA Antigen is Related to a Nucleocapsid Protein of Vesicular Stomatitis Virus," *Proc. Natl. Acad. Sci. USA*, 88:3343-3347 (1991).

Scofield, et al., "Development of the Anti-Ro Autoantibody Response in a Patient with Systemic Lupus Erythematosus," *Arthritis & Rheumatism* 39(10):1664-1688 (1996).

Scofield, et al., "The Autoantigenicity of Human 60kD Ro/SSA is Related to Hormologies Between Ro/SSA and the Nucleocapsid Protein of Vesicular Stomatis Virus," *Clinical Research* 38(2):316A, (1990).

Sculley, et al., "Reactions of Sera from Patients with Rheumatoid Arthritis, Systemic Lupus Erythematosus and Infectious Mononucleosis to Epstein-Barr Virus-Induced Polypeptides," *J. Gen. Virol.* 67:2253-2258 (1986).

Sharpe, et al., "Isolation of cDNA Clones Encoding the Human Sm B/B' Auto-Immune Antigen and Specifically Reaching with Human Anti-Sm Auto-," *FEBS Lett.* 250:585-590 (1989).

Shoenfeld, et al. "Modulation of experimental SLE induced in naïve mice by a pathogenic anti-DNA idiotype (16/6 Id.)," Proceedings of the Second International Conference on Systemic Lupus Erythematosus Tokyo, Japan Professional Postgraduate Services 83 (1989).

Shoenfeld, et al., "Pathogenic idiotypes of autoantibodies in autoimmunity: lessons from new experimental models of SLE," *FASEB J.* 4:2646-2651 (1990).

Tan, et al., "Characteristics of a Soluble Nuclear Antigen Precipitating with Sera of Patients with Systemic Lupus Erthematosus," *J. Immunol.* 96:464-471 (1966).

Tateishi, et al., "Spontaneous Production of Epstein-Barr Virus by B Lymphoblastoid Cell Lines Obtained from Patients with Sjogren's Sydnrome," *Arthritis Rheum.* 36:827-835 (1993).

*The Medical Letter on Drugs and Therapeutics* 37(951):55-57 (Jun. 23, 1995).

Theissen, et al., "Cloning of the Human cDNA for the U1 RNA-associated 70K Protein," *EMBO J.* 5:3209-17 (1986).

Tigbe, Production of Human Rheumatoid Factors (RF) by SCID Mice Transplanted with Synovial Membrane Lymphocytes, presented at the Arthritis Foundation Fellows Conference, Amelia Island, Plantation, Florida, Dec. 8-10, 1989.

Tincani, et al., "Induction of Experimental SLE in Naive Mice by Immunization with Human Polyclonal anti-DNA Antibody Carrying the 16/6 Idiotypic," *Clinical and Exp. Rheum.* 11:129-134 (1993).

Toda, et al., "Sjogren's syndrome (SS) and Epstein-Barr virus (EBV) reactivation," In *Lacrimal Gland, Tear Film, and Dry Eye Syndrome.* (D.A. Sullivan, ed.) pp. 647-650 (Plenum Press, New York 1994).

Tsai, et al., "Detection of Epstein-Barr Virus and Cytomegalovirus Genome in White Blood Cells from Patients with Juvenile Rheumatoid Arthritis and Childhood Systemic Lupus Erythematosus," *Int. Arch. Allergy Immunol.* 106:235-240 (1995).

Tsuzuka, et al., "Lupus Autoantibodies to Double-stranded DNA Cross-react with Ribosomal Protein $S1^1,^2$" *J. Immunol.* 156:1668-1675 (1996).

Tzartos, et al., "The Main Immunogenic region of the Acetylcholine Receptor. Structure and Role in Myasthenia Gravis," *Autoimmunity* 8:259-270 (1991).

Van Dam, et al., "Cloned Human snRNP Proteins B and B' Differ Only in Their Carboxy-Terminal Part," *EMBO J.* 8(12):3853-3860 (1989).

Vandenbark, et al., "Effects of vaccination with T cell receptor peptides: Epitope switching to a possible disease-protective determinant of myelin basic protein that is cross-reactive with a TCR BV peptide," *Immunology and Cell Biology* 76:83-90 (1998).

Van Venrooij, et al., "B Cell Epitopes on Nuclear Autoantigens," *Arthritis and Rheumatism* 37(5):608-616 (1994).

Venables, et al., "Persistence of Epstein-Barr Virus in Salivary Gland Biopsies from Healthy Individuals and Patients with Sjorgren's Syndrome," *Clin. Exp. Immunol.*, 75:359-364 (1989).

Venables, et al., "The Response to Epstein-Barr Virus Infection in Sjorgren's Syndrome," *J. Autoimmunity* 2:439-448 (1989).

Virji & Heckels, "Location of a Blocking Epitope on Outer-membrane Protein III of Neisseria Gonorrhoeae by Synthetic Peptide Analysis," *J. of Gen. Microbiol.* 135:1895-1899 (1989).

Voller & Bidwell, "Enzyme-Linked Immunosorbent Assay," Manual of Clinical Laboratory Immunology (Chapter 17) (1986).

Wagstaff, et al., "Aciclovir—A Reappraisal of its Antiviral Activity, Pharmacokinetic Properties and Therapeutic Efficacy," *Drugs* 47:153-205 (1994).

Waite, et al., "Anti-Jo-1 antibodies are Directed at an Evolutionarily-conserved Conformational Site on Human Histidyl-tRNA Synthetase," *Mol. Cell Biol. Autoantibodies Autoimm.* 100-101 (1989).

Waltuck & Buyon, "Autoantibody-associated Congenital Heart Block: Outcome in Mothers and Children," *Ann. Intern. Med.* 120:544-551 (1994).

Warner & Carp, "Multiple Sclerosis Etiology—an Epstein-Barr Virus Hypothesis," *Med. Hypotheses* 25:93-97 (1988).

Watson, et al., "Certain Properties Make Substances Antigenic," in *Molecular Biology of the Gene*, Fourth Edition, p. 836, paragraph 3, (The Benjamin/Cummings Publishing Company, Menlo Park, 1987).

Whittingham, et al., "Epstein-Barr Virus as an Etiological Agent in Primary Sjogren's Syndrome," *Med. Hypothesis*, 22:373-386 (1987).

Williams, et al., "A Repeated Proline-rich Sequence in Sm B/B' and N is a Dominant Epitope Recognized by Human and Murine Autoantibodies," *J. Autoimmunity* 3:715-725 (1990).

Wilson, et al., "Association of Lymphomatoid Granulomatosis With Epstein-Barr Viral Infection of B Lymphocytes and Response to Interferon-α2b," *Blood*, 87:4531-4537 (1996).

Winfield, et al., "Serologic Studies in patients with Systemic Lupus Erythematosus and Central Nervous System Dysfunction," *Arthritis Rheum.* 21:289-294 (1978).

Witebsky, et al., "Chronic Thyroditis and Autoimmunization," *J. Am. Med. Assoc.* 164:1439-1447 (1957).

Xie & Snyder, "Two Short Autoepitopes on the Nuclear Dot Antigen Are Similar to Epitopes Encoded by the Epstein-Barr Virus," *Proc. Natl. Acad. Sci.* 92:1639-1643 (1995).

Yamamoto, et al., "Isolation and Characterization of a Complementary DNA Expressing Human U1 Small Nuclear Ribonucleoprotein C Polypeptide," *J. Immun.* 140:311-317 (1988).

Yokochi, et al., "Hight Titer of Antibody to the Epstein-Barr Virus Membrane Antigen in Sera from Patients with Rheumatoid Arthritis and Systemic Lupus Erythematosus," *J. Rheumatol.* 16:1029-1032 (1989).

Zeller, et al., "Nucleocytoplasmic Distribution of snRNPs and Stockpiled snRNA-Binding Proteins During Oogenesis and Early Development in *Xenopus laevis,*" *Cell* 32:425-434 (1983).

* cited by examiner

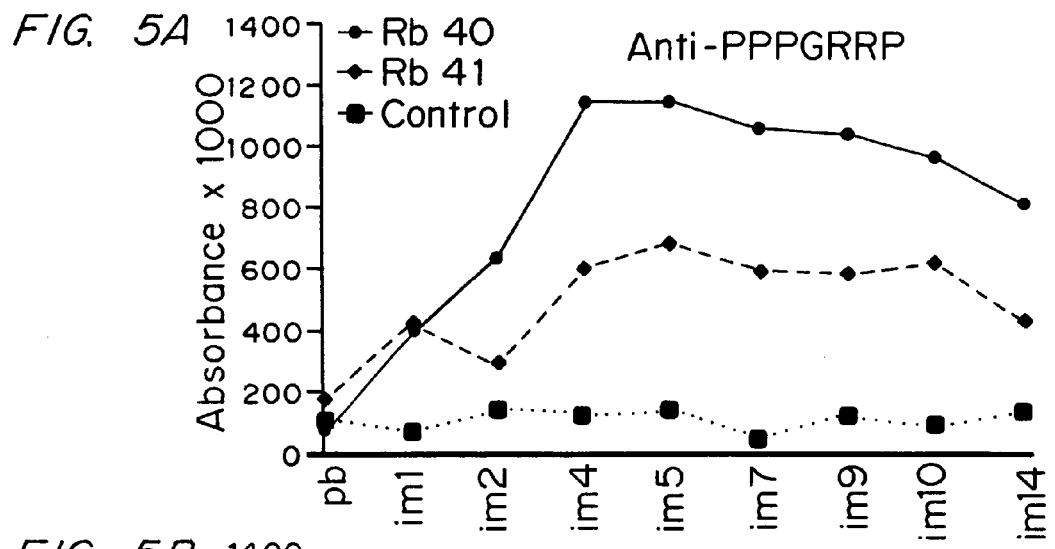
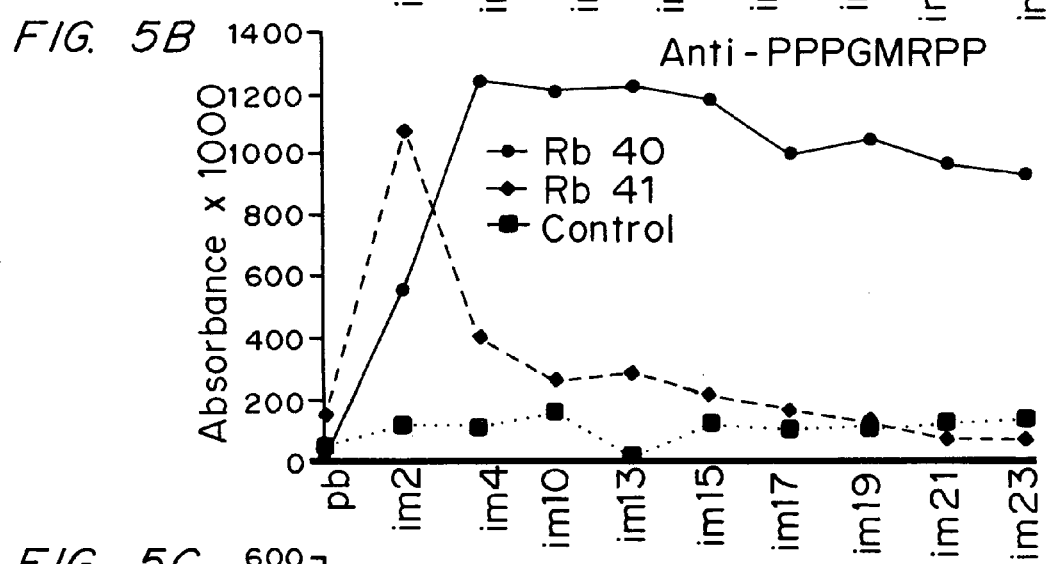
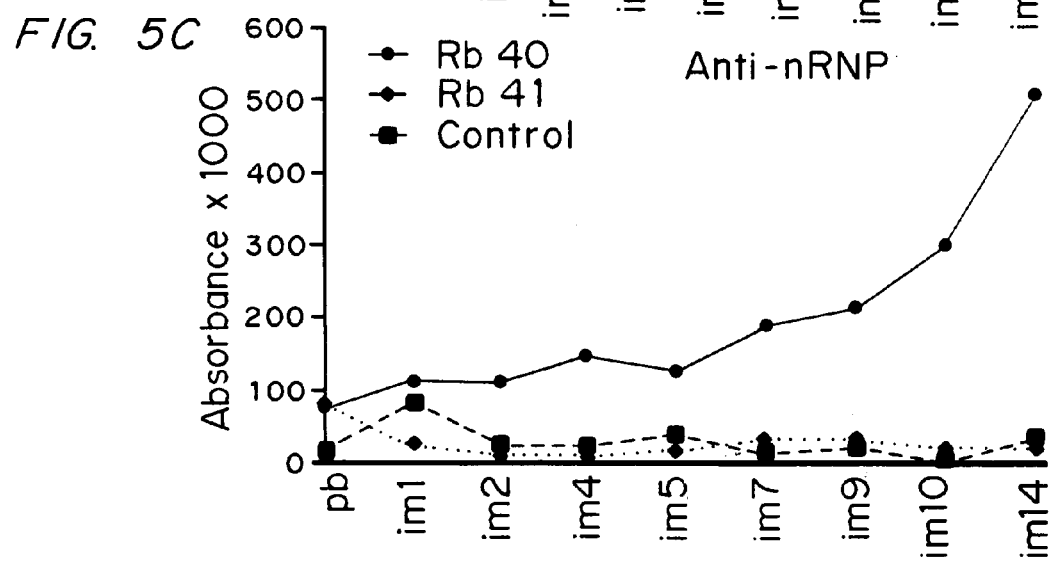

DIAGNOSTICS AND THERAPY OF EPSTEIN-BARR VIRUS IN AUTOIMMUNE DISORDERS

U.S. GOVERNMENT RIGHTS

The U.S. Federal Government has rights in this invention by virtue of Grant NO. RO1 AR42460 to John B. Harley and KO8 AR01981 to Judith A. James from the National Institutes of Health.

This application claims priority to U.S. Ser. No. 08/781,296 filed Jan. 13, 1997 entitled "Diagnostics and Therapy of Epstein-Barr Virus in Autoimmune Disorders" by John B. Harley and Judith A. James.

BACKGROUND OF THE INVENTION

This is in the area of the prevention, diagnosis, and treatment of autoimmune diseases having Epstein-Barr virus as an etiological agent.

Epstein-Barr virus infects B cells and induces a large number of different autoantibodies in the early phase of infection. The B cell proliferation and autoantibody production is eventually brought under control in nearly everyone by virus specific T cells. Thereafter, the virus remains latent, surviving in the host for the remainder of the natural life. Once the host is infected the virus continues to "reactivate" at a low level. Evidence for this reactivation is the shedding of virus in the oral cavity, infection through exchange of oral secretions, the spontaneous in vitro outgrowth of transformed B cells, and the spontaneous production of Epstein-Barr virus in vitro. The continuous presence of virus presents a significant challenge to the immune system and requires that the immune mechanisms sustain viral suppression over the many decades of remaining life. If Epstein-Barr virus causes autoimmune disease, then this feature, the sustained presence of a low level of virus in the host continuously emerging from latency, is likely to be important in diseases that appear long after the original infection by Epstein-Barr virus.

Epstein-Barr virus is a herpes virus and is also called Human Herpes Virus 4. This virus is from the genus Lymphocryptovirus and subfamily gammaherpesvirinae. There are several very good reviews of the biology and structure of Epstein-Barr virus. The reader is referred to classic reviews (Kieff, E. and Liebowitz, D.: Epstein-Barr virus and its replication. In Virology, 2nd ed. Fields et al., eds. pp 1889-1921 (Raven Press, New York 1990); Miller, G.: Epstein-Barr virus. ibid. pp. 1921-1958; Evans, A. S. and Niederman, J. C.: Epstein-Barr virus. In Viral Infections in Humans, 3rd ed. Evans, A. S. ed. pp 265-292 (Plenum, New York City 1989)). Like the other herpes viruses, this is a DNA virus and has a strong propensity for latency. Once latent this virus emerges from latency at a low level throughout life. Epstein-Barr virus induces lymphoma in some non-human primates. In man Epstein-Barr virus appears to be responsible for at least infectious mononucleosis, Burkitt's lymphoma and nasopharyngeal carcinoma.

Epstein-Barr virus infects the epithelium of the upper airway, B cells and a few T cells. On B cells the viral receptor is the Complement Receptor, Type 2, also known as the CR2 receptor. Infected B cells are able to present antigen, though the virus has recently been found to produce inhibitors of antigen processing (Levitskaya, J. Nature 375: 685-688 (1995)), and to synthesize a molecule similar to IL-10 which has profound local effects (Suzuki, T. et al J. Exp. Med. 182:477-486 (1995)). Depending upon what genes are expressed, latently infected B cells may not respond to stimuli in the usual way and may not provide the signals, either qualitatively or quantitatively, that would otherwise be provided. Such aberrant influences upon the normal immune response may provide the basis for subsequent autoimmune disease in some people.

Epstein-Barr virus has been known for more than three decades. For the specific example of an autoimmune disease used herein to illustrate the principles of the invention, many others have considered a relationship between systemic lupus erythematosus and Epstein-Barr virus. The size of the separate literatures concerning lupus, on the one hand, and Epstein-Barr virus on the other, are too vast to comprehensively review here. Nevertheless, over 25 years ago antibody titers were noted to be elevated against a number of viruses including rubella, measles, and parainfluenza 1 (Hollinger, F. B. et al. Bact. Proc. 131:174 (1970); Phillips, P. E. and Christian, C. L. Science 168:982-4 (1970); Hurd, E. R. et al. Arthritis Rheum. 13:724-33 (1970)). Dalldorf and colleagues reported an evaluation of the titers of antibody against Epstein-Barr virus in lupus patients; their data show differences between lupus patients and some of the control groups. These authors were not studying lupus; they performed these studies to better understand lymphoma. (Dalldorf, G. et al. J. Am. Med. Assn. 208:1365-8 (1969)).

Evans and colleagues were the first to claim to find elevated titers of anti-Epstein-Barr antibodies relative to controls (Evans, A. S., et al. Lancet 1:167-168 (1970)). This paper generated a number of responses, all of which encouraged caution in interpreting these results or address the potential artifacts which could confuse the interpretation (Newell, G. R. and Stevens, D. A. Lancet 1:652 (1971); Evans, A. S. Lancet 1:1023-4 (1971); Gergely, L. et al. Lancet 1:325-326 (1973); Evans, A. S. and Rothfield, N. F. Lancet 1:1127-1128 (1973); Phillips, P. E. et al. Lancet 1:1449 (1973)). Much of the confusion in interpreting these early serologic studies of lupus arises from the use of immunofluorescence assays for the detection of anti-Epstein-Barr virus seroconversion. This investigative activity culminated in a remarkable study in which many participants of the controversy combined their resources to develop data they interpreted to show, "the combined approach used in this study fails to provide supportive evidence that E.B. virus is a causative agent in the connective-tissue diseases" (Klippel, J. H. et al. Lancet 2:1057-1058 (1973)). They found no difference in the titer of antibodies against Epstein-Barr virus in lupus compared to controls.

A Japanese group found a high frequency of antibodies against Epstein-Barr virus Nuclear Antigens 2 and 3 in lupus patient sera, compared to normal controls (Kitagawa, H., Et al. Immunol. Lett. 17:249-252 (1988)). Another Japanese group found higher levels of antibody directed against a membrane antigen from Epstein-Barr virus in lupus (and rheumatoid arthritis) sera than in controls (Yokochi, T. et al. J. Rheumatol. 16:1029-1032 (1989)). Similarly, an Australian group found a modest increase in antibodies against early antigens (Sculley, D. G., et al. J. Gen. Virol. 67:2253-2258 (1986)).

An Italian group has shown that the affinity purified antibodies from the 95-119 region of Sm D from lupus patients bind the Epstein-Barr virus Nuclear Antigen-1 between amino acids 35 and 58 (Sabbatini, A., et al. Eur. J. Immunol. 23:1146-1152 (1993)).

A more recent contribution to this question uses both molecular methods to detect Epstein-Barr DNA and serologic methods to detect antibodies (Tsai, Y. et al. Int. Arch.

*Allergy Immunol.* 106:235-240 (1995)). This study also shows no significant differences between lupus patients and controls.

Other diseases, including both rheumatoid arthritis and Sjogren's syndrome, have been explored for a possible relationship to Epstein-Barr virus. Robert Fox and colleagues presented their conception of this area in 1992 Fox et al. H. *J. Rheumatol.* 19:18-24 (1992). The evidence which they conclude supports a role for Epstein-Barr virus in rheumatoid arthritis includes: similarity between synovial and viral antigens, higher levels of antibodies against the Epstein-Barr virus Nuclear Antigens 1 and 3, and the lower ability of lymphocytes to prevent the outgrowth of autologous, Epstein-Barr virus infected lymphocytes (Fox, R. I. *Current Opin. Rheum.* 7:409-416 (1995)). Others have found a small increase in the frequency of latency for Epstein-Barr virus in rheumatoid arthritis, but a much larger effect for Human Herpes virus-6 (Newkirk, M. M. et al. *Br. J. Rhuem.* 33:317-322 (1994)).

In Sjogren's syndrome Fox and colleagues note the higher level and frequency of Epstein-Barr virus in salivary gland epithelium and gland tissue (Fox, R. I. et al. *J. Immunol* 137:3162-3168 (1986)). Other viruses have also been considered by Fox, R. I. Current Opin. Rheum. 7:409-416 (1995).

Others have developed interesting data from Sjogren's syndrome. Pflugfelder and colleagues found evidence for Epstein-Barr virus in 80% of the lacrimal gland specimens from Sjogren's syndrome patients and in none of the controls (Pflugfelder, S. A. et al *Ophthalmology* 97:976-984 (1990); and Pflugfelder, S. A. et al. *Am. J. Pathol.* 143:49-64 (1993)). Karameris and colleagues found higher levels of hybridization between an Epstein-Barr virus DNA probe and the nuclei of salivary gland epithelial cells in Sjogren's syndrome than in controls (Karameris, A. et al. *Clin. Exp. Rheum.* 10:327-332 (1992)).

Others, however, found no such relationship and concluded that the frequency of Epstein-Barr virus DNA in salivary biopsy specimens was no different in patients with Sjogen's syndrome when compared with normals (Venables, P. J. W., et al. *Clin. Exp. Immunol.* 75:359-364 (1989); Venables, P. J. W., et al. *J. Autoimmunity* 2:439-438 (1989); Deacon, L. M., et al. *Am J. Med.* 92:453-454 (1992)). The data collected by Venables and colleagues were interpreted to show that there was "no evidence that the Epstein-Barr virus infection load is increased . . . [in Sjogren's syndrome]" (Venables, P. J. W. et al. *Clin. Exp. Immunol.* 75:359-364 (1989)), which is similar to the results of Maitland (Maitland, N. J. *Am. J. Med.* 96:97 (1994)). Venables and colleagues also refuted there being any abnormality in the serologic response of Sjogren's syndrome patients to Epstein-Barr virus (Deacon, E. M., et al. *J. Pathol.* 163:351-360 (1991)), citing their data as well as the negative serologic results of Mariette and colleagues (Mariette, X., et al. *Am. J. Med.* 90:286-294 (1991)).

A Japanese group found an increase in the Epstein-Barr virus production by B cells in patients with Sjogren's syndrome (Tateishi, M. et al. *Arthritis Rhuem.* 36:827-835 (1993)). Also, Inoue and colleagues found a minor increase in antibody levels against Epstein-Barr virus Nuclear Antigen-2 domains in Sjogren's syndrome compared to controls (Inoue, N. et al. *J. Infect. Dis.* 164; 22-28 (1991)). Another Japanese group reported a modest elevation of anti-Epstein-Barr Nuclear antigen, anti-Early Antigen and anti-Epstein-Barr virus Viral Capsid Antigen (all measured by immunofluorescence) (Toda, I., et al. Sjogren's syndrome (SS) and Epstein-Barr virus (EBV) reactivation. In Lacrimal Gland, Tear Film, and Dry Eye Syndrome. D. A. Sullivan, ed. pp 647-650 (Plenum Press, New York 1994)).

Nevertheless, Whittingham has proposed that Epstein-Barr virus is an etiologic agent for Sjogren's syndrome (Whittingham, S., et al. *Med. Hypothesis* 22:373-386 (1987)). She and her colleagues imagine that the Epstein-Barr viral RNAs called EBER 1 and EBER 2, which are known to bind the La autoantigen, facilitate overcoming tolerance to La and generating autoimmunity. They postulate that the combined effect of Epstein-Barr virus infection and autoimmunity leads to Sjogren's syndrome.

Morshed and colleagues published data showing an increased level of Epstein-Barr virus DNA in patients with primary biliary cirrhosis compared to controls from peripheral blood mononuclear cells, saliva, and fixed liver tissue (Morshed, S. A. et al. *Gastroenterol. Jpn.* 27:751-758 (1992)). The nuclear dot antigen is an autoantigen bound by autoantibody found in a few sera from patients with primary biliary cirrhosis. This autoantibody is also uncommonly found in lupus and rheumatoid arthritis sera. Analysis of the epitopes of the nuclear dot antigen has revealed two epitopes which have homology with Epstein-Barr virus protein sequences (Xie, K. and Snyder, M. *Proc. Natl. Acad. Sci.* 92:1639-1643 (1995)).

An example of double infection with Epstein-Barr virus and another virus is found in a cell line isolated from a patient with apparent multiple sclerosis (Haahr, S. et al. *Ann. N.Y. Acad. Sci.* 724:148-156 (1996)). The increased prevalence of seroconversion among multiple sclerosis patients, relative to controls, has led to the suggestion that Epstein-Barr virus may be an etiologic agent in multiple sclerosis (Sumaya, C. V. et al. *Ann. Neurol.* 17:371-377 (1985); Bray, P. F., et al. *Arch. Neurol.* 40:406-408 (1983); Larsen. P. D., et al. *Neurology* 35:435-438 (1985); Warner, H. B. and Carp. R. I. *Med. Hypothesis* 25:93-97 (1988); Bray, P. F. et al. *Neurology* (1992)).

Because of evidence implicating Epstein-Barr virus in infectious mononucleosis, B cell lymphoma (in immunocompromised hosts), Burkitt's lymphoma, nasopharyngeal carcinoma, and some cases of Hodgkin's lymphoma, there has been some activity building toward a vaccine against Epstein-Barr virus (Morgan, A. J., et al. *J. Med. Virol.* 29:74-78 (1989); and Morgan, A. J. *Vaccine* 10:563-571 (1992)). Recombinant vectors expressing gp340/220 in a bovine papillomavirus vector or in an adenovirus vector protected five of six cottontop tamarins from lymphomas that otherwise occur after infection with Epstein-Barr virus (Finerty, S., et al. *J. Gen. Virol.* 73:449-453 (1992)). A subunit of the gp340/200 in alum protected three of five cotton top tamarins from lymphomas (Finerty, S., et al. *Vaccine* 12:1180-1184 (1994)), suggesting that this strategy might not be especially effective. A trial of an Epstein-Barr virus vaccine of gp340/220 in a Vaccinia virus vector has been reported from China and failed to protect a third of those immunized (Gu, S. et al. *Dev. Biol. Stand.* 84:171-177 (1995)).

A variety of therapies have been attempted against Epstein-Barr virus. These include inducing the lysis cycle in cells latently infected by virus (Gutierrez, M. I., et al. *Cancer Res.* 56:969-972 (1996)). Patients with the Epstein-Barr virus related lymphomatoid granulomatosis have been treated with interferon-alpha 2b with the preliminary impression that the treatment was successful (Wilson, W. H., et al. *Blood* 87:4531-4537 (1996)). Cycloheximide has been demonstrated to be useful in vitro (Ishii, H. H., et al. *Immunol. Cell Biol.* 73:463-468 (1995)). Therapy with a T cell line has been attempted (Kimura, H. et al. *Clin. Exp.*

*Immunol.* 103:192-298 (1996)), as has adoptive transfer of gene-modified virus-specific T lymphocytes (Heslop, H. E. et al. *Nature Med.* 2:551-555 (1996)). Data available do not appear to particularly support the use of acyclovir for Epstein-Barr virus infections (Wagstaff, A. J., et al. *Drugs* 47:153-205 (1994)), though FK506 (a relative of cyclosporine) may have some benefit (Singh, N., et al. *Digestive Dis. Sci.* 39:15-18 (1994)). Monoclonal antibodies have been used to treat the virus-induced lymphoproliferative syndrome (Lazarovots, A. I., et al. *Clin. Invest. Med.* 17:621-625 (1994)).

It is therefore an object of the present invention to provide strategies to prevent autoimmune disease by vaccination with vaccines based upon Epstein-Barr virus or upon the structure of Epstein-Barr virus.

It is a further object of this invention to provide vaccines based upon Epstein-Barr virus or upon the structure of Epstein-Barr virus which will have little risk of inducing autoimmune disease.

It is a further object of this invention to provide diagnostics which will identify people exposed to Epstein-Barr virus who are at an increased risk for autoimmune disease and, alternatively, those who are at decreased risk for developing autoimmune disease.

It is a further object of this invention to provide for the application of antiviral therapy directed against Epstein-Barr virus in the treatment of autoimmune disease.

It is a further object of this invention to provide diagnostics and therapeutics for autoimmune disease based upon changes induced in the host by Epstein-Barr virus.

SUMMARY OF THE INVENTION

Data demonstrates autoimmune disease is caused by Epstein-Barr virus are shown. Some of the features of the mechanism in the specific example of the anti-Sm autoantibody response were found in systemic lupus erythematosus. Based on this evidence, an effective vaccine would prevent the autoimmune disease in those vaccinated, modified or administered so that the vaccine is not itself capable of inducing autoimmune disease. In the case of anti-Sm, structures to be avoided in an Epstein-Barr virus-derived vaccine have been identified.

Differences have been identified in the immune responses to Epstein-Barr infection between individuals who develop a specific autoimmune disease and those who do not. These differences are used to distinguish those who are at greater risk for developing specific autoimmune diseases from those who are a lesser risk.

Assuming Epstein-Barr virus causes autoimmune disease and that Epstein-Barr virus remains latent in the patient for life, reactivation of the virus from the latent state is important in generating or maintaining the autoimmune response that culminates in autoimmune disease. Cells infected with latent virus may also encourage autoimmunity. Based on the understanding that reactivation or latency are important to produce or sustain autoimmunity, then therapies directed against Epstein-Barr virus will also be effective therapies for the autoimmune manifestations of disease for which Epstein-Barr virus is responsible.

BRIEF DESCRIPTION OF THE DRAWINGS

FIG. 1A shows the background reactivity of the octapeptides with anti-human IgG conjugate alone. FIG. 1B shows the reactivity of the octapeptides with a normal human serum. FIG. 1C shows binding of a serum from a patient with systemic lupus erythematosus who precipitates the nRNP autoantigen, but not Sm autoantigen. FIG. 1D demonstrates the reactivity of a representative patient who has both anti-Sm and anti-nRNP autoantibodies as determined by specific precipitin formation in Ouchterlony immunodiffusion. (From J. A. James and J. B. Harley *J. Immunol.* 148; 2074-2079, (1992)).

FIG. 4A presents an example of the background binding found from a normal human serum. FIG. 4B presents the binding of the first serum available after presentation with lupus (from April, 1986) and FIGS. 4C and 4D present the binding of subsequent sera (from July, 1987 and December 1988, respectively). Solid arrows indicate the PPPGMRPP (SEQ ID NO:4) octapeptides and the open arrow the PPPGIRGP (SEQ ID NO:5) sequence. (From J. A. James et al *J. Exp. Med.* 181:453-461 (December 1995)).

FIGS. 5A-C are graphs of the binding of PPPGRRP-MAP™ (SEQ ID NO:1)-immunized rabbit sera and a Freund's control serum to the PPPGRRP-MAP™ (FIG. 5A SEQ ID NO:1)), PPPGMRPP-MAP™ (FIG. 5B SEQ ID NO:4), and nRNP/Sm antigen (FIG. 5C) by solid phase ELISAs (enzyme-linked immunosorbent assays). The bleeds of the rabbits are along the abscissa and the absorbence (×1000) on the ordinate. The preimmune serum (pb) and post-immunization bleeds 1 through 14 (Im1 to Im14) which span 52 weeks are indicated (U.S. Ser. No. 08/160,604 filed Nov. 30, 1993). The PPPGRRP (SEQ ID NO:1) peptide is found in the Epstein-Barr virus Nuclear Antigen-1 (EBNA-1).

FIG. 8A is from a normal who has no evidence of having been infected by Epstein-Barr virus by the assay for anti-Epstein-Barr virus Viral Capsid Antigen IgG. The other sera presented (FIGS. 8B through 8E) are all positive in this assay.

DETAILED DESCRIPTION OF THE INVENTION

Figure 1A:
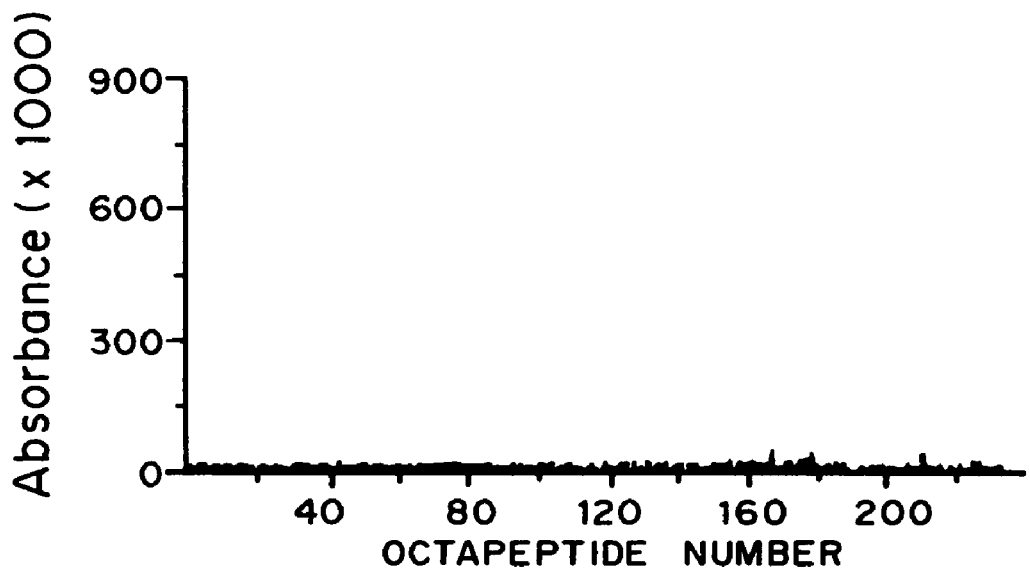
FIGS. 1A-D, are graphs of absorbence indicative of the antigenicity of overlapping octapeptides of an Sm B/B' polypeptide. Each number along the abscissa indicates the first amino acid of an octapeptide that begins with this amino acid (octapeptide number, 1-8, 2-9, 3-10, etc.). Each octapeptide overlaps its neighbor by seven amino acids.
Figure 1B:
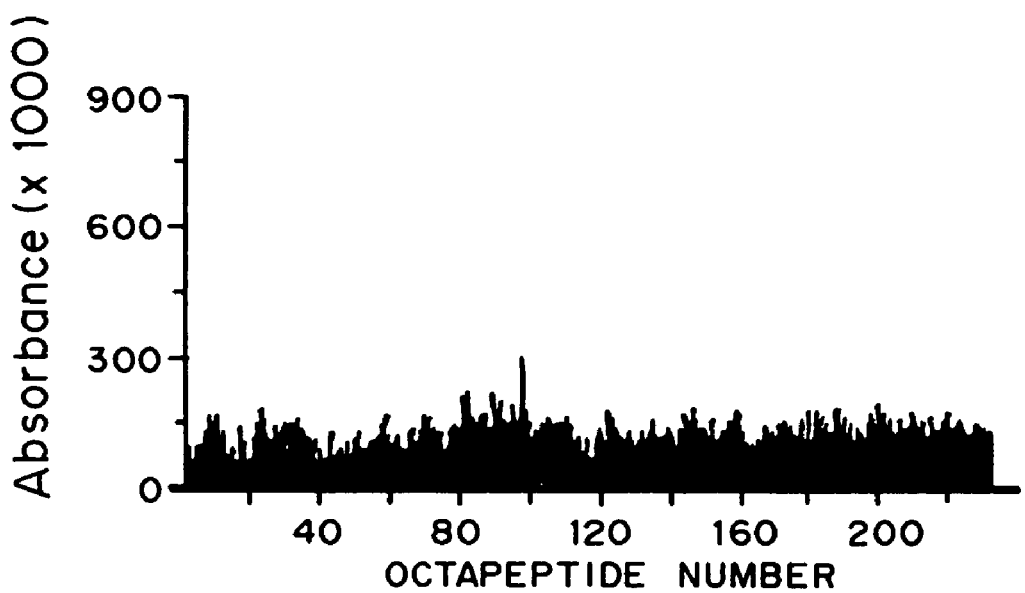
Figure 1C:
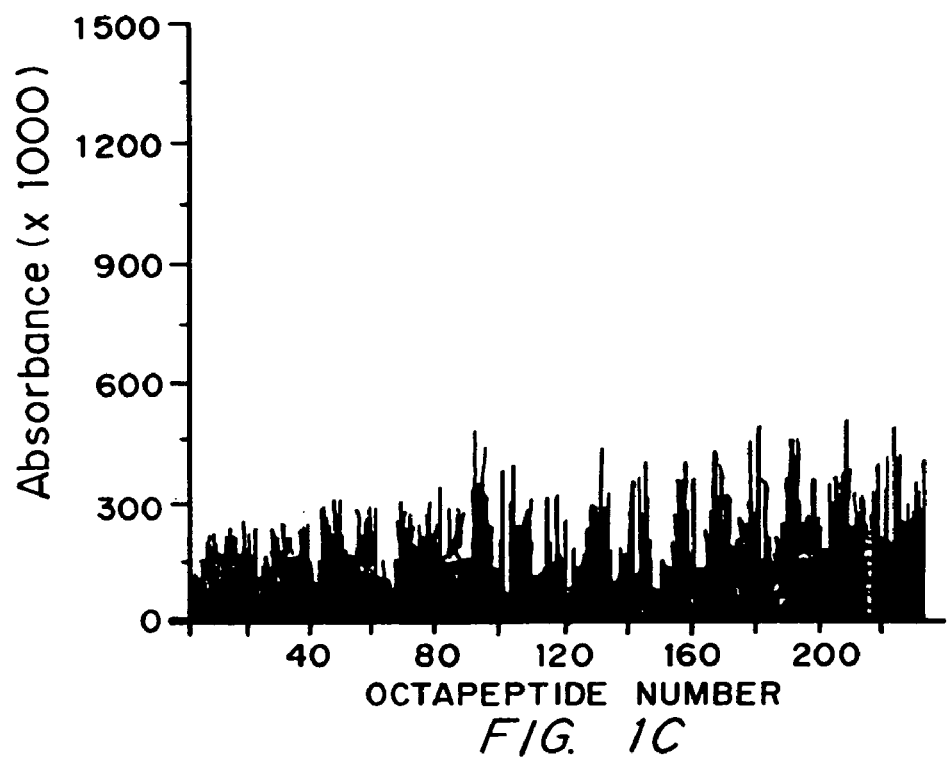

In the United States, about 95% of the adult population has been, and continues to be, infected with Epstein-Barr virus. Observations described herein indicate a small proportion of these develop autoimmune disease, related to this virus. Other factors are also likely to be important in the development of autoimmune disease, but are not essential to understand in order to develop therapeutics and diagnostics for use in diagnosing, treating and preventing or ameliorating autoimmune diseases involving Epstein-Barr virus as the etiologic agent. Epstein-Barr virus is the probable etiologic agent for nearly all cases of lupus, which serves as an example of autoimmune disease.

Diagnostics and therapeutics derived from the discovery that Epstein-Barr virus causes autoimmune disease as applied to the prevention, diagnosis and treatment of autoimmune disease are described herein. Systemic lupus erythematosus (lupus) is the particular autoimmune disease evaluated and for which data have been obtained. Within lupus, the work on a molecular understanding of the relationship between anti-Sm and systemic lupus erythematosus and the relationship of anti-Sm autoantibodies to Epstein-Barr virus is the best illustration of the data supporting these diagnostics and therapeutics.

The experiments described herein to address Epstein-Barr virus in lupus were guided by the results of immunochemical studies, not by the previous studies. These data pointed toward a curious mechanism in the anti-Sm autoantibody system in lupus which could involve Epstein-Barr virus.

The technology applied to the problem is very important in two ways. First, the assays for anti-Epstein-Barr virus antibodies have been dramatically improved. The classic method is to evaluate antibody binding to an Epstein-Barr virus infected cell line by immunofluorescence. This assay is dependent upon the expression of different Epstein-Barr virus proteins, depending upon whether the cell line is producing virus or the virus is latent. The autoantibodies of lupus often render these assays uninterpretable, making their use in lupus especially problematic.

Consequently, solid phase assays using enriched preparations of the surface antigen constitute a major improvement. The surface antigen is composed in part of a glycoprotein called gp340/220 or the Viral Capsid Antigen. These preparations of surface antigens have had many interfering substances removed. Epstein-Barr virus infection in man virtually always generates antibodies against this surface antigen. The assay is much simpler than is the cell line immunofluorescence assay and subject to much less variation in interpretation.

Second, molecular methods have been designed and developed to detect Epstein-Barr virus which appear to be at least as reliable as the serologic methods, and may even be superior. In normal adults Epstein-Barr virus infects only about one in every 20,000 to 500,000 B cells (Miyashita, E. M. et al. Cell 80:593-601 (1995)). B cells usually constitute only about 8% of the peripheral blood mononuclear cells. The vanishingly small quantity of Epstein-Barr DNA is lost in a relative ocean of genomic human DNA and is very difficult to detect. The improved sensitivity and specificity of detection of Epstein-Barr virus DNA improves the measurement made and leads to more accurate interpretation of the data. The older methods detected Epstein-Barr virus DNA in the peripheral blood in about 70% of individuals who had serologically converted, while the method described herein appears to detect more than 95% of those who have seroconverted and a few who have not seroconverted.

Reliable assays were used to address the prevalence of seroconversion and infection in the cases and controls in a way that took optimal advantage of the known properties of the viral infection. Others have selected sub-optimal study populations, have poorly chosen their controls, or have focused upon the quantitative level of antibody rather than qualitative evidence for infection, in addition to the technical problems outlined above in reliably detecting anti-Epstein-Barr virus seroconversion and Epstein-Barr viral DNA.

The data in the anti-Sm autoantibody system, discussed below, are used as a model in which the antigen presenting capacity of the B cell is important in generating autoimmunity. For example, the PPPGRRP (SEQ ID NO:1) structure is found in Epstein-Barr virus Nuclear Antigen-1. This sequence induced autoimmunity against the Sm B/B' of a rabbit after immunization. This autoimmunity not only included the related PPPGMRPP (SEQ ID NO:4) of Sm B/B', but also many other structures of B/B'. When the B cell generates a receptor that binds PPPGRRP (SEQ ID NO:1) and PPPGMRPP (SEQ ID NO:4) as found in native Sm B/B' then this B cell is capable of presenting the spliceosome to the immune system. Of course, once this cross reacting autoantibody is produced, then it may facilitate spliceosomal autoimmunity. Epstein-Barr virus is important because the immune control of the infected B cell is altered by the infection, rendering autoimmunity more likely. This mechanism can be directly extended to other antigens to generate other immune responses (both cellular and humoral) which lead to a variety of autoimmune diseases. Also, double infection with Epstein-Barr virus and another virus would extend the immune regulatory abnormalities to the antigens of the second virus.

Autoimmune Diseases

There are a large number of disorders in man that are thought to be autoimmune. These include systemic lupus erythematosus, autoimmune thyroid disease (Graves' disease or Hashimoto's thyroiditis), autoimmune beta islet disease of the pancreas (more commonly referred to as juvenile or Type 1 diabetes mellitus), primary biliary cirrhosis and many others. The particular disorders listed above are thought to involve antibodies produced in the host (the patient, in this instance) which bind to constituents of self. These antibodies are called autoantibodies. The particular constituent of self bound by the autoantibodies is associated with the different disorders. For example, anti-mitochondrial autoantibodies are associated with primary biliary cirrhosis. Anti-acetylcholine receptor autoantibodies are associated with myasthenia gravis. The list of such autoantibodies is quite long and often only one or a few autoantigens are bound by autoantibodies in each particular disorder. Systemic lupus erythematosus (or abbreviated as lupus herein) is an exception to this tendency, since many autoantibodies may be found in the disease and since patients do not necessarily share any particular autoantibody specificity. Anti-Sm (which is an anti-spliceosomal autoantibody specificity) is one of the autoantibodies closely associated with systemic lupus erythematosus, but even this autoantibody is found in only a minor fraction of patients with systemic lupus erythematosus. (Please refer to a review of this area (Harley, J. B. and Gaither, K. K. *Rheum. Dis. Clin. N. Amer.* 14:43-56 (1992)).

It is not sufficient just to produce autoantibodies. There must be some consequence of their presence in order to develop pathology which culminates in clinical disease. There are many instances of detecting autoantibodies in the absence of any detectable clinical illness. Autoantibodies may realize their pathologic potential by binding their antigen in the circulation. They then become part of circulating immune complexes. They may deposit in tissues, induce an inflammatory response, and cause tissue injury, as appears to occur in lupus. Autoantibodies may interfere with the functioning of receptors or otherwise activate cells as may happen in Wegener's granulomatosis or Graves' ophthalmopathy. Autoantibodies may simply block normal functioning of a protein, as happens to the acetylcholine receptor in myasthenia gravis. No doubt there are other mechanisms by which autoantibodies encourage clinical illness.

These mechanisms involve humoral autoimmunity; that is, autoimmunity that is mediated by autoantibodies. There is another form of autoimmunity mediated by cells, in particular T cells. Multiple sclerosis is thought by some to be an example of a disease that is mediated by autoimmune T cells. Although the methods and compositions described herein are particularly concerned with humoral autoimmunity, it is expected that cellular autoimmune processes are also involved with producing autoimmunity as a consequence of Epstein-Barr virus infection. As in many situations, one skilled in the art expects cellular immune mechanisms to dominate in some individuals and humoral mechanisms to dominate in others. This situation is expected to give rise to different clinical expression of disease. Tuberculous and lepromatous leprosy are examples where differences in the dominant form of the immune response lead to profound differences in the clinical illness, despite being caused by the same organism.

The traditional distinction between humoral and cellular immune mechanisms are being reevaluated under a new paradigm. T cells appear to have the capacity to respond in at least two ways. These cells are called Th1 and Th2, for T helper cells, Type 1 and 2. Characteristic cytokine production profiles are often used to distinguish these different responses. Th1 responses tend to be the more traditionally appreciated cellular immune responses. Th2 responses lead, among other consequences, to more of an antibody response and are more aligned with the classic humoral response. However, these boundaries do not appear to operate strictly since some types of antibody are more likely found in Th1 responses and the Th2 response clearly has its cellular component. Most autoimmune diseases probably have important components of both humoral and cellular autoimmunity.

Below, systemic lupus erythematosus is used as a particular example of an autoimmune disease. Data are presented which is consistent with the position that Epstein-Barr virus causes this autoimmune disorder. Lupus is one of many autoimmune diseases that are likely to share basic features, such as the causative agent being Epstein-Barr virus.

Definitions:

As used herein, autoimmune diseases are diseases that are primarily autoimmune, as well as diseases which do not appear to be primarily autoimmune but have immune manifestations involving immunoglobulins, antigen specific B cell surface receptors (surface immunoglobulin), or antigen-specific T cell receptors. Examples of diseases which fall into these categories are systemic lupus erythematosus, Sjogren's syndrome, rheumatoid arthritis, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, primary biliary cirrhosis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, autoimmune hemolytic anemia, pemphigus vulgaris, pemphigus, bullous pemphigoid, dermatitis herpetiformis, alopecia areata, autoimmune cystitis, pemphigoid, scleroderma, progressive systemic sclerosis, CREST syndrome (calcinosis, Raynaud's esophageal dysmotility, sclerodactyly, and telangiectasia), adult onset diabetes mellitus (Type II diabetes), male or female autoimmune infertility, ankylosing spondylitis, ulcerative colitis, Crohn's disease, mixed connective tissue disease, polyarteritis nodosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiform, postcardotomy syndrome, Cushing's syndrome, autoimmune chronic active hepatitis, bird-fancier's lung, asthma, allergic disease, allergic encephalomyelitis, toxic necrodermal lysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, chronic fatigue syndrome, fibromyalgia, Takayasu's arteritis, Kawasaki's disease, polymyalgia rheumatica, temporal arteritis, schistosomiasis, giant cell arteritis, *ascariasis*, aspergillosis, Sampter's syndrome (triaditis also called, nasal polyps, eosinophilia, and asthma), Behcet's disease, Caplan's syndrome, dengue, encephalomyositis, endocarditis, myocarditis, endomyocardial fibrosis, endophthalmitis, erythema elevatum et diutinum, psoriasis, erythroblastosis fetalis, fascitis with eosinophilia, Shulman's syndrome, Felty's syndrome, filariasis, cyclitis, chronic cyclitis, heterochromic cyclitis, Fuch's cyclitis, IgA nephropathy, Henoch-Schonlein purpura, glomerulonephritis, graft versus host disease, transplantation rejection, cardiomyopathy, Alzheimer's disease, parvovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, hepatitis B virus infection, hepatitis C virus infection, Waldenstrom's macroglobulinemia, mumps virus infection, and any other disorder in which the specific recognition of the host by immunoglobulin, B cell surface receptor (surface immunoglobulin), or T cell receptor is suspected or shown to be important in any aspect of the pathogenesis of the clinical illness.

Immunization is any procedure which leads to a cellular or humoral immune response directed against an identifiable and specific antigen, usually the immunogen. An antigen is a substance that is bound by antibody. Sometimes an antigen is also referred to when meaning a substance against which any immune response is directed and that it may be bound by antibody or lead to a cellular immune response. An autoantigen means a constituent of self that binds antibody (making it an autoantibody) or that induces a cellular response, for example, by a T cell. The spliceosome is that molecular apparatus, composed of RNA and protein, which splices heteronuclear RNA, thereby removing the introns from the coding sequence of RNA. The cellular response may be assayed by presentation of a peptide from the autoantigen, proliferation, cell activation, the prevention of cell activation, secretion of cytokines, activation of apoptosis, or other indication of an effect of the presence of the autoantigen. An autoantibody is any immunoglobulin, antigen specific B cell surface receptor (surface immunoglobulin), or antigen specific T cell receptor directed against self protein. Such T cell receptors usually bind peptides which themselves are bound by histocompatibility molecules. The T cell receptor usually binds to both the peptide and the histocompatibility molecule.

Therapy is a treatment by medical or physical means. A "treatment" is the composition used for treating a condition. Antiviral therapy is the use of a treatment in an effort to suppress or eliminate a virus, for example, suppression, elimination or other amelioration of the effect of Epstein-Barr virus. Peptides are small proteins composed of amino acids covalently bound to one another by peptide bonds. Peptides may be prepared by an in vivo mechanism, as in life, by using the nucleic acid encoding for the sequence of the peptide produced, or in vitro using peptide chemistry. A vaccine is a composition or preparation that induces an immune response in the recipient directed against a particular infectious agent.

Seroconversion means that the subject has developed antibodies of sufficient magnitude in the serum to conclude that the subject has made an immune response against the agent or substance of interest. Usually, this is the result of immunization (vaccination) or infection. Seropositive means that there are a sufficient quantity of antibodies with sufficient affinity to conclude that seroconversion has occurred. Seronegative means that the quantity and affinity of antibodies are not sufficient to conclude that seroconversion has occurred. In this application, the terms "lupus" and "systemic lupus erythematosus" are used interchangeably.

The single amino acid code is used in the figures and following examples, as follows:

| A - alanine | I - isoleucine | R - arginine |
| C - cysteine | K - lysine | S - serine |
| D - aspartic acid | L - leucine | T - threonine |
| E - glutamic acid | M - methionine | V - valine |
| F - phenylalanine | N - asparagine | W - tryptophan |

-continued

| G - glycine | P - proline | Y - tyrosine |
| H - histidine | Q - glutamine | |

Therapeutic and Diagnostic Compositions

Vaccines

Immunity against a viral infection can be induced using either peptides, viral proteins or other components of the virus such as carbohydrate components, substances which imitate structures of the virus, or the virus. In the preferred embodiment, the vaccine is based on the viral proteins wherein the epitopes cross-reactive with the splicesomal proteins are deleted. In other embodiments, the vaccine is based on viral proteins where epitopes cross-reactive with antibodies to other known autoantigens are deleted or altered to decrease their immunoreactivity with autoantibodies. In still other embodiments, the vaccine includes the virus, either live, modified or inactivated, or components thereof, in a vehicle which can be administered in a dosage form and over a schedule eliciting a strong immune response to kill the virus, but which does not elicit an autoimmune response.

An unmodified vaccine may be useful in the prevention and treatment of autoimmune disease related to Epstein-Barr virus. The dose, schedule of doses and route of administration may be varied, whether oral, nasal, vaginal, rectal, extraocular, intramuscular, intracutaneous, subcutaneous, or intravenous, to avoid autoimmunity and, yet, to achieve immunity from Epstein-Barr virus infection. The response to the unmodified vaccine may be further influenced by its composition. The particular adjuvant employed (its concentration, dose and physical state), concentration of the virus in the vaccine, and treatment of the unmodified vaccine with physical environmental changes, for example, temperature and pressure, the particular buffer, and the particular preservative(s) (if any) will be selected to reduce the likelihood of developing an autoimmune disorder, for example using the animal strains discussed below. This same or different vaccine may be useful in reducing or eliminating the effect of an existing latent or active Epstein-Barr virus infection upon autoimmunity.

Peptides of up to about forty amino acids, more preferably between four and twenty-five amino acids, most preferably eight amino acids, can be synthesized using any one of the methods known to those skilled in the art. In general, an epitope of a protein is composed of between three or four and eight amino acids (see Watson et al., "Certain Properties Make Substances Antigenic," in *Molecular Biology of the Gene*, Fourth Edition, page 836, paragraph 3, (The Benjamin/Cummings Publishing Company, Menlo Park, 1987). As used herein, the peptides can contain the entire native epitope, or portions thereof sufficient to react with autoantibody.

Although described in the literature with reference to specific sequences encoding viral proteins or the autoantigens, a number of substitutions using natural or synthetic amino acids can be made in the peptides to yield an peptide acting as a linear epitope that is functionally equivalent to the disclosed sequences, for example, as demonstrated by James and Harley, *J. Immunology* 148:2074-2079 (April 1992). Accordingly, the term linear epitope as defined by a specific sequence is used herein to include peptides having substitutions yielding a peptide bound in an equivalent manner or extent by an antibody or autoantibody. For example, using monoclonal antibodies against peptide determinants of Sm B/B', substitution studies demonstrated that A, G, and S can substitute for R in PPPGMRPP (SEQ ID NO:4) in the binding of one antibody, KSm3. Analogously, F, H, T, V and Y can substitute for 1 in PPPGIRGP (SEQ ID NO:5) in the binding of KSm3.

Figure 1D:
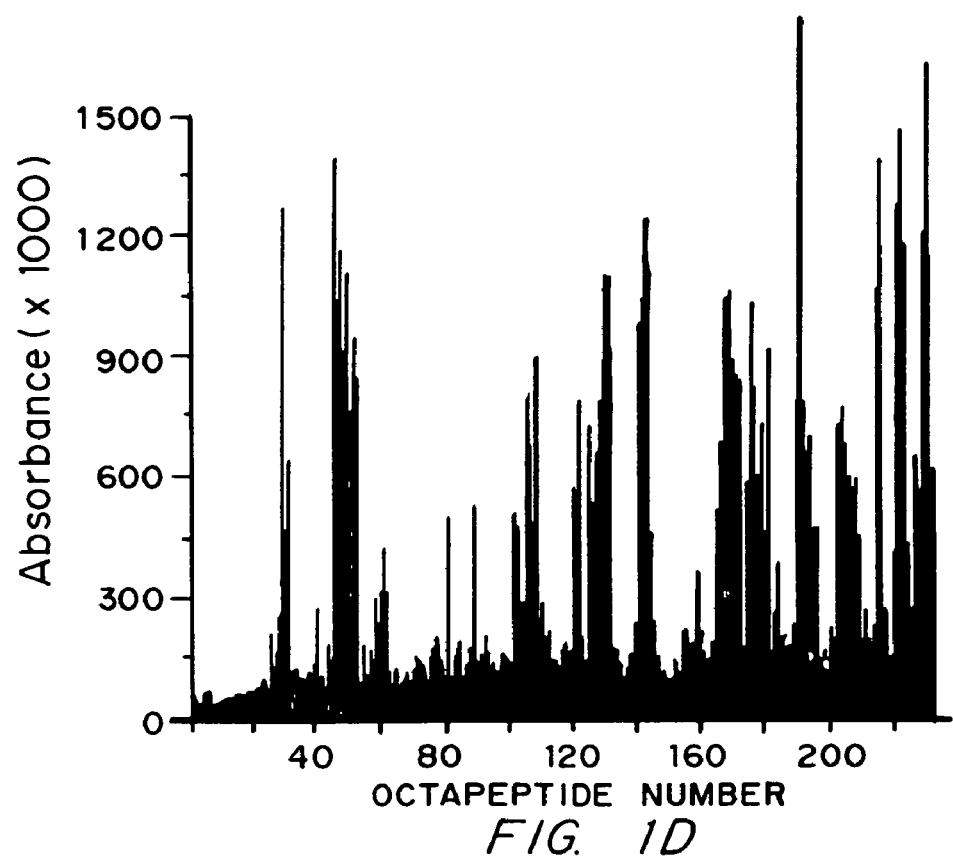
Figure 2:
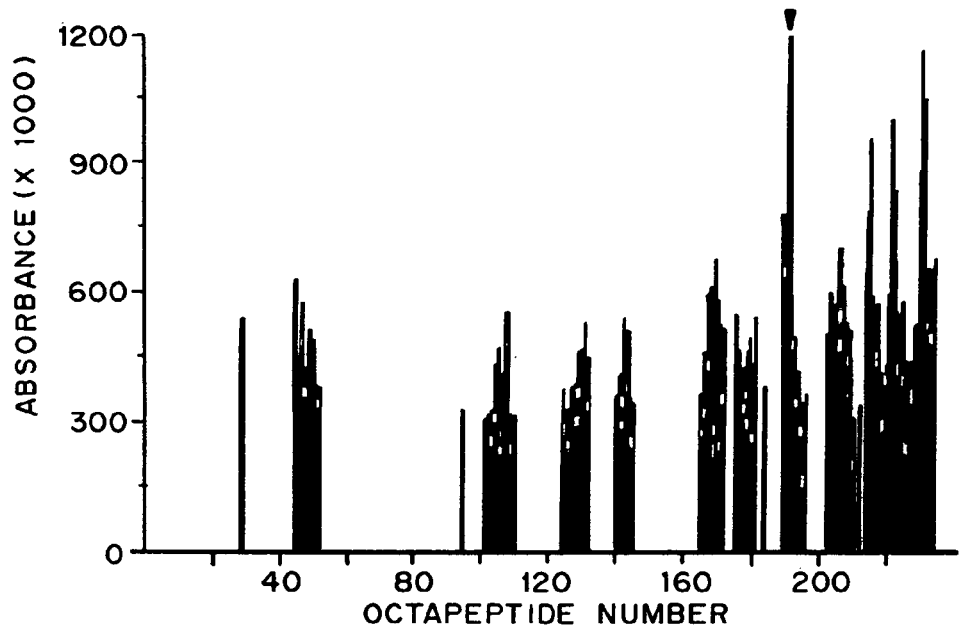
FIG. 2. Mean binding to overlapping octapeptides by Sm and nRNP precipitin positive lupus patients showing the major epitopes (as defined as being greater than 0.5 O.D., or a mean of 10 standard deviations above the mean binding of normal sera). Binding below the threshold of 0.325 O.D., or the mean of normals plus two standard deviations, has been omitted for clarity. The standard error is depicted as an open box below the mean in the bar representing the mean of the lupus patient binding. (From J. A. James and J. B. Harley *J. Immunol.* 148; 2074-2079, (1992)).

Solid phase binding of autoantibodies to peptides has proven useful for examining sequential linear epitopes, also referred to as "linear" or "sequential". These have been useful to define important residues in epitope structure. This approach may or may not be less useful in defining conformational epitopes or regions where two or more linear epitopes are brought together by the tertiary structure. The particular structural relationships between the autoantigens and autoantibody with particular regard to the particular conformation assumed by the peptide determines what can be learned by this approach. In addition, although many peptides may assume conformations in solution that are not found in the native protein structure, true epitopes may still be delineated by this method. Those peptides that tend to have a structure similar to that found in the native molecule are expected to usually be bound by a larger proportion of the autoantibodies that bind the analogous sequence on the native protein and/or may be bound with greater affinity.

It is believed that naturally arising human lupus follows a progression similar to that induced in the rabbit model described in the examples. Using this model, an immune response to a peptide, one very similar to a region of EBNA-1, is the seminal, initiating event for the subsequent autoimmunity and disease manifestations of lupus, where they occur. A structure, such as a peptide, that is capable of inducing autoimmunity is not necessarily identical to the structure found in the autoantigen. Indeed, it is possible that these structures would commonly be at least slightly different, when comparing the substance that induces the autoimmune response and the analogous structure in the autoantigen. On the other hand, there must be a basis for the non-autoantigen substance to induce autoimmunity. This is best identified as a cross-reaction wherein the immune recognition molecule binds, though not necessarily equally, to both the non-autoantigen substance as well as to the autoantigen.

The proposed mechanism is as follows. An immune response against a non-autoantigenic substance occurs. Some fraction of the antibodies thereby produced recognize the autoantigen and hence are autoantibodies. These autoantibodies facilitate the processing and antigen presentation of the autoantigen via the B cell surface immunoglobulin which serve as receptors, in this case for autoantigen, or via immunoglobulin cell surface receptors that are found on a variety of cells capable of antigen presentation. Once this occurs the immune response expands to other structures of the autoantigen and a full-blown, complete autoimmune response against the autoantigen ensues, which can result in clinical illness.

Based on this mechanism, the autoimmune responses progress from one or a few initial antigenic structure(s) to a much more complex response focused upon the autoantigen. Elucidating the pattern of progression and understanding the relationship of autoimmune serologic findings to clinical manifestations places the physician in a strong position to accurately prognosticate and prepare patients and their families for the more likely outcomes.

In the case of systemic lupus erythematosus and the anti-Sm response, one method is to repeat the assays determining autoantibody binding to peptides over time. The effect of the peptide in vitro on cells from patients can also be measured. Proliferation, secretion of cytokines, interferons and other substances, expression of cell surface molecules and activation are typically useful diagnostic indicators.

This strategy to generate autoimmunity can also be used to develop reagents that are useful in diagnosis or treatment of autoimmune disorders. Animal antibodies that compete with or otherwise facilitate the identification of particular fine specificities of binding can be important in evaluating prognosis. Moreover, the peptide binding pattern to the octapeptides from the nRNP A protein show two different patterns. It should be possible to correlate a particular pattern found in a patient to obtain an indication of the stage of the disease process as well as of the clinical prognosis. Reagents developed as a consequence of immunizing animals with autoantigenic peptides could be used to identify these differences. Such reagents include antisera, T cell lines, subsets of antibodies, individual antibodies, subsets of cells bearing a subset of the T cell receptors, individual T cell receptors, and cytokines and other substances elaborated by cells from the animal. The antibodies and T cell receptors are construed to include recombinant antibodies or T cell receptors derived from a peptide-immunized animal.

The RNA-protein particles which are the major autoantigens may now be purchased commercially. The reagents made available by the animal model of autoimmunity described herein will be useful in the manufacturing and testing of autoantigens. Affinity purification using animal antiserum (absorbed or otherwise prepared) could be used for purification of the naturally occurring autoantigens.

Having a mechanism of disease provides the opportunity to apply new strategies for prevention of disease and for specific immunologic correction of the immune abnormalities that lead to disease, and therefore more accurately design the therapy.

For example, with the realization that the generation of autoimmune disease can be divided into phases comes the appreciation that the therapeutic opportunities will be similarly partitioned. As a specific example, the influence of vaccination with an analog of PPPGMRPP (SEQ ID NO:4) will be different depending not only upon the structure of the immunogen, but also upon the pharmaceutical carrier, upon the maturity of the autoimmune response against PPPGMRPP (SEQ ID NO:4) and Sm, and upon other therapeutics that may be administered concomitantly. Such therapeutics include drugs as well as biologics, such as cytokines, immunoglobulins, and interferons, among others.

As a second specific example, mice strains exist which produce lupus autoimmunity, as well as strains which do not produce lupus autoimmunity, after immunization with PPPGMRPP-MAP™ (SEQ ID NO:4). The genetic, biochemical, and physiological differences between these strains can be used to develop diagnostics, including genetic markers and risk factors, and therapeutics for autoimmune disease, especially lupus, using techniques known to those skilled in the art.

As discussed above, based on the data confirming that Epstein-Barr virus is an inducing agent for lupus, it is possible to design therapeutics to prevent or inhibit further progression of lupus by vaccinating with Epstein-Barr virus, or components thereof, using standard vaccination procedures, most preferably after alteration or removal or masking of the sites which elicit the autoimmunity.

The peptides can be used therapeutically in combination with a pharmaceutically acceptable carrier. The peptides can be administered in a dosage effective to block autoantibodies or as a vaccine to block the production of autoantibodies, by eliciting a protective immune response against non-autoantigenic regions of the pathogen. The peptide acts as a functional antagonist by binding to antibody that does not stimulate or activate the immune cells and thereby block the immune response to the autoantigens.

Pharmaceutical carriers are known to those skilled in the art. These most typically would be standard carriers for administration of vaccines to humans, including solutions such as sterile water, saline, and buffered solutions at physiological pH. Peptides used as vaccines are most preferably administered intramuscularly or subcutaneously. Other compounds will be administered according to standard procedures used by those skilled in the art.

Alternatively, the peptides used for treatment can include peptides homologous to an identified antigenic sequence. These peptides, either free or bound to a carrier, could be delivered to a patient in order to decrease the amount of circulating antibody with a particular specificity. In addition, knowledge of the cross-reacting epitopes between a foreign antigen and an autoantigen may allow for re-induction of tolerance. It is well known in experimental models of the immune response that the response can be suppressed and tolerance induced by treatment with the antigen. Peptide therapy with the cross-reacting sequences may be a useful therapy in autoimmune diseases.

The amino acid sequences can also be used to make agents for neutralizing circulating antibodies or immobilized on substrates in extracorporeal devices for specific removal of autoantibodies, using methodology known to those skilled in the art.

Diagnostics

Individuals who are not at as great a risk for developing autoimmune disease can be identified by reactivity to the various peptides, for example, as demonstrated in the examples where individuals who are not prone to develop lupus are characterized by antibodies to GAGAGAGAGAGAGAGAGAGAGAGA (SEQ ID NO: 7). Other structures derived from Epstein-Barr virus can be used to predict who will develop autoimmune disease. For example, GAGAGAGAGAGAGAGAGAGAGAGA (SEQ ID NO:7) is a commonly identified antigen from Eptein-Barr virus in normal individuals, while lupus patients do not tend to bind this structure. An individual identified at risk for the development of an autoimmune disease, but who does not yet manifest autoimmunity or symptoms of the disease, may require a special therapeutic approach. This is an opportunity to induce immune suppression before the process leading to autoimmune disease is initiated. Strategies such as intravenous administration of large amount of the initiating structure is known to induce tolerance. Small sub-immunogenic doses of the initial immunogen can also be used to induce tolerance.

There is a limited opportunity to interrupt or redirect an immune response that has been initiated against the first components of the autoantigen. Here again the induction of suppression by the use of the component peptides or analogs thereof with or without concomitant drugs or biologics has the potential to inhibit progression into an autoimmune disorder. Once autoimmunity against the autoantigen is established, the use of component peptides or their analogs with or without concomitant drugs or biologics may interrupt the course of the autoimmune response, thereby ameliorating the illness.

The animal model provides an opportunity to optimize ways of interrupting and reversing the autoimmune process. For example, it has been observed that one of the rabbits immunized with Map-PPPGMRPP (SEQ ID NO:4) seemed to improve clinically somewhat after developing the most severe manifestations of systemic autoimmunity. If this result is the effect of a particular antibody, then this antibody may have the capacity to influence the maturation of the immune response toward alleviating the disease in other species. For example, such an antibody could be isolated by biochemical methods, by recombinant DNA methods or by hybridoma monoclonal methods, humanized using standard technology and then administered to patients as a specific therapeutic agent for disease. T cell receptors or cytokines could be equally useful.

Assays

Subsets of antigenic peptides have the potential to identify patients at risk for particular clinical manifestations or patients in particular prognostic groups. The peptides can be used in combination in assays, such as the solid phase assay, to classify patients.

Specifically, the peptides that are bound by autoantibodies in patients characterized by specific disorders, such as renal disease or central nervous system involvement, are selected and combined in an assay, such as an ELISA for a test to detect the collection autoantibodies that bind this articular collection of peptides. Using a mixture of peptides may increase the efficiency and reliability of such assays, as compared with using a single autoantigen, or a single peptide.

The peptides can be used in solution or immobilized to a solid substrate, such as a gel suitable for affinity chromatography, or a multi-well plate, using standard techniques such as the commercially available cyanogen bromide.

The present invention will be further understood by reference to the following non-limiting examples.

EXAMPLE 1

The Relationship of Anti-Sm to Epstein-Barr Virus

The anti-Sm and anti-nuclear ribonucleoprotein (nRNP) autoantibody specificities have an Ouchterlony precipitin reaction of partial identity. This is because the epitopes bound are found on two antigens which share some, but not all, antigenic features. The Sm autoantigen may be found in association with the U1, U2, U5 or U4/6 spliceosomal particles. These are composed of specific U RNA and particular peptides. The nRNP autoantigen is composed of only U1 RNA and particular unique peptides. The anti-Sm antibodies bind to the B/B' or D spliceosomal peptides in Western blot while the anti-nRNP autoantibodies bind 70K, A or C peptides (Lerner, M. R. and Steitz, J. A. *Proc. Natl. Acad. Sci. USA* 76:5495-5499 (1979); Hinterberger, M. *J. Biol. Chem.* 258:2604-2613 (1983); and Petterson, I. et al. *J. Biol. Chem.* 259:5907-5914 (1984)). (B/B' and D are found in the U1, U2, U5 and U4/6 spliceosomal particles. A protein termed the N protein or the Sm N protein is closely related to B and B'. 70K, A and C are usually only found in U1.) Anti-Sm precipitins are found in about 10% to 20% of lupus patients. Anti-Sm is sufficiently specific for this diagnosis that its presence in the serum has become part of the 1982 Criteria for the Classification of Systemic Lupus Erythematosus (Tan E. M., et al *Arthritis Rheum.* 25:1271-1277 (1982)).

Antigenicity of B/B' Peptides Assessed by Measuring Antibodies Binding to Octapeptides Synthesized In Vitro from the Sequence of the B/B' Sm Peptide.

The autoantigenicity of Ro (also known as the SS-A) autoantigen was reported by Scofield, R. H. et al. *Proc. Natl. Acad. Sci. USA* 81:3343-3347 (1991). The antigenicity of the B/B' peptides was assessed by measuring antibodies binding to octapeptides synthesized in vitro from the sequence of the B/B' Sm peptide, as described by James, J. A. and Harley, J. B. *J. Immunol.* 148:2074-2079 (1992). Representative data from an anti-Sm precipitin positive patient are shown in FIG. 1D and controls in Figures A-C. Note that eleven groups of peptides are bound by the sera containing anti-Sm autoantibody. One of the most unexpected observations was that all of the anti-Sm sera tested bound almost the identical octapeptide structures (FIG. 2).

The sequence PPPGMRPP (SEQ ID NO:4) is repeated three times in Sm B' (Van Dam, A. et al. *EMBO J.* 8:3853-60 (1989)). The N protein, which is very homologous to the B/B' protein, has three repeats of PPPGMRPP (SEQ ID NO:4) and a closely related sequence PPPGIRGP (SEQ ID NO:5) is also found once (Schmauss C. et al. *Nuc. Acid Res.* 17:1733-43 (1989)). PPPGIRGP (SEQ ID NO:5) is not found in the B' protein; rather, PPPGMRGP (SEQ ID NO:8) is found in its place. Much confusion has surrounded this area due to the original publication of the Sm B/B' sequence (Rokeach L. A. et al. *J. Biol. Chem.* 264:5024-30 (1989); Sharpe N. G. et al. *FEBS Lett.* 250:585-90 (1989)) which was later found to actually produce what is now termed the N protein or the Sm N protein (Schmauss C. et al. *Nuc. Acid Res.* 17:1733-43 (1989)). Lupus patients with anti-Sm precipitins all have antibodies which bind to both Sm B (a truncated version of Sm B'), Sm B' and Sm N. Substantial cross-reactivity occurs between the three proteins.

Figure 3:
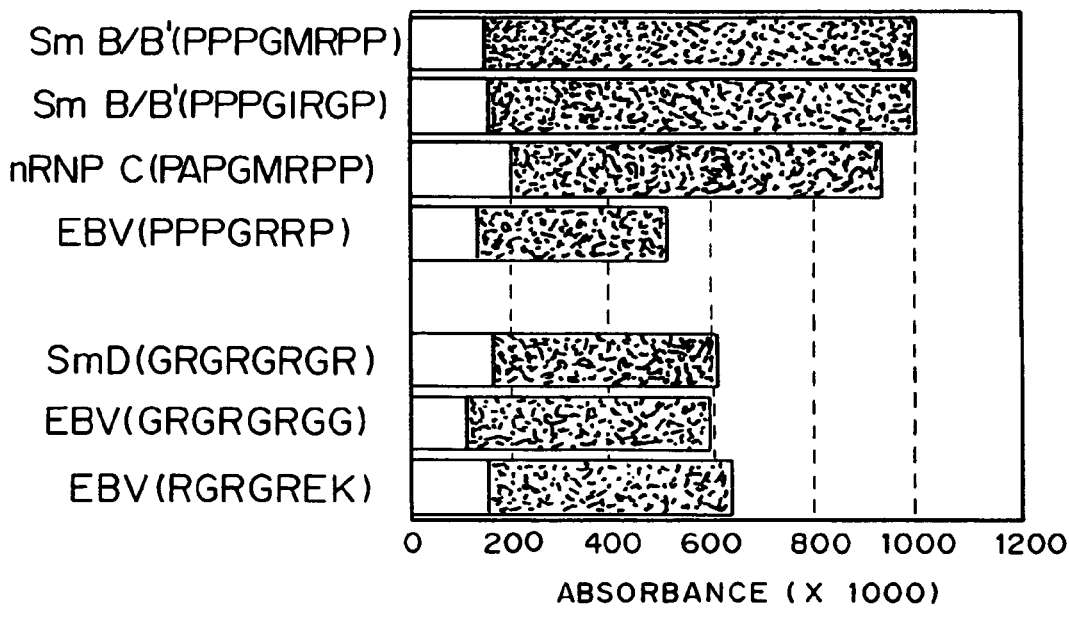
FIG. 3 is a graph of binding to selected peptides from the B/B', C and D spliceosomal proteins and from Epstein-Barr virus nuclear antigen-I proteins (PPPGRRP (SEQ ID NO:1), GRGRGRGG (SEQ ID NO:2), and RGRGREK (SEQ ID NO:3)) in six lupus patient sera (which are anti-Sm and anti-nRNP precipitin positive) (black) and five control sera (shown overlaid in white). The peptides shown are, in order, SEQ ID NO:4, SEQ ID NO:5, SEQ ID NO:6, SEQ ID NO:1, amino acids 1 to 8 of SEQ ID NO:9, SEQ ID NO:2, and SEQ ID NO:3.
Figure 4A:
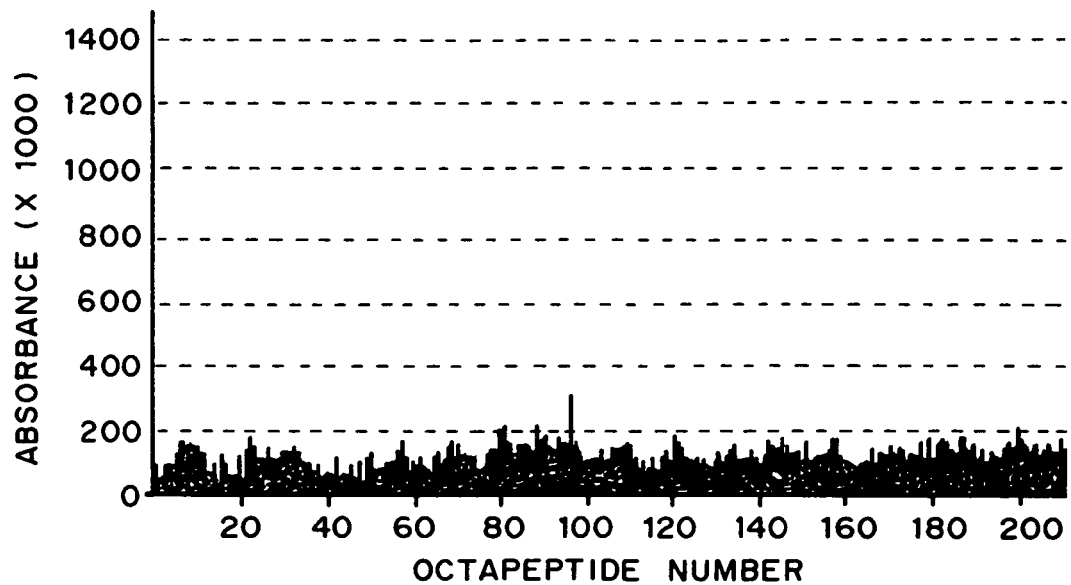
FIGS. 4A-D are graphs of the development of an anti-Sm B/B' response in one anti-Sm and anti-nRNP precipitin positive patient. Binding to 211 octapeptides of Sm B/B' is presented as absorbence (×1000) at 405 nm.
Figure 4B:
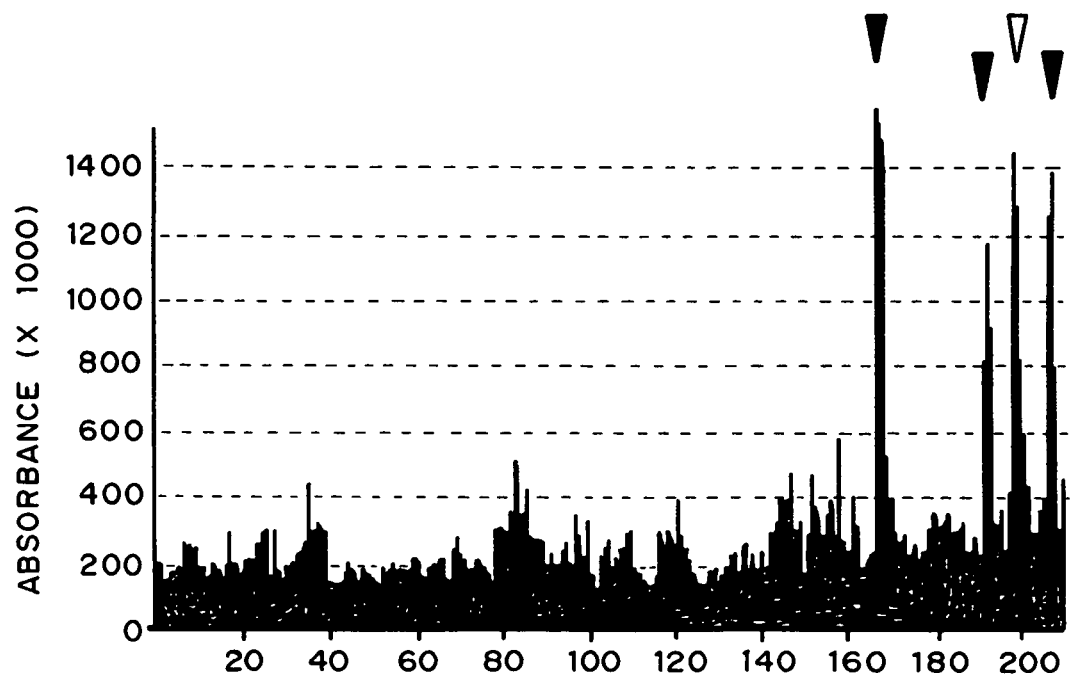
Figure 4C:
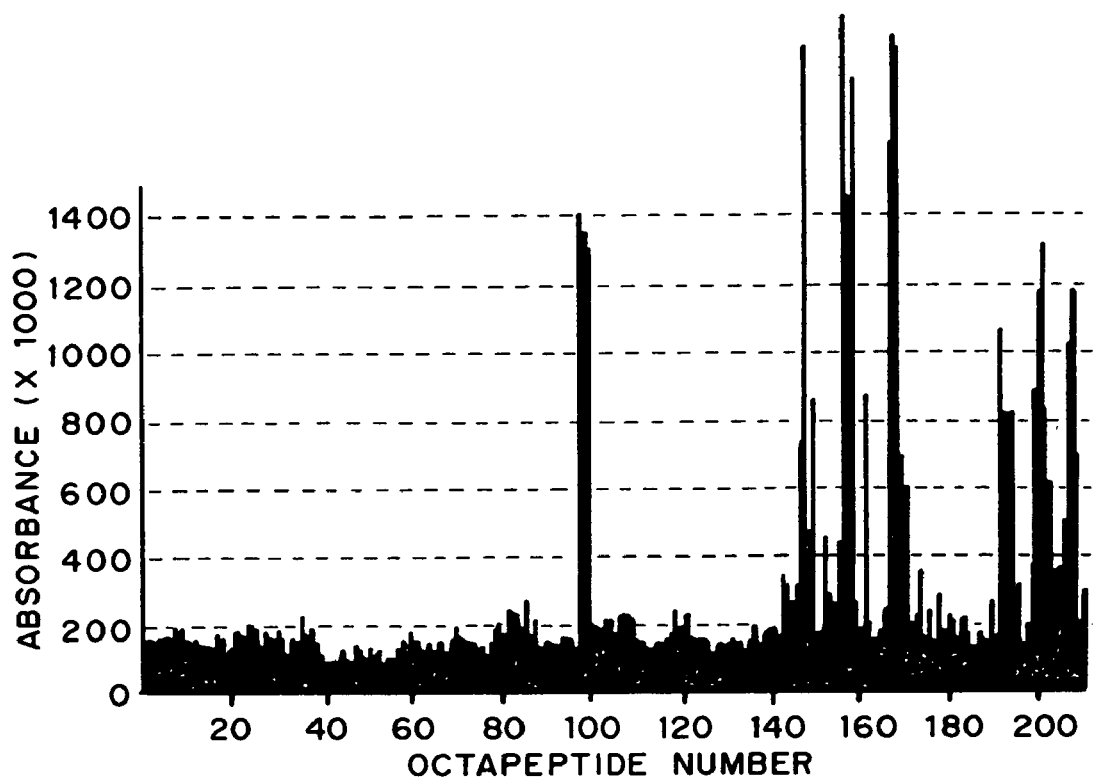
Figure 4D:
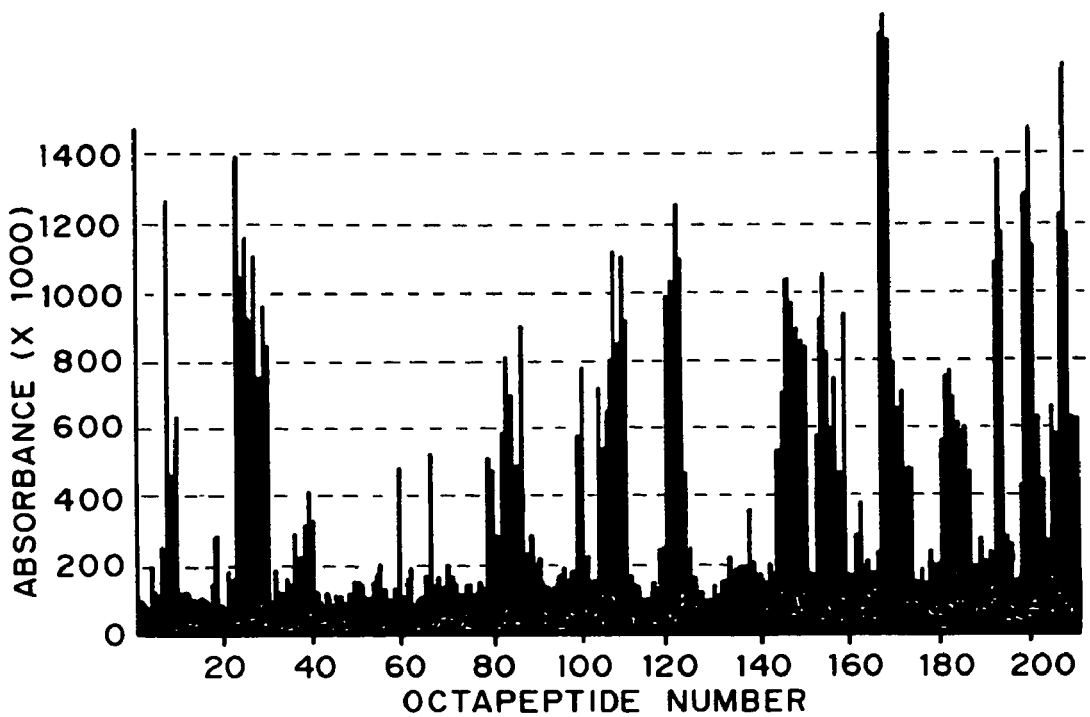
Figure 6A:
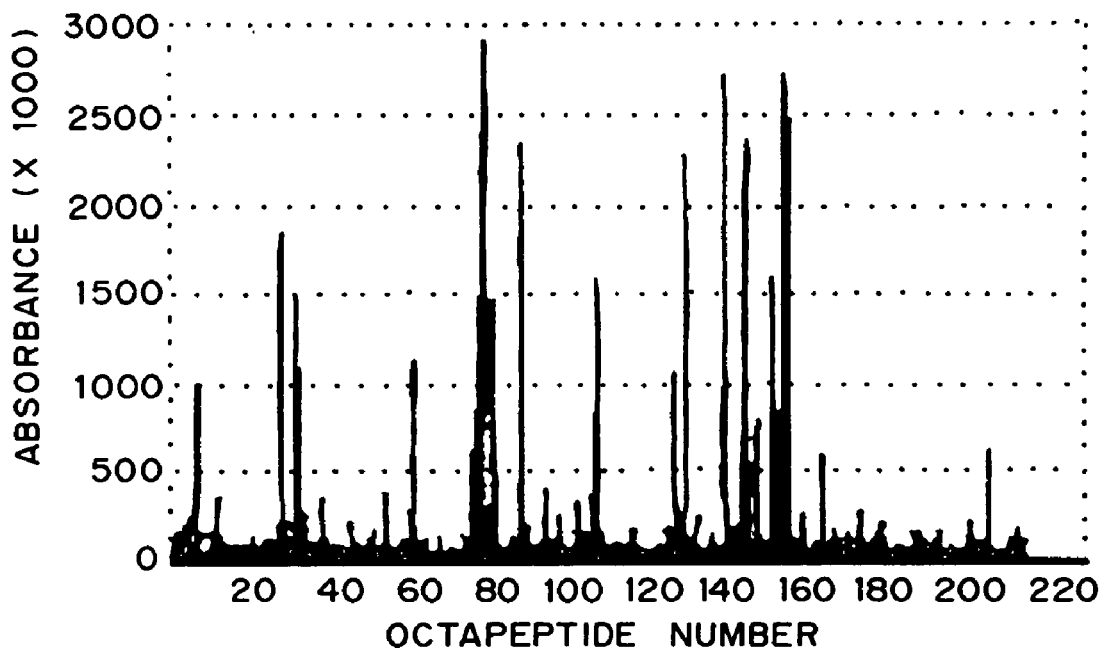
FIGS. 6A-D are graphs of the binding of two rabbit sera to the overlapping octapeptides of the spliceosomal proteins B/B' (FIGS. 6A and 6C) and D (FIGS. 6B and 6D). The two rabbits (numbers 40 and 41) were immunized with PPPGRRP-MAP™ (SEQ ID NO:1) 86 days earlier. The serum in FIGS. 5A and 5B binds to nRNP/Sm, and is positive in the antinuclear antibody assay and the anti-double stranded DNA assay (*Crithidia lucilea* kinetoplast fluorescence assay) while the serum from the second rabbit was not positive in any of these other assays (NY Acad. Sci. 815:124-27, 1997; PCT/US93/03484 entitled "Methods and Reagents for Diagnosis of Autoantibodies" by the Board of Regents of the University of Oklahoma").
Figure 6B:
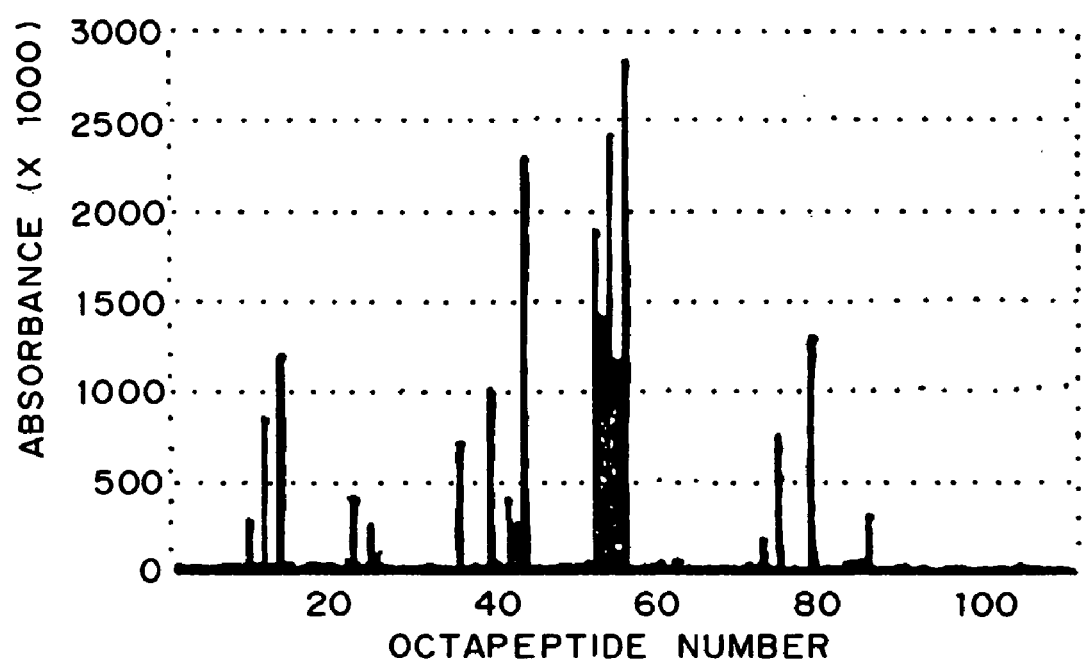
Figure 6C:
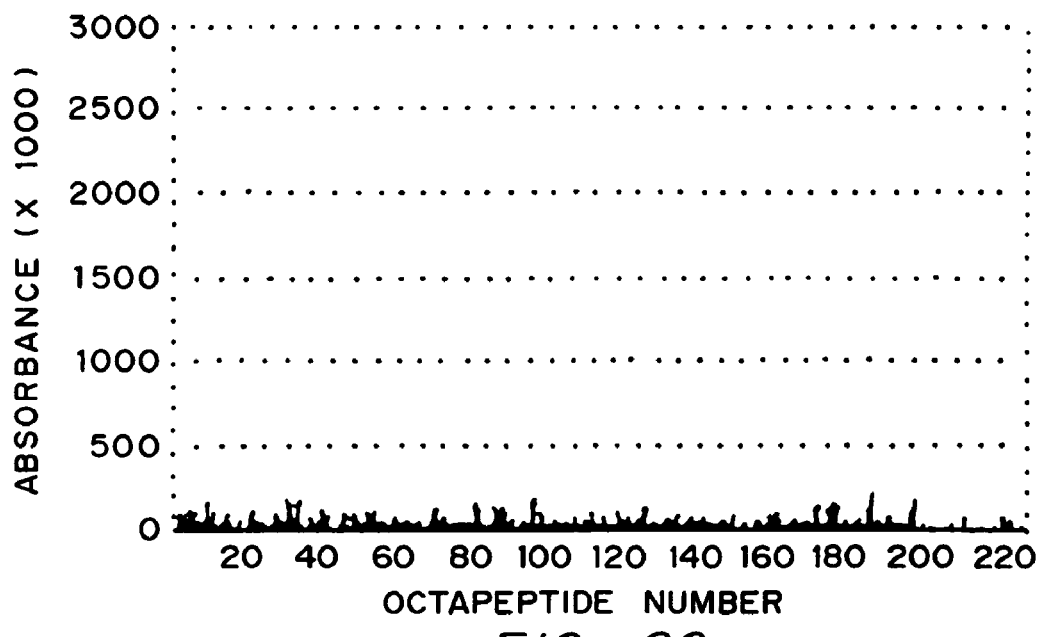
Figure 6D:
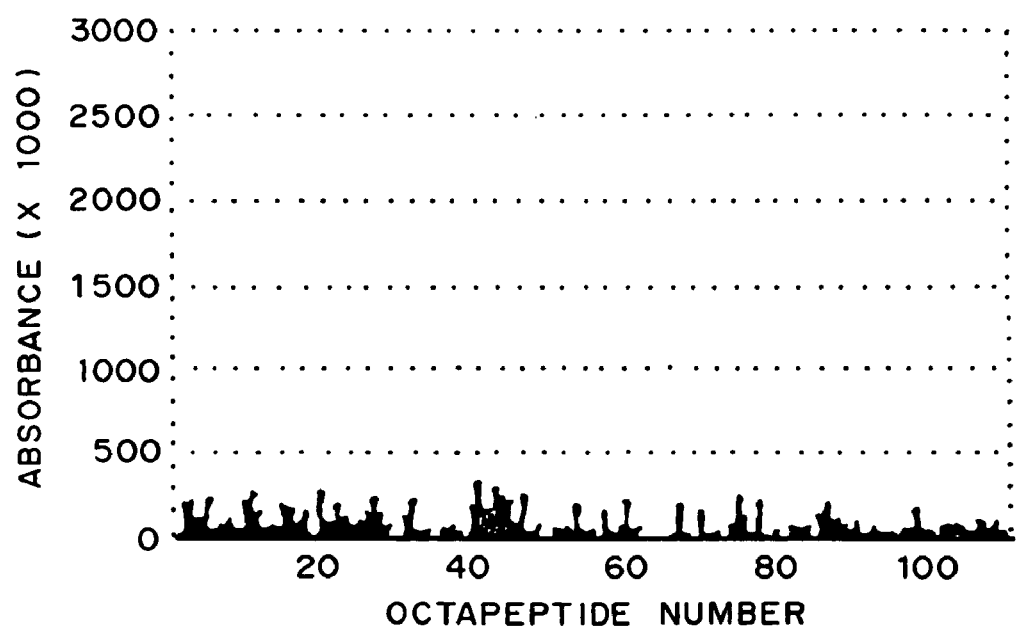

Such repeated closely related structures are sometimes particularly immunogenic. These anti-Sm sera also bind to some of the known sequences which are structurally similar to PPPGMRPP (FIG. 3 SEQ ID NO:4). These sequences included PPPGRRP (SEQ ID NO:1), which is found in the Epstein-Barr Nuclear Antigen-1 (EBNA-1) protein. GRGRGRGG (SEQ ID NO:2) and RGRGREK (SEQ ID NO:3) are also sequences from Epstein-Barr virus Nuclear Antigen-1, but these are similar to a major antigenic epitope of Sm D in lupus patients, GRGRGRGRGRGRGRGRGRGRGG-PRRR (SEQ ID NO:9) (James, J. A., et al. *Clin. Exp. Imunol.* 98:41-426 (1994)). (See GenBank accession code: gb-vi.ebv for sequences of Epstein-Barr virus proteins.) All three peptides appear to bind at least three times more antibody from the anti-Sm precipitin positive lupus patient sera than the controls. The antibody binding to these peptides in the lupus patient sera was over half of the antibody binding level found for PPPGMRPP (SEQ ID NO:4).

Serum Samples from Lupus Patients Stored Early in the Course of the Disease Process Bind Only PPPGMRPP (SEQ ID NO:4) (and Neighboring Peptides) of the 233 Possible Octapeptides of B/B'

The analysis of stored sera revealed that a serum sample from an lupus patient stored early in the course of her disease process bound only PPPGMRPP (SEQ ID NO:4) (and neighboring peptides) of the 233 possible octapeptides of B/B' (FIG. 4) (James, J. A. et al. *J. Exp. Med.* 181:453-461 (December 1995)). Positive sera has been received and stored for 17 years to yield a collection of about 80,000 specimens from 26,000 individuals. Therefore, this Clinical Immunology database was screened to identify lupus patients who developed anti-Sm under observation. The clinical serum bank was found to contain stored serum specimens from 161 patients with anti-Sm antibodies in at least one serum sample. Four patients were identified among these who, during their SLE clinical course or after initial presentation, converted from being precipitin negative to precipitin positive for antibodies to Sm. Sera from each individual were retrieved from before and after the development of anti-Sm antibodies.

For each serum sample, antibody levels were tested by ELISA for binding to Sm and the Sm/nRNP complex. The Ro protein was selected as a control antigen since none of the four patients demonstrated anti-Ro antibodies by Oüchterlony immunodiffusion. Each patient increased binding towards the Sm and Sm/nRNP antigens over time, without an increase in binding to the Ro protein (above background levels) by ELISA. Anti Sm B/B' indicated specificity was confirmed by Western blotting. Binding to Sm B/B' indicated acquisition of a new antibody specificity, since binding to this protein was not detected in the first available sample tested from each patient.

Each available serum sample was tested for antibody binding to the 233 overlapping octapeptides of Sm B/B'. Each patient had antibodies which initially targeted the proline rich, repeated motif, PPPGMRP(G)P (SEQ ID NO:4). With time the response diversified to other regions of Sm B/B' when additional serum samples were available (Arbuckle, M. R., et al., *Scand. J. Immunol.* 50:447-55, 1999).

Sm positive patients from whom a serum sample was available from presentation have also been screened. In addition to the patient presented in FIG. 4, two others who initially have a simplified pattern of octapeptide binding have been found. In all three of these cases, only PPPGMRPP (SEQ ID NO:4) and PPPGMRGP (SEQ ID NO:8) are bound and no other octapeptide are bound. All other anti-Sm positive sera tested bind these octapeptides as well as others. These results are also consistent with PPPGMRPP (SEQ ID NO:4) and PPPGMRGP (SEQ ID NO:8) being the first epitopes of the Sm B/B' autoantigen (Arbuckle, M. R., et al., *Scan. J. Immunol.* 50:447-55, 1999). This repeated PPPGMRPP (SEQ ID NO:4) motif is an early target in three additional patients tested from whom sera were available from early in their disease. In all of these patients PPPGMRPP (SEQ ID NO:4) is the first autoimmune epitope of the Sm B/B' autoantigen against which one can detect antibody binding. One interpretation of this finding is that PPPGMRPP (SEQ ID NO:4) is the first structure bound in at least some of those lupus patients who have anti-Sm autoantibodies. Most, if not nearly all, sera with anti-Sm have more complex binding when they present to their doctors with the illness. At this point, no anti-Sm precipitin positive lupus patient who does not have antibodies to PPPGMRPP (SEQ ID NO:4) is known.

Antibodies directed against PPPGMRPP (SEQ ID NO:4) are a significant portion of the anti-Sm response in some patient sera. Five patient sera have been absorbed over columns composed of PPPGMRPP (SEQ ID NO:4). Four of these sera had anti-Sm and anti-nRNP precipitins and one had an anti-nRNP precipitin without anti-Sm; all five had anti-Ro autoantibodies which were above the normal range. The PPPGMRPP (SEQ ID NO:4) absorption removed 13 to 39% of the patient anti-Sm/nRNP response. These same column absorptions removed less than 10% of the anti-Ro reactivity and over 95% of the anti-PPPGMRPP (SEQ ID NO:4) response. (The proportion of the anti-Sm/nNRP activity absorbed varies with the number of the other octapeptides from Sm B/B' and D proteins bound by immune serum being tested.)

Rabbits Immunized with PPPGMRPP (SEQ ID NO:4) Developed Antibody Beyond the Peptide of Immunization which Bound to Many Other Octapeptides in the Spliceosome, Antinuclear Autoantibodies, Anti-Double Stranded DNA Autoantibodies and Clinical Features that Suggests the Illness Known in Man as Systemic Lupus Erythematosus Rabbits were immunized with PPPGMRPP (SEQ ID NO:4) on a MAP™ backbone (referred to as PPPGMRPP-MAP™ (SEQ ID NO:4) where the trademark refers only to the MAP™). These animals developed antibody beyond the peptide of immunization which bound to many other octapeptides in the spliceosome. These rabbits usually developed anti-PPPGMRPP (SEQ ID NO:4) antibodies along with anti-Sm and anti-nRNP autoantibodies, anti-nuclear autoantibodies, anti-double stranded DNA autoantibodies and clinical features that suggests the illness known in man as systemic lupus erythematosus. These rabbits variably had seizures, thrombocytopenia, proteinuria, renal insufficiency, cellular casts in the urine, hypoalbuminemia and alopecia (James, J. A. et al. *J. Exp. Med.* 181:453-461 (1995)). This has led to a new model of autoimmunity and suggests that a vigorous immune response against this one sequence, PPPGMRPP (SEQ ID NO:4), is sufficient to induce a specific autoimmune disease in some strains of animals.

PPPGRRP (SEQ ID NO:1) from the Epstein-Barr virus Nuclear Antigen-1 was found when the sequence was searched for sequences similar to PPPGMRPP (SEQ ID NO:4). To preliminarily test whether it was possible for this sequence to induce spliceosomal autoimmunity, two rabbits were immunized with PPPGRRP-MAP™ (SEQ ID NO:1) following the protocol previously used with PPPGMRPP-MAP™ (SEQ ID NO:4). One of the two rabbits developed not only anti-PPPGMRPP (SEQ ID NO:4) antibodies, but also anti-spliceosomal autoantibodies and had B cell epitope spreading to regions of B/B' and D, as evidenced by antibody binding to other octapeptides (FIGS. 5 and 6).

If a structure from a virus could induce anti-spliceosomal autoantibodies when immunized in an animal, then this is evidence that this structure and the virus is important in the induction of the autoimmune disease associated with anti-spliceosomal autoantibodies, systemic lupus erythematosus.

These data suggest a sequence of events, as follows: infection with Epstein-Barr virus, development of anti-PPPGRRP (SEQ ID NO:1) antibodies, development of surface immunoglobulin (and secreted antibody) binding both PPPGRRP (SEQ ID NO:1) and PPPGMRPP (SEQ ID NO:4) (the first evidence of autoimmunity), antigen processing of the spliceosome bound by surface immunoglobulin (or soluble antibody) and presentation of the spliceosomal peptides, B cell epitope spreading (and perhaps T cell epitope spreading) and clinical features of lupus. Epstein-Barr virus infected cells are believed to encourage this sequence of events at a number of steps. By substituting another antigen for PPPGRRP (SEQ ID NO:1) and another autoantigen for PPPGMRPP, (SEQ ID NO:4) this mechanism may generate lupus or another autoimmune disorder by following the same general sequence of events.

Genetic Linkages in Mice to Development of Lupus-Like Autoimmunity after Immunization with PPPGMRPP-MAP™ (SEQ ID NO:4)

Experiments in mice have shown that there are some strains which develop lupus-like autoimmunity after immunization with PPPGMRPP-MAP™ (SEQ ID NO:4) and some that do not (J. A. James et al. *Arthritis Rheum.* 38:S226 (1995)).

Briefly, thirteen inbred strains of mice were immunized with PPPGMRPP (or a negative control). Of these strains, five were strong responders to the peptide of immunization, mounted a diversified immune response to the spliceosomal proteins, produced autoantibodies which bound whole autoantigen and developed anti-dsDNA autoantibodies. Several of these strains also developed thrombocytopenia and evidence of renal insufficiency. In addition, regions recognized as antigenic in these strains are also antigenic in other animal models of peptide induced lupus and human disease. The other strains develop antibodies to the peptide of immunization but do not mount a diversified response or develop evidence of clinical disease. Select responder strains also develop anti-dsDNA and positive ANAs, while non-responders do not. One responder strain, AKR/J, also has proteinuria and thrombocytopenia (*J. Immunol.*, 160: 502-508, 1998).

In addition, a recombinant inbred set of mice have been analyzed for peptide induced lupus autoimmunity to assess the role of specific genes in this disorder. Briefly, data from the AKXL recombinant strains strongly suggest that some strains develop peptide induced lupus autoimmunity while others do not. For the fifteen AKXL RI strains, the anti-PPPGMRPP, anti-nRNP, binding to other peptides of Sm B/B and Sm D, ANAs and anti-dsDNAs have been determined. Based upon these data, strains were established to be responders or non-responders. Responders were designated A (as the AKR-like) phenotype while non-responders were called L for the L/J parental strain). These designations have been used to generate the strain distribution pattern for this peptide induced model of lupus autoimmunity. Two analyses were performed using MapManager. The most impressive finding is this Strain Distribution Pattern (SDP) was located only on mouse chromosome 4 between markers D4Mit2 and Cd72 (requiring only one crossover). No other option was found by MapManager. Again, using MapManager, only one locus was linked at a level of confidence of 99.99%, at marker Cd72. At less stringent conditions the only other linked loci were D4Mit2 and Ras 12-7, the flanking markers of Cd72. No linkage was found with H-2 regions or other areas of the mouse genome. The striking association of Cd72 with peptide induced lupus autoimmunity and epitope spreading is large. As a polymorphic cell surface antigen found on B cells and some macrophages which is thought to play a role in B and T cell interactions, Cd72 makes a very attractive candidate locus.

This preliminary finding of linkage in this murine model of lupus suggests that the difference between the two parent strains of a recombinant inbred set of mice which determines the observable B cell epitope spreading and autoimmunity may be found at a single gene locus. This region of murine chromosome 4 does not contain immunoglobulin genes, T cell receptor genes, nor the histocompatibility genes which are highly variable polymorphic genes which determine so many other features of the immune response. The gene for CD72 is found here which may be important. Once the gene responsible for the observed effect is identified, then one skilled in the art can provide compositions for diagnosis, prevention and treatment of autoimmune disease. Beyond this specific example, it is expected that other genes and gene products will be shown to be important and analogous compositions will be obvious to one skilled in the art.

The host experiences changes after Epstein-Barr virus infection beyond the generation of an immune response. Gene expression and molecular machinery in infected cells is altered by the virus. These changes can be detected by those skilled in the art and used as diagnostics, as well as in the screening and development of therapeutics which are particularly important for individuals affected with or at risk of becoming affected with autoimmune disease.

EXAMPLE 2

Association of Seroconversion Against Epstein-Barr Virus and an Autoimmune Disease Sera from lupus patients compared with controls were first tested for seroconversion against Epstein-Barr virus. There were a number of important considerations in designing these experiments. First, the older and more traditional assays for Epstein-Barr seroconversion were insufficiently specific. These assays are especially unreliable when applied to sera from lupus patients. Antinuclear autoantibodies in lupus sera often interfere with the test for Epstein-Barr seroconversion when an Epstein-Barr virus-infected cell line is used for the test resulting in both a positive test result for Epstein-Barr virus and for antinuclear antibodies involving the nuclear fluorescence of the cell line. Also, the infected cell line test for Epstein-Barr virus is often not positive in people known to have been infected with Epstein-Barr virus. Others have used such assays in patients with systemic lupus erythematosus with disappointing results (Tsai, Y. et al. *Int. Arch. Allergy Immunol.* 106:235-240 (1995)).

Second, in the United States as many as 95% of normal adults are infected with and have evidence of seroconversion against Epstein-Barr virus (Evans, A. S. and Niederman, J. C.: Epstein-Barr virus. In Viral Infections in Humans, 3rd ed. Evans, A. S. ed. pp 265-292 (Plenum, New York City 1989)). To detect a difference in adults above the 95% expected baseline of Epstein-Barr virus infection with confidence would require an unreasonably large number of patients and controls. On the other hand, in the United States, most people contract Epstein-Barr virus before the age of 20 years. Epstein-Barr virus causes infectious mononucleosis, also known as the "kissing disease". Controls who are children and adolescents will have a lower rate of infection than individuals who are older. By using younger patients and controls, it was thought that one might be able to collect a group of controls where the rate of Epstein-Barr virus seroconversion is less, perhaps less than 75%, thereby providing a sufficient increase in statistical power to enable this question to be addressed with the resources available.

The use of children and adolescents has nothing to do with anything unique or different about lupus in childhood or adolescence compared with the disease in adults. Rather, the younger cases represent the population in which the hypothesis of a relationship between Epstein-Barr virus infection and autoimmune disease can be most efficiently tested.

The most reliable test for seroconversion is against the Viral Capsid Antigen of Epstein-Barr virus. Solid phase assays are available for antibodies against this surface protein. The purification methods may include other proteins and antigens from Epstein-Barr virus, but as long as a substantial proportion of the preparation is composed of this surface antigen of Epstein-Barr virus, then the assay should be sensitive for an immune response directed against Epstein-Barr virus. The procedure used to isolate the antigen used in the commercial ELISA (enzyme-linked immunosorbent assay) kits has been described in detail (Qualtiere, L. F. and Pearson, G. R. *Virology* 102:360-369 (1980)). Antibodies binding to the Epstein-Barr virus surface protein are thought to occur in virtually everyone who is infected with Epstein-Barr virus. An assay for antibodies binding to the Epstein-Barr virus Viral Capsid Antigen (EBV-VCA) is marketed by only two manufacturers in the United States. The assay first used was manufactured by Clark Laboratories, Inc. (Jamestown, N.Y.). This firm was recently acquired by Wampole Laboratories, a division of Carter-Wallace, Inc. (Cranbury, N.J.) who has continued to provide the same viral assays. The manufacturer's instructions were followed in measuring the anti-VCA Epstein-Barr virus IgG antibodies in lupus patients and their controls, all of whom tested are under 20 years old.

Initially, a cohort of 59 SLE patients between the ages of 8 and 19 from the Oklahoma area, as well as a group of 95 race, gender and age (within two years) matched controls were collected. To control for geographical variation, sera was obtained from Dr. Thomas Lehman for a cohort of patients and sibling controls from the San Diego area. Of these two groups of patients, 116 of 117 patients had evidence of previous exposure to EBV. Only 107 of 153 controls had been previously infected. The association of lupus with Epstein-Barr virus seroconversion is astonishing with an odds ratio of 49.9 and p=0.00000000000421 (Table 1) (*J. Clin. Invest.* 100:3019-26, 1997).

These findings have recently been confirmed and published in a third cohort of young lupus patients and matched controls (Harley, et al. *Arthritis Rheum.* 42:1782-83, 1999).

TABLE 1

Seroconversion frequencies in pediatric lupus and controls for IgG binding to Epstein Barr virus viral capsid antigen (EBV-VCA).
Anti-Epstein-Barr virus Viral Capsid Antigen IgG (# seroconverted (total tested))

| Oklahoma cases and controls | |
|---|---|
| Lupus cases | 59 (59) |
| Controls | 64 (95) |
| San Diego and New York City cases and controls | |
| Lupus cases | 57 (58) |
| Controls | 43 (58) |
| Combined data from lupus cases and controls | |
| Lupus cases | 116 (117) |
| Controls | 107 (153) |
| Odds ratio | 49.9 |
| $\chi^2$ | 31.6 |
| p | <0.00000000000421 |

Odds ratios were calculated from the contingency tables. A $\chi^2$ test was used to assess significance. The assays for all viral antigens were obtained from Clark Laboratories (Jamestown, N.Y.) now a division of Wampole Laboratories (Cranberry, N.J.) and were performed according to the instructions provided by the manufacturer. The surface antigen is partially purified for the anti-Epstein-Barr virus Viral Capsid Antigen antibody assay (Qualtiere, L. F. and Pearson, G. R. *Virology* 102:360-369 (1980)).

The quantitative level of binding to the Epstein-Barr virus Viral Capsid Antigen (as measured relative to the standardized calibrator and as recommended by the manufacturer) also show substantial quantitative differences between lupus cases and controls (Table 2).

TABLE 2

Binding of IgG in sera from pediatric lupus patients and their controls to the Viral Capsid Antigen from Epstein Barr virus (EBV).
Epstein-Barr virus Viral Capsid Antigen (International Standardized Ratios (ISRs)

| Lupus cases (n = 103) (ISRs) | 4.368 |
|---|---|
| Controls (n = 134) (ISRs) | 2.087 |
| t-test | 14.82 |
| probability (p value) | <<0.001 |

Assay is performed as presented in Table 1. Data are presented as International Standardized Ratios (ISRs) which are calculated as described by the manufacturer. The average binding of each tested serum is divided by the product of the calibrator and a lot-specific factor. This allows for standardization across assays. Values <0.9 are considered negative and values >1.1 are considered positive. Values between 0.9 and 1.1 are equivocal and are either re-tested or are assigned to the not positive or negative group. (No patient serum then tested had a result in this equivocal range.)

If the suspected relationship between systemic lupus erythematosus held only for the lupus patients who were anti-Sm positive, then the proportion of lupus patients who had developed the anti-Epstein-Barr virus capsid antigen antibody would be increased over controls only modestly, since the proportion of lupus patients with anti-Sm in their sera rarely exceeds 30%. The remaining lupus patients would have been expected to have the normal control frequency of Epstein-Barr virus seroconversion.

Patients with lupus have such different clinical manifestations from patient to patient, that many investigators suspect that there are many different causes of this disease. Any given particular etiology causing lupus would then be expected to account for only a proportion of the cases. For example, assume that lupus, as observed in the clinics, happens to have two different origins, one from a virus such as Epstein-Barr virus and another from the intrinsic genetic program of some patients. Further assume that the Epstein-Barr virus only accounts for the individual patients who have anti-Sm or anti-nRNP autoantibodies and that this is half of the lupus patients (which is approximately true). Under this scenario, one would expect to see a statistical effect of increased Epstein-Barr virus infection in the group of lupus patients, as a whole, when compared to controls, but the effect would be driven by only half of the patients. Consequently, the proportion of lupus patients with evidence of Epstein-Barr virus infection would be raised, from 71% to 85.5%, but not to the 99% level that has been observed. This 99% rate is the level that would be expected if over 95% of the lupus cases in the collection have been caused by Epstein-Barr virus.

The association is consistent with Epstein-Barr virus infection being a necessary condition before this autoimmune disease can develop in nearly all lupus patients. Assuming Epstein-Barr virus accounts for nearly all cases of lupus, as indicated by the data, then this virus is capable of mediating the various autoimmune manifestations found in lupus beyond just the relationship with anti-Sm antigen originally postulated. Autoantigens in lupus patients are generally thought to be found throughout the tissues of the host and not to be restricted to a single tissue. This is true for Sm, nRNP, Ro, La, P, DNA, and RNA, among many other autoantigens in lupus. Some patients may have antibodies binding other autoantigens which are tissue specific, such as thyroglobulin, but these seem to be less important in this disease. Virtually all active lupus patients have a positive antinuclear antibody, suggesting that at least one of the autoantigens bound by patient autoantibody is directed against a cellular constituent shared between tissues.

This mechanism already allows for a large number of autoantigens. If all of these autoimmune manifestations are related to Epstein-Barr virus infection, then it is probable that other autoimmune disorders are related also. Only a change in the location of the antigen in the host would be required to generate another disorder, among other mechanisms, for Epstein-Barr virus to be a necessary, but not sufficient condition for the development of other autoimmune diseases. For example, a similar mechanism could operate for thyroglobulin or thyroid peroxidase, leading to a tissue specific autoimmune disorder, autoimmune thyroid disease. Again Epstein-Barr virus infection would be a requirement before most patients could develop the disease.

Interestingly, autoimmune thyroid disease and lupus sometimes coexist in the same patient. There are those who have suspected that there is a relationship between systemic lupus erythematosus and autoimmune thyroid disease (R. H. Scofield *Clin. Exp. Rheum.* 14:321-330 (1996)). Under these circumstances, Epstein-Barr virus could be fundamental to both disorders. Other features of the environment, virus strain differences, genetics of the host, hormone and cytokine status, recent and remote immune history, and the nature and course of infection of the Epstein-Barr virus in the host, among other variables, probably then determine how the autoimmunity, as a consequence of Epstein-Barr virus infection, finds expression.

EXAMPLE 3

Experiments to Evaluate Trivial and Artifactual Explanations for the Association of Epstein-Barr Virus Serologic Positivity with an Autoimmune Disease Related to the Source of the Test for Anti-Epstein-Barr Viral Capsid Antigen IgG Antibodies.

Perhaps, the association observed is explained by some artefact of the manufacturing process. Since there are two manufacturers who separately prepare the Viral Capsid Antigen and who use somewhat different procedures, a subset of the lupus patients and controls were evaluated using the test manufactured by Gull Laboratories (Salt Lake City, Utah).

The results from the Gull test for Epstein-Barr seropositivity were essentially identical to those obtained with tests manufactured by Clark Laboratories, Inc. Of the 43 patient sera tested, all were positive for Epstein-Barr virus IgG antibodies who were positive by the Clark assay. The one patient without antibodies to Epstein-Barr virus Viral Capsid Antigen by the Clark assay also had no detectable antibodies to Epstein-Barr virus Viral Capsid Antigen by the Gull assay. Of the 47 control sera tested, none were negative that were previously positive and four were positive in the Gull anti-Epstein-Barr virus Viral Capsid Antigen assay that were previously negative.

This experiment established that the results in Example 3 were not explained by lot variation or an unusual property of the preparation used to detect anti-Epstein-Barr virus surface antigen (*J. Clin. Inv.* 100:3019-27, 1997).

EXAMPLE 4

Experiments to Evaluate Trivial and Artifactual Explanations for the Association of Epstein-Barr Virus Serologic Positivity with an Autoimmune Disease Related to Cross-Reactivity of Autoantibodies with Anti-Epstein-Barr Surface Antigen IgG Antibodies.

Next, five of the lupus patients with high levels of anti-Sm autoantibodies were arbitrarily selected. The anti-spliceosomal autoantibodies were absorbed from their sera and their antinuclear antibody titer reevaluated by immunofluorescence, and anti-Sm/nRNP and anti-Ro antibodies by solid phase assay (following previous methods (Gaither, K. K. et al. *J. Clin. Invest.* 79:841-846 (1987); Harley, J. B. et al. *Arthritis Rheum.* 29:196-206 (1986)), and anti-Epstein-Barr virus Viral Capsid Antigen IgG antibodies.

The spliceosomal antigen preparation is affinity purified from bovine tissue and contains both the Sm and nRNP specificities and, hence, is referred to as Sm/nRNP. This is the same preparation discussed herein for solid phase assays against Sm/nRNP. The previous method for the solid phase anti-Sm/nRNP assay (Gaither, K. K. et al. *J. Clin. Invest.* 79:841-846 (1987); Harley, J. B. et al. *Arthritis Rheum.* 29:196-206 (1986)) was altered by omitting inhibition with purified Sm/nRNP antigen. The same alteration was made in the anti-Ro assay.

These data show that the anti-Sm was reduced by at least 90% in each serum, as expected. In addition, the antinuclear antibodies were reduced by an average of 97%. Meanwhile, neither the anti-Ro nor the anti-Epstein-Barr virus surface antigen IgG antibodies were substantially reduced. The anti-Epstein-Barr virus surface antigen IgG antibodies were reduced by an average of 8%.

These data show that neither anti-Ro nor anti-Epstein-Barr virus Viral Capsid Antigen IgG cross-reacts to any significant extent with the anti-Sm. If they had, then these antibodies would also have been removed by the absorption. In addition, the reduction of the antinuclear antibodies in the absorbed sera by 97% suggests that the anti-Sm/nRNP is the major autoantigen in these lupus patients (*J. Clin. Invest.* 100:3019-27, 1997).

EXAMPLE 5

Experiments to Evaluate Trivial and Artifactual Explanations for the Association of Epstein-Barr Virus Serologic Positivity with an Autoimmune Disease Related a General Polyclonality of Autoantibodies in Lupus Sera.

It was possible that lupus sera may nonspecifically bind to any viral antigen. To test this possibility, the same patient and control sera were evaluated for antibodies against four other Herpes viruses: Cytomegalovirus; Herpes simplex, type 1; Herpes simplex, Type 2; and Varicella zoster (Table 3) (*J. Clin. Invest.* 100:3019-27, 1997).

TABLE 3

Seroconversion frequencies in pediatric lupus and controls for IgG binding to cytomegalovirus antigen (CMV), Herpes simplex type 1 antigen (HSV-1), Herpes simplex virus type 2 antigen (HSV-2), and varicella zoster virus (VZV) antigens.

|  | CMV | HSV-1 | HSV-2 | VZV |
|---|---|---|---|---|
| Oklahoma |  |  |  |  |
| Lupus cases | 24 (59) | 39 (59) | 27 (59) | 56 (59) |
| Controls | 28 (95) | 43 (96) | 28 (96) | 87 (96) |
| San Diego and New York City |  |  |  |  |
| Lupus cases | 18 (58) | 33 (58) | 32 (58) | 46 (58) |
| Controls | 12 (57) | 31 (57) | 23 (57) | 45 (57) |
| All |  |  |  |  |
| Lupus cases | 42 (117) | 72 (117) | 59 (117) | 102 (117) |
| Controls | 40 (152) | 74 (153) | 51 (153) | 132 (153) |
| Odds ratio | 1.57 | 1.71 | 2.03 | 1.08 |
| CI-95% | 0.93, 2.65 | 1.05, 2.79 | 1.24, 334 | 0.53, 224 |
| Probability | 0.11 | 0.036 | 0.0059 | 0.86 |

The odds ratios were calculated from the contigency tables. The assays for all viral antigens were obtained from Clark Laboratories (Jamestown, N.Y.) now a division of Wampole Laboratories (Cranberry, N.J.) and were performed according to the instructions provided by the manufacturer. Whole inactivated virus is used for the CMV, HSV-1, HSV-2 and VZV antibody assays.

There is a small and significant difference between the cases and controls for IgG autoantibodies against herpes simplex, Types 1 and 2, but this difference is only found in the Oklahoma group (Table 3). There is no consistent difference (at the level of p<0.05) between the controls and the lupus patients for the frequency of seroconversion against any of the viruses tested except for Epstein-Barr virus. Its inconsistency is typical of the results of other assays for seroconversion rates in lupus. Of these, only the difference between cases and controls for antibodies against Herpes Simplex virus Type 2 is significant across the entire collection, odds ratio is 2.07 ($X^2$=7.39, p=0.006). The low, but significant, odds ratio, suggests that the contribution of this virus is likely to be small (*J. Clin. Inv.* 100:3019-27, 1997). This initial observation of association with HSV-2, however, has not held up in subsequent studies (*Arthritis Rheum.* 42:1782-83, 1999). Some of the social behaviors that increase the risk of infection with Epstein-Barr virus could also secondarily also increase the risk of contracting Herpes Simplex virus, Type 2. In addition, stepwise logistic regression shows that no difference between cases and controls is present once the Epstein-Barr Virus effect is incorporated into the model (*J. Clin. Inv.* 100:3019-27, 1997).

The modestly, and usually insignificantly, increased odds ratios for the seroprevalence of cytomegalovirus and Herpes simplex Types 1 and 2 in lupus patients compared to controls may reflect the increased levels of binding of antibodies found in other studies (Hollinger, F. B. et al. *Bact. Proc.* 131:174 (1970); Phillips, P. E. and Christian, C. L. *Science* 168:982-4 (1970); Hurd, E. R. et al. *Arthritis Rheum.* 13:724-33 (1970)).

In conclusion, these control assays do not support the position that the difference in the seroconversion rate between lupus patients and their collected controls is the result of a nonspecific binding to viral antigens.

EXAMPLE 6

Experiments to Evaluate Trivial and Artifactual Explanations for the Association of Epstein-Barr Virus Serologic Positivity with an Autoimmune Disease Related to Hypergammaglobulinemia in the Sera of Patients with Autoimmune Disease.

To determine whether hypergammaglobulinemia might explain the differences observed, the IgG level in 32 of the lupus patients was assayed and compared this with the level found in 25 controls. No significant difference was found. In addition, no correlation was found between the IgG level and positive Epstein-Barr virus Viral Capsid Antigen assays. Therefore, an increased level of IgG binding non-specifically to the Epstein-Barr virus Viral Capsid Antigen cannot be an explanation for the findings.

EXAMPLE 7

Demonstration of an Increased Rate of Epstein-Barr Virus Infection in Systemic Lupus Erythematosus An assay for Epstein-Barr virus infection that is not dependent upon serologic analysis removes all of the technical reservations concerning possible artifact or a trivial explanation for the observed association between seroconversion against Epstein-Barr virus Viral Capsid Antigen and an autoimmune disease. To assay for Epstein-Barr virus, independent of serology, a method altered from the DNA based assays already available was developed. The BamHI W repeat nucleic acid sequence of the Epstein-Barr virus genome contains a sequence repeated 11 times that others have used to detect the virus (Saito et al., *J. Exp. Med.* 169:2191-2198, 1989; and Miyashita et al., *Cell* 80:593-601, 1995). These assays were evaluated in an effort to increase specificity. Two mcg DNA specimens were isolated from peripheral blood mononuclear cells. Quantitation of DNA was based both upon optical density measurements at 240 and 260 nm and quantitation of ethidium bromide fluorescence in agarose gel relative to known DNA standards. Where available, six reactions, each containing 2 mcg of mononuclear cell DNA, were evaluated from each subject. The primers and the probe used are given in Table 4.

Antigen ("EBV-VCA") IgG antibodies (as determined by the assay from Clark Laboratories, Inc.) also expanded the predicted 122 base pair DNA fragment which hybridized to the BamHI W probe from the Epstein-Barr viral DNA sequence. Epstein-Barr virus DNA was recovered in three other subjects whose serologic assays were not positive. In one of these subjects the serologic results for Epstein-Barr virus Viral Capsid Antigen IgG was close to the positive range, as determined in comparison to the calibrator sera provided by the manufacturer. One control had evidence of antibodies to EBV-VCA but no evidence of EBV-DNA as determined by the method described herein. Neither anti-Epstein-Barr virus Viral Capsid Antigen IgG antibodies nor Epstein-Barr virus DNA was detected in the other nine control subjects tested.

The new assay has high sensitivity and specificity relative to the serologic analysis. The direct detection of viral DNA,

TABLE 4

Primers and probe used to expand Epstein-Barr virus DNA from the BamHI W repeat.

Forward - 5'-CCAGAGGTAAGTGGACTT-3' (SEQ ID NO:21)
Reverse - 5'-GACCGGTGCCTTCTTAGG-3' (SEQ ID NO:22)
Probe - 5'-AAGACGATTCGGGTTG(TGAGGTGGTGTGGGTCCGTGTGTGATGTGTGTGGGTGGGCAG)*-3' (SEQ ID NO:23)

*The $^{32}$P-dCTP label is incorporated into the portion of the sequence in parentheses.

The polymerase chain reaction for each DNA specimen was run in a final volume of 75 microliter with 50 mM KCl, 10 mM Tris-HCl at pH 8.0, 1.5 mM MgCl$^2$, 0.1% Triton X-100, 0.2 mM each dNTP, 0.5 mM primer, and 2.5 U Taq DNA polymerase. A hot start protocol was followed using Ampliwax PCR Gems™ (Perkin-Elmer, Branchburg, N.J.). The thermocycler was programmed for the following temperature cycles: (95° C. for 2 min, 57° C. for 1 min, 72° C. for 1 min) twice, (94° C. for 1 min, 55° C. for 1 min, 72° C. for 45 sec) 31 times, 72° C. for 5 min.

The primers variably expanded four bands found at approximately 92, 122, ~500, and ~700 base pairs. All four were cloned into the pCRII vector (Invitrogen, San Diego, Calif.) and at least partially sequenced. The 92, ~500, and ~700 base pair products of the polymerase chain reaction are not in the GeneBank database. They are likely to represent human sequence from a region of the genome that has not yet been sequenced.

The 122 base pair product was similarly cloned and sequenced. The sequence obtained exactly matched the sequence predicted from the Epstein-Barr virus BamHI W repeat, which is repeated 11 times and found at positions 14614-14735, 17686-17807, 20758-20879, 23830-23951, 26902-27023, 29974-30095, 33046-33167, 36118-36239, 39190-39311, 42262-42383, and 45334-45455 of the Epstein-Barr DNA sequence (GenBank accession number: v01555). Only this product of the polymerase chain reaction, found at 122 base pairs, hybridized to the radiolabed probe.

The existing assays for Epstein-Barr DNA were modified so that the assay applied would be as sensitive and specific as the serologic assays are for infection in normal individuals. To achieve this goal a total of 12 mcg of mononuclear DNA in six polymerase chain reactions were evaluated. A long probe was used so that very small amounts of expanded BamHI W fragment DNA can be detected.

This assay was used in 50 subjects. Of these, 38 individuals that had positive Epstein-Barr virus Viral Capsid if true, is a more proximal indication of infection than is seroconversion and is probably a better standard for viral infection than is serology.

The detection of Epstein-Barr virus DNA has proven to be sufficiently reliable for application to the evaluation of the frequency of Epstein-Barr virus infection in lupus and their controls. A matched case-control design was followed. Cases of lupus in children and adolescents (<20 years old) had been enrolled into this study as they were encountered along with a sex, age (within two years), and race matched control. To control for socioeconomic factors and likelihood of viral exposure, each case was asked to provide a relative or friend to serve as a control. Relatives were preferred over friends. The inventors selected controls for eight cases who did not provide their own control.

The data were evaluated with the Exact Binomial Test for Matched Data. Of the 32 lupus cases, all 32 had been infected by Epstein-Barr virus as determined by the assay for viral DNA and also had antibodies directed against Epstein-Barr Viral Capsid Antigen. Of the 32 matched controls, 23 had been infected by Epstein-Barr virus as determined by the assay for viral DNA. Of the 23 with viral DNA, 22 had IgG antibodies directed against Epstein-Barr virus Viral Capsid Antigen and one did not. One control had no detectable DNA from the virus by the assay and yet had anti-Epstein-Barr virus Viral Capsid Antigen IgG antibodies.

To evaluate these data from the most conservative perspective, subjects were required to be negative in both assays in order to conclude that a particular subject had not been infected with Epstein-Barr virus. By these criteria nine of the matched pairs were discordant for infection. All nine of these discordant pairs are discordant in the same way, Epstein-Barr virus infection had occurred in the case and not in the control, which is very unlikely to have occurred by chance (p<0.008) (Table 5).

TABLE 5

Matched case-control evaluation of the presence of Epstein-Barr DNA in peripheral blood mononuclear cells from lupus patients (cases) and controls matched for sex, race, and age (+/−2 years).

| Epstein-Barr virus infection | Lupus Cases | Matched Control |
|---|---|---|
| + | + | 23 |
| + | − | 9 |
| − | + | 0 |
| − | − | 0 |

The probability of this distribution occurring by chance is p<0.002 by the Exact Binomial Test for Matched Data. The odds ratio for this distribution cannot be calculated because of the zero cell. If the usual adjustment of 0.5 is made then the odds ratio is estimated to be ≧10.

These results dramatically confirm the serologic data. Collectively, these data, the serologic results and the control experiments establish that there is a virtually complete association of Epstein-Barr virus infection with systemic lupus erythematosus.

EXAMPLE 8

Antibodies Against Epstein-Barr Virus are More Commonly in Adult Lupus Patients as Compared to Controls EBV seroconversion in adult lupus patients compared to controls has also been assessed. Sera from pedigrees collected by the Lupus Multiplex Registry and Repository and other work of Dr. John Harley, from 196 adult lupus patient sera and 392 matched unaffected family members have been tested. When possible, unaffected persons of the same race, sex and age (within 10 years) from the proband's family were used as controls. When no such unaffected members were available, normal from other families multiplex for lupus were used as controls. In the control group seroconversion against EBV is well within the expected infection rate of EBV in adults in the United States (90-95%).

Nearly all adult SLE patients tested to date have seroconverted against EBV. Relative to the controls this result is significant (odds ratio=11.6, $\chi^2$=9.05, p<0.003) (Table 6). Meanwhile, there are no significant differences between patients and controls for the seroconversion rates of CMV, HSV-1, HSV-2, or VZV (Table 7). These data extend the previously observed association of EBV seroconversion (and infection) with lupus in children and teenagers to adult lupus patients (*J. Clin. Inv.* 100:3019-27, 1997; *Arthritis Rheum.* 42:1782-83, 1999).

TABLE 6

Seroconversion against Epstein-Barr virus viral capsid antigen (EBV-VCA) in sera from adult lupus patients and controls is presented. Sera from lupus patients (cases) or their controls were tested for IgG anti-EBV-VCA antibodies and standardized for seroconversion.

| | EBV+ (total tested) | % Positive |
|---|---|---|
| Lupus Patients | 195 (196) | 99.5% |
| Normal Controls | 370 (392) | 94.4% |
| Odds Ratio | 11.6 | |
| 95% C.I. of Odds ratio | 2.35-57.3 | |
| Chi-square | 9.05 | |
| Probability | 0.003 | |

TABLE 7

Seroconversion against cytomegalovirus (CMV), Herpes Simplex Virus Type 1 (HSV-1), Herpes Simplex Virus - Type 2 (HSV-2) and Varicella Zoster virus (VZV) in sera from adult lupus patients and controls.

| | CMV+ | HSV-1 | HSV-2 | VZV |
|---|---|---|---|---|
| Lupus Patients | 130 (196) 66% | 161 (196) 82% | 123 (196) 63% | 193 (195) 99% |
| Normal Controls | 270 (392) 69% | 311 (392) 79% | 217 (392) 55% | 385 (392) 98% |
| Odds ratio (OR) | 0.89 | 1.20 | 1.36 | 1.76 |
| 95% CI of OR | 0.62-1.28 | 0.77-1.9 | 0.96-1.9 | 0.39-8.37 |
| Chi-square | 0.39 | 0.65 | 2.93 | 0.5 |
| Probability | 0.53 | 0.42 | 0.087 | 0.73 |

Sera from lupus patients (cases) or their controls were tested for IgG anti-EBV-VCA antibodies and standardized for seroconversion.

EXAMPLE 9

Antibodies Against Some Epstein-Barr Virus Structures are Associated with the Presence of an Autoimmune Disease, Compositions for Diagnostics Three different cell lines: B95 (marmoset cell line with the most common strain, EBV-1 or -A), Jiyoye cell line (from Burkitt's lymphoma with EBV-2 or -B), and the Ramos cell line which has no EBV infection were obtained. These cell lines are hardy and grow easily. After establishing the lines in our lab, we made cell extracts to screen patient and control sera were made.

15 patient and 13 control sera were screened for binding to these different cells lysates. Anti-EBNA-1 is quite obvious as an approximate 70 kD band. All 15 patient sera, as well as 11 of 13 control sera, strongly bind the EBNA-1 protein in both strains. An EBNA-1 monoclonal antibody which confirms the identify of this band. Many other proteins are bound by patient and control sera. There appears to be more patient sera binding to approximately 90 kD, 58 kD, 50 kD, and 36 kD bands.

Not all of the bands observed are necessarily viral proteins. Many may be cellular autoantigens bound by lupus sera. Indeed, one would expect that most latent proteins will be present, but that many lytic and viral structural proteins are probably so poorly represented that it is just not reasonable to expect that they could be detected by this method. Consequently, sera will be absorbed with a Ramos cell lysate (which has previously been tested in parallel). This absorbed sera will then be tested for reactivity with the B95 and Jiyoye cell lysates.

To more directly test for differences in immune responses to specific EBV antigens, clones of several of the most common EBV proteins have been obtained or generated. Full-length clones of EBNA-1, EBNA-2A and EBNA-2B, have been expressed either in a baculovirus system or a maltose binding fusion protein system. All of these clones have been expressed and purified in significant quantities. These expressed proteins have been used in a few initial experiments to test patient and control reactivity by Western blotting and ELISA. EBNA-1 full length clone antigen reacts quite well in both Western blot and ELISA. Results with patient and control sera with this clone correlate completely with the lysate data presented above.

Three different fragments of EBNA-1 have also been expressed: an amino terminal fragment spanning amino acids 1-79, a middle fragment containing the gly-ala rich region (80-338), and a carboxyl terminal fragment spanning amino acids 339-641. 20 random patient and 20 matched EBV-infected control sera have been screened. Patients show stronger average binding to the N-terminal fragment than matched controls (O.D.=0.451 compared to 0.268). In addition, patients have much higher average binding (O.D.=0.844) to the carboxyl terminus compared to matched EBV-infected controls (O.D.=0.296). On the other hand controls (O.D.=0.779) have higher binding with the gly-ala rich middle segment when compared to patients (O.D.=0.36). All pairwise comparisons of these findings are significant by student's T test ($p<0.001$).

Figure 7:
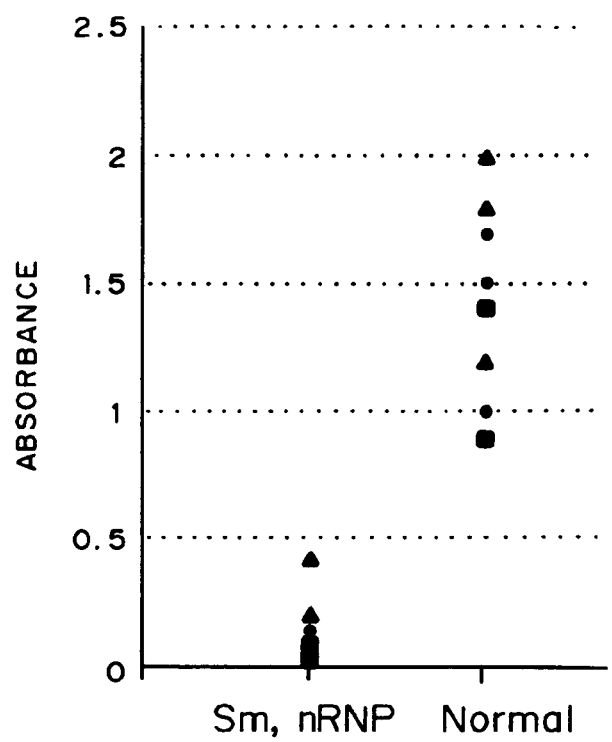
FIG. 7 is a graph of the binding to the peptide GAGAGAGAGAGAGAGAGAGAGAGA (SEQ ID NO:7) from Epstein-Barr virus Nuclear Antigen-1 by lupus sera who all had anti-Sm and anti-nRNP precipitins, as compared to normal control sera.

Four peptide sequences from Epstein-Barr virus were separately evaluated for binding to sera from patients with an autoimmune disease (FIGS. 3 and 7). All are found in the EBNA-1 (Epstein-Barr virus Nuclear Antigen-1) protein. Subjects with an autoimmune disease, systemic lupus erythematosus, tend to have higher levels of antibodies against PPPGRRP (SEQ ID NO:1), GRGRGRGG (SEQ ID NO:2) and RGRGREK (SEQ ID NO:3) than do normal controls. On the other hand the glycine-alanine repeat sequence, GAGAGAGAGAGAGAGAGAGAGA (SEQ ID NO:7), which, after infection by Epstein-Barr virus, is a major epitope in infectious mononucleosis and in normals (Rhodes, G. et al. *J. Exp. Med.* 165:1026-1040 (1987)) tends not to be bound by patients with lupus (FIG. 7).

The overlapping octapeptides were constructed from the sequence of EBNA-1 (Epstein-Barr virus Nuclear Antigen-1) protein and preliminarily evaluated in four lupus patient sera and four controls. One control had no serologic evidence of having been exposed to Epstein-Barr virus, while the other three have anti-Epstein-Barr virus Viral Capsid Antigen IgG antibodies. All four of the patients had anti-Epstein-Barr virus Viral Capsid Antigen IgG antibodies.

The binding to octapeptides from EBNA-1 (Epstein-Barr virus Nuclear Antigen-1) protein shows dramatically different patterns between the Epstein-Barr virus exposed lupus patients and normal controls (FIG. 8). These and other differences could become the basis for diagnostics that predict the risk of an autoimmune disease, that are associated with the presence of an autoimmune disease, and that are associated with particular clinical findings or manifestations. The structures bound by the lupus sera tested are listed in Table 8.

TABLE 8

Octapeptides from Epstein-Barr virus Nuclear Antigen-1 bound by the sera from two patients with systemic lupus erythematosus.

| Octapeptide Number | Sequence | Vaughan |
|---|---|---|
| 27-48 | GGSGPQRRGGDNHGRGRGRGRGRGGGR PGAPG (SEQ ID NO:24) | |
| 58-70 | GGSGSGPRHRDGVRRPQKRP (SEQ ID NO:25) | |
| 72 | RPQKRPSC (SEQ ID NO:26) | |
| 74-83 | QKRPSCIGCKGTHGGTG (SEQ ID NO:27) | |
| 88-90 | GTGAGAGAGG (SEQ ID NO:28) | |
| 376-78 | GGRGRGGSGGRGRGGSGGRGRGGSGGR RGRGRERARGGSRE RARGRGRGRGEKRP RSPS (SEQ ID NO:29) | *E4 |
| 381 | PRSPSSQS (SEQ ID NO:30) | |
| 387-394 | QSSSSGSPPRRPPPGR (SEQ ID NO:31) | |

TABLE 8-continued

Octapeptides from Epstein-Barr virus Nuclear Antigen-1 bound by the sera from two patients with systemic lupus erythematosus.

| Octapeptide Number | Sequence | Vaughan |
|---|---|---|
| 397-424 | RPPPGRRPFFHPVGEADYFEYHQEGGPDG EP (SEQ ID NO:32) | |
| 427 | PDVPPGAI (SEQ ID NO:33) | |
| 431 | PGAIEQGPA (SEQ ID NO:34) | |
| 440-441 | DDPGEGPSTGP (SEQ ID NO:35) | |
| 445-447 | GPSTGPRGQG (SEQ ID NO:36) | |
| 452-453 | GQGDGGRRK (SEQ ID NO:37) | *E14 |
| 455-462 | DGGRRKKGGWFGKHR (SEQ ID NO:38) | *E11 |
| 466-468 | GKHRGQGGSNPK (SEQ ID NO:39) | *E11 |
| 472-475 | GGSNPKFENIA (SEQ ID NO:40) | |
| 491-492 | RSHVERTTD (SEQ ID NO:41) | |
| 496-498 | RTTDEGTWVA (SEQ ID NO:42) | |
| 506 | GVFVYGGS (SEQ ID NO:43) | |
| 508 | FVYGGSKT (SEQ ID NO:44) | |
| 510-513 | YGGSKTSLYNL (SEQ ID NO:45) | |
| 542 | GMAPGPGP (SEQ ID NO:46) | |
| 549 | PQPGPLRE (SEQ ID NO:47) | |
| 591 | CNIRVTVC (SEQ ID NO:48) | |
| 594-596 | RVTVCSFDDG (SEQ ID NO:49) | |
| 607-608 | PPWFPPMVEG (SEQ ID NO:50) | |

These are taken from epitopes with average binding greater than 3 standard deviations about the normal mean (of EBV positive normal controls) and commonly bound by patient sera with an O.D. greater than 0.45 absorbence units. Sequences longer than eight amino acids represent neighboring octapeptides that exceed the 0.450 A U.

Figure 8A:
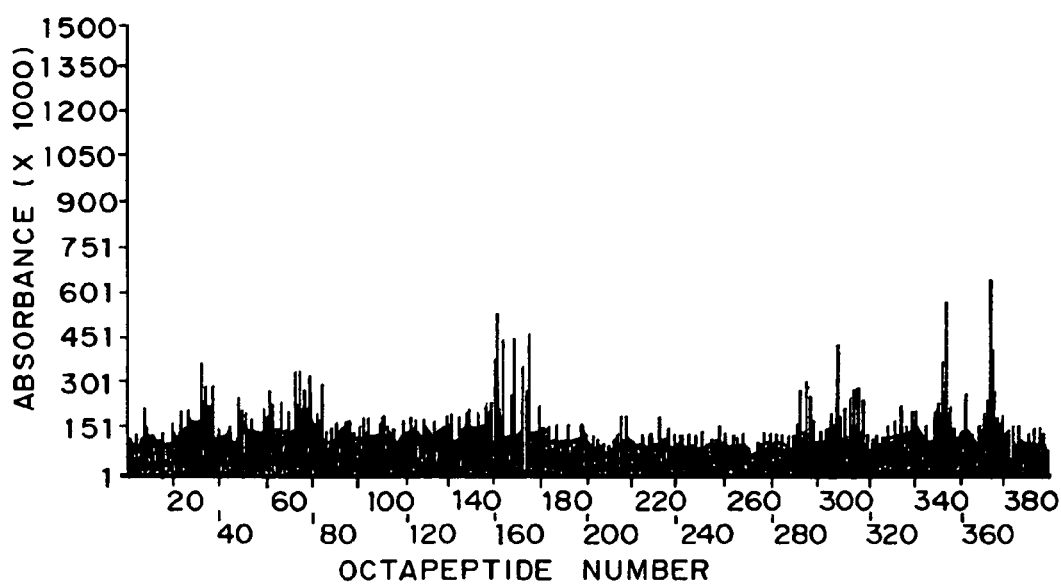
FIGS. 8A-E are graphs of the binding to the overlapping octapeptides from Epstein-Barr virus Nuclear Antigen-1. Each octapeptide overlaps its neighbor by seven amino acids. Most of the glycine-alanine repeat has been omitted to avoid unnecessary redundancy. The binding of three controls are presented in FIGS. 8A, 8B and 8C and that of two lupus sera in FIGS. 8D and 8E.
Figure 8B:
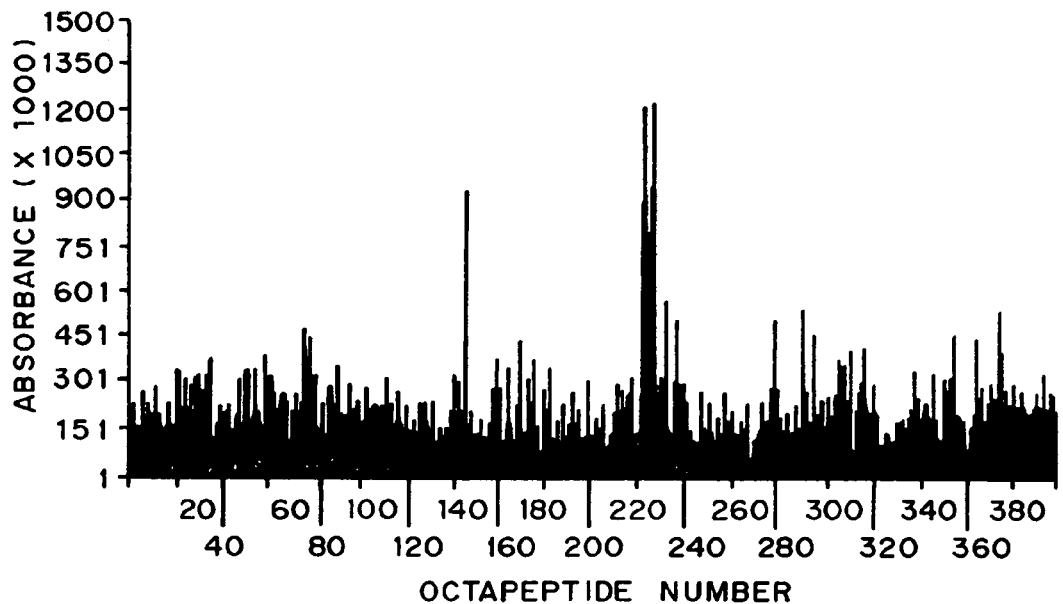
Figure 8C:
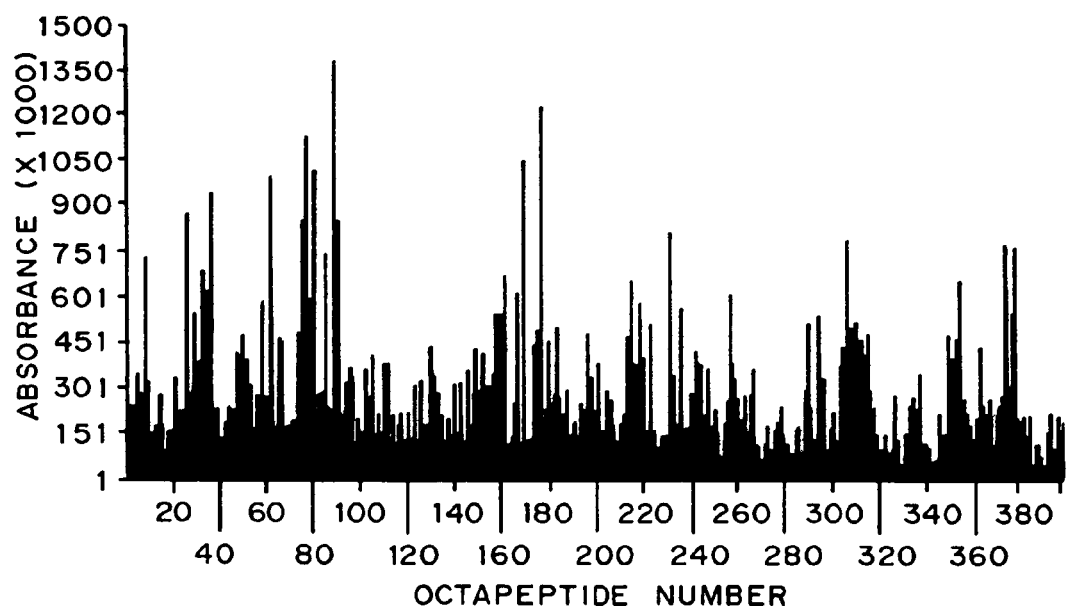
Figure 8D:
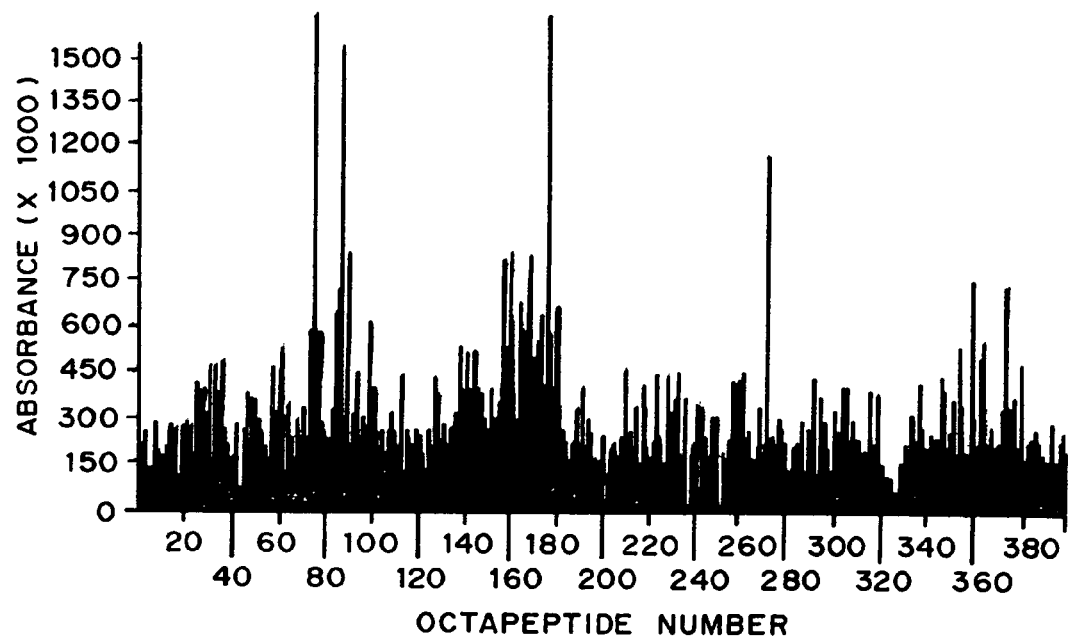
Figure 8E:
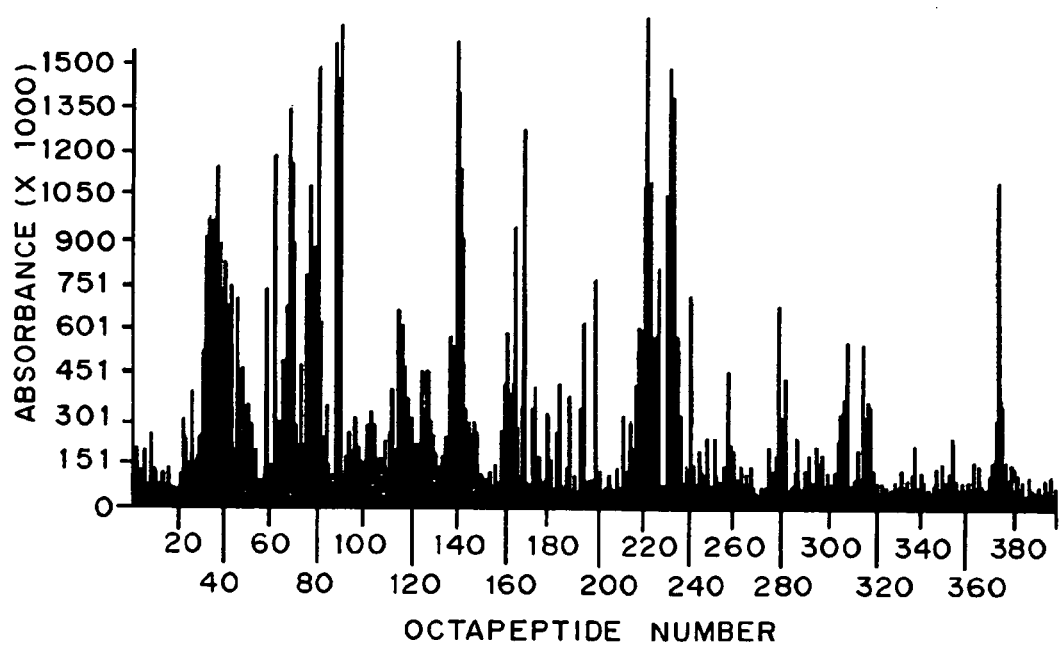

These are taken from the data in FIGS. 8D and 8E as well as additional patients. The peptides presented had average reactivity at least 3 standard deviations above the normal mean. Sequences longer than eight amino acids represent neighboring octapeptides that exceed the 0.450 A.U. threshold. Studies by John Vaughan and colleagues found some peptides of Epstein-Barr virus Nuclear Antigen-1 to be more antigenic in lupus patients than in controls (Petersen, et al, *Arthritis Rheum.* 33: 993-1000 (1990)). The octapeptides which share sequence with the peptides that were used in the Peterson study are identified with the peptide name used in their study (Table 6). Those peptides which they found to be differentially bound by lupus sera, relative to control sera, are identified with an *.

Other differences in the antibody and cellular responses are expected to be important for the purpose of predicting the presence of (diagnosis) or subsequent risk of an autoimmune disease. Those presented above are examples of structures potentially useful for this purpose.

Assuming Epstein-Barr virus causes some autoimmune diseases, then differences in the immune response against this virus have the potential to predict risk of autoimmune disease and to be an aid to diagnosis and management of autoimmune disease.

Other structures defined by the proteins, glycoproteins nucleic acids, etc., will also be useful for this purpose. Such diagnostic tests can be based upon the relative presence of an antibody, cellular proliferation, molecular binding, cytokine production, skin reaction (erythema or induration), cell surface antigen or other measure of activation.

EXAMPLE 10

Antibodies Against some Epstein-Barr Virus Structures as Defined by Peptide Phage Display Experiments are Associated with the Presence of an Autoimmune Disease, Compositions for Diagnostics.

In order to examine the epitopes recognized by anti-Sm sera human autoantibodies specific for the PPPGMRPP (SEQ ID NO:4) peptide were affinity purified. PPPGMRPP (SEQ ID NO:4) constructed on a multiple antigenic peptide (MAP) backbone was coupled to CNBr activated Sepharose™. Each MAP molecule contains eight copies of the PPPGMRPP (SEQ ID NO:4) peptide on a branching polylysine backbone. One ml of sera from a Sm precipitin positive black female lupus patient was passed over the column and extensively washed. Bound antibodies were removed with 3 M guanidine and then dialyzed against 25 mM Tris-HCl pH 8.0. The column affinity purification was repeated using the first round bound material. Purified antibodies were concentrated and quantitated by UV absorption.

In order to identify the peptide epitopes recognized by human anti-PPPGMRPP (SEQ ID NO:4) antibodies we screened a random heptapeptide phage display library from New England Biolabs (Bar Harbor, Mass.) was screened. A heptapeptide library was selected because all $1.28 \times 10^9$ seven amino acid possibilities could be represented (8 a.a.=$2.56 \times 10^{10}$ combinations, 9 a.a.=$5.12 \times 10^{11}$ combinations). In this library each random heptapeptide is expressed at the N-terminus of the pIII minor phage coat protein followed by a Gly-Gly-Gly spacer. There is on average five copies of the pIII protein per phage particle. Theoretically, every combination of seven amino acid sequences could be expressed. However, there are some constraints on this library. The first amino acid of the random peptide can not be a proline. This amino acid will inhibit pIII processing and prevent formation of the phage particle. Also, arginines are under represented in the library. The basic charge on this amino acid has an inhibitory effect on phage secretion. Three hundred ng of antibody was incubated with $2 \times 10^{11}$ phage particles. To enrich for phage particles that recognize the PPPGMRPP (SEQ ID NO:4) epitope 300 ng of purified antibody was incubated with $2 \times 10^{11}$ plaque forming units (pfu). By screening this number of phage clones there is a 99.99% chance of any one peptide being represented.

Antibody-phage complexes were isolated by incubation with protein-A agarose. The samples were spun in a microcentrifuge tube and washed ten times. Bound phage were eluted from the antibody by incubation with 100 mM glycine pH 2.2 followed by neutralization with 1 M Tris-HCl, pH 9.2. The titer of the enriched phage was determined by plating out serial dilutions. The remaining phage stock was amplified by infecting E. coli cells, growing for 5 hours and recovery of the supernatant. The amplified phage stock was titered and a second round of enrichment was performed using $2 \times 10^{11}$ pfu and protein-G agarose instead of protein-A agarose to capture antibody phage complex. This procedure was repeated 2 additional times for a total of 4 enrichments. Protein-A was alternated with protein-G agarose to avoid enriching peptides that bound to these proteins.

During each round of enrichment a small population of phage that nonspecifically bind are also isolated. If only nonspecific binding clones were being isolated, the titer of the enriched phage should remain constant because the same amount of phage particles ($2 \times 10^{11}$ pfu) were used in each enrichment step. The observed increase in phage particles isolated after each round of enrichment and amplification suggests that phage clones that specifically bound the anti-PPPGMRPP (SEQ ID NO:4) antibodies were being enriched.

Following the fourth round of amplification, 70 clones were isolated and sequenced (Table 9). Eleven distinct sequence motifs were identified. Both class I and class II motifs share obvious homology to PPPGMRPP (SEQ ID NO:4) peptide. It is interesting that these motifs correspond to either the N-terminal PPPG sequence or the C-terminal RPP sequence. No motifs were identified that represented the middle GMR sequence. This would suggest that the PPGMRPP may contain two distinct epitopes that are recognized by autoantibodies or that the critical region required for antibody recognition does not include the middle residues.

The current releases of GenBank and the Swiss protein databases were then searched with the peptide sequences obtained from the phage clones. Three of the peptide sequences were identical to proteins contained in these databases. The E. coli ornithine aminotransferase contains a peptide sequence that is identical to the type I peptide ILPPPGY (SEQ ID NO:15). Of the 70 clones sequenced, 9 of them contained sequences homologous to this sequence (two were identical). This peptide also contains the first four amino acids found in the PPPGMRPP (SEQ ID NO:4) epitope. The mouse embryonic development control protein (NEDD1) contains an identical peptide to a type III peptide SPLNVLM (SEQ ID NO:51). Then of the 70 clones, 10 were homologous to this protein with only one being identical.

TABLE 9

Sequence of phage peptides recognized by anti-PPPGMRPP (SEQ ID NO:4) autoantibodies. Each column shows a peptide motif grouped by homology Below each column is the consensus sequence for each motif. (SEQ ID NOs:52-94, 112, and 113)

| Type I | Type II | Type III | Type IV | Type V | Type VI |
|---|---|---|---|---|---|
|  | ARILYPP |  |  |  |  |
|  | ATIYYPN |  |  |  |  |
|  | ALIQRPP | VPLTVLL | QLPLSLV |  |  |
| QLPPPGY | ALIQRPP | VPLTVLL | SPLSTLL | QHFKHPP |  |
| QLPPPGY | ALIQRPP | VPLTVLL | SPLSTLL | QHFKHPP |  |
| ILPSGY | AVIHRPP | VPLTVLL | SPLSTLI | MKLKHPP | KIGFPIL |
| ILPSGY | AVIHRPP | VPLTVLL | SPLTTLL | MKLKHPP | KIGFPIL |
| ILPPPGY | AVINRPP | VPLTVLL | SPLSTLR | MKLKHPP | KIGFPHI |
| ILPPPGY | ASILRPP | VPLTVLL | SPISTLA | MQKVKHP | KIGFPHI |
| VLPPPGY | ASILRPP | VPLTVLL | SPLSSLT | ALKDKLP | KIGFPHI |
| VLAPPGY | ATIFRPS | VPLSVLL | SPHTTLW | ANLDKLP | KIGFPHI |
| TLPPPGR | AQILRPL | SPLNVLM | SPYTILT | AAGIKLP | KIGFPHI |
| Q | I QY |  | I  T | QHF H | IL |
| ILPPPGY | ALILRPP | VPLTVLL | SPLSTLL | AMKLKLPP | KIGFPHI |
| V | V |  |  | D |  |
|  | S |  |  |  |  |

| Type VII | Type VIII | Type IX | Type X | Type XI | MISC. |
|---|---|---|---|---|---|
|  |  |  |  |  | CXLSVLK |
|  |  |  |  |  | MPYMMYQ |
|  |  |  |  |  | AGRLQRT |
|  |  |  |  |  | XXIQRPR |
|  |  |  |  |  | RQPCYAP |
|  |  |  |  |  | QPTYPTP |
|  |  |  |  |  | ATTQXTW |
|  |  |  |  |  | ILPLRG |
| YLTPLQI |  |  |  |  | XXLAPPX |
| KFLAPLQ | IPRPLDY | NHSLPLP | SPPEWLK | NHSLPLP | AKPFKTK |
| AFLPTLQ | IPRPLDY | NHSLPLP | SPPEWLK | NHSLPLP | MPNPVSG |
| SLFPWQR | VPRPLDI | NHSLPLP | SPPSWLK | NHSLPLP | HPHHLPP |
| L |  |  |  |  |  |
| XFLXPLQ | IPRPLDY | NHSLPLP | SPPEWLK | NHSLPLP |  |

Perhaps the most interesting protein identified in the database search was the Epstein-Barr virus major DNA binding protein. As described above, the association of previous exposure to Epstein-Barr virus and lupus in pediatric patients is consistent with the possibility that Epstein-Barr virus is an etiologic agent in the pathogenesis of lupus. This protein contains a peptide sequence that is identical to the type X peptide SPPEWLK (SEQ ID NO:95). The viral protein sequence is followed by a glycine (SPPEWLKG) (SEQ ID NO:96) which is identical to the phage peptide due to the gly-gly-gly spacer separating the random peptide and the pIII protein. Two of three phage clones were identical to this sequence and the other contained a single amino acid substitution. The Epstein-Barr virus major DNA binding protein is a 135 kD protein that is encoded by the BALF2 open reading frame. This protein is required for viral DNA synthesis and is expressed immediately prior to the virus entering the lytic state. Homologues of this protein are found in other herpes viruses such as the cytomegalovirus and herpes simplex virus. However, the peptide sequence bound by anti-PPPGMRPP (SEQ ID NO:4) antibodies is not conserved in any of the other herpes viruses.

A positive control was generated to examine the binding characteristics of these phage clones. Two complementary oligonucleotide primers were synthesized that encoded the amino acids GPPPMRPP (SEQ ID NO:97). The oligonucleotides were then used to replace the random peptide coding sequence from a M13 phage clone. The resulting clone was sequenced to verify that it contained the correct sequence and maintained the proper open reading frame. There are several differences between this peptide and the peptides expressed by the phage clones. First, it is 9 amino acids long, whereas the phage peptides are seven amino acids long. A glycine was also included at the beginning because prolines inhibit cleavage of the phage pIII protein signal sequence. However, these differences should not limit the usefulness of this phage as a positive control.

The binding of anti-PPPGMRPP (SEQ ID NO:4) antibodies to the different types of peptides displayed on the phage was then characterized.

Phage particles were obtained by PEG precipitation. The purified phage were titered by plating out serial dilutions on lawns of E. coli. Initially, Western blots were used to characterize the binding of anti-PPPGMRPP (SEQ ID NO:4) antibodies to the phage peptides. Equivalent amounts of phage particles ($1\times10^{10}$) were separated on a 10% SDS gel and transferred to a nitrocellulose membrane. The results using anti-M13 pIII monoclonal antibody showed that there were approximately equivalent amounts of protein in each lane. When the purified anti-PPPGMRPP (SEQ ID NO:4) antibodies were used, differences in the intensity of the bands were observed. This would suggest that the antibodies have different affinities for the various peptides. It is also possible that denaturing the proteins in SDS caused structural epitopes to be lost. To investigate this possibility a dot blot system where phage were vacuum transferred to nitrocellulose under non-denaturing conditions was used.

Intensities of the dots were measured using the NIH image analysis software package. The wild-type M13 clone had the lowest binding. Six of the clones had an apparent affinity lower than the GPPPGMRPP (SEQ ID NO:10) positive phage clone (FIG. 9 dots, 3, 4, 5, 7, 9 and 10). Two of the clones had approximately equivalent affinity to the positive control (dots 6 and 11) while the remaining two clones showed significantly higher signals (dots 8 and 12). These results were verified by dilution experiments (data not shown).

In order to show specificity, two different inhibition experiments were set up. Aqueous phase inhibition experiments were performed by preincubating anti-PPPGMRPP (SEQ ID NO:4) antibodies with 0, 0.01, 0.1 or 1.0 µg of PPPGMRPP-MAP™. The antibodies were then incubated with 20,000 pfu of the GPPPGMRPP (SEQ ID NO:10) phage. Phage-antibody complexes were isolated using protein-A agarose. The amount of phage bound by the antibodies was determined by titering the bound and unbound material. Using 100 ng of PPPGMRPP-MAP™ blocked approximately 45% of the antibody-phage binding. (100× (1−number of phage bound with 100 ng MAP/number of phage bound without MAP). Similar experiments were then performed using six different phage clones. The PPPGMRPP-MAP™ inhibited binding to all six clones. However, the range of inhibition varied greatly (less than 10% to less than 70%). These results suggest that the antibody-phage binding is due to the sequence of the expressed peptides. However, the affinity of the antibodies for the phage clones varies significantly. The results obtained in these experiments were consistent with the results obtained in the dot blots. Interestingly, in each of these experiments the apparent affinity for the Epstein-Barr virus peptide SPPEWLK (SEQ ID NO:95) is higher than the GPPPMRPP (SEQ ID NO:97)-phage.

EXAMPLE 11

Use of a Vaccine Composition Designed to Induce a Response to Prevent or Treat an Autoimmune Disease Assuming Epstein-Barr virus causes autoimmune disease, then an effective vaccine which induces a protective response against Epstein-Barr virus has the potential to protect the host from the autoimmune disease. This is particularly true if the structure(s) which induce autoimmune disease is(are) altered or removed from the vaccine.

Once infected, this virus is latent and in most, perhaps virtually all, individuals the virus emerges from latency at a low level throughout the remainder of life. The viral infected cells or the immune response required to suppress the virus have the potential to be extremely important in inducing or sustaining the autoimmune disease. Cells latently infected by Epstein-Barr virus may also alter the immune response. Consequently, treatments designed to suppress or eliminate Epstein-Barr virus have the potential to ameliorate the symptoms and tissue damage of the autoimmune disease.

Treatments expected to be useful against autoimmune disease include compositions that suppress the emergence of Epstein-Barr virus from latency. Also, agents for gene therapy directed against Epstein-Barr virus will be useful. Biologicals may also prove useful against Epstein-Barr virus by altering the intracellular environment, making it less hospitable to the virus by directly affecting the virus or by making the immune response against the virus less prone to support an autoimmune disease process.

We claim:

1. Diagnostic reagents for determining whether an individual has or may develop Epstein Barr Virus (EBV)-induced systemic lupus erythematosus (SLE) comprising (a) peptide antigens, which can be used to detect antibodies recognizing the Epstein-Barr virus antigen epitopes including PPPGRRP (SEQ ID NO: 1), GRGRGRGG (SEQ ID NO:2), RGRGREK (SEQ ID NO:3), GGSGSG-PRHRDGVRRPQKRP (SEQ ID NO:25), RPQKRPSC (SEQ ID NO:26), QKRPSCIGCKGTHGGTG (SEQ ID NO:27), GTGAGAGARGRGG (SEQ ID NO:99), SGGR-GRGG (SEQ ID NO: 100), RGGS GGRRGRGR (SEQ ID NO: 101), RARGRGRGRGEKRPRS (SEQ ID NO:102), SSSSGSPPRRPPPGR (SEQ ID NO:103), RPPPGRRPFF-HPVGEADYFEYHQEG (SEQ ID NO:104), PDVPPGAI (SEQ ID NO:33), PGAIEQGPA (SEQ ID NO:34), GPST-GPRG (SEQ ID NO:105), GQGDGGRRK (SEQ ID NO:37) DGGRRKKGGWFGKHR (SEQ ID NO:38), GKHRGQGGSN (SEQ ID NO:106), GQGGSNPK (SEQ ID NO: 107), NPKFENIA (SEQ ID NO: 108), RSHVERTT (SEQ ID NO:109), VFVYGGSKT (SEQ ID NO:110), GSKTSLYNL (SEQ ID NO: 111), GMAPGPGP (SEQ ID NO:46), PQPGPLRE (SEQ ID NO:47), CNIRVTVC (SEQ ID NO:48), RVTVCSFDDG (SEQ ID NO:49), PPWFPP-MVEG (SEQ ID NO:50) and GPQRRGGDNHGRGRGR-GRGRGGGRPG (SEQ ID NO:98); and (b) control samples obtained from individuals with EBV infection but without evidence of SLE.

2. A method for determining that an individual has or may develop EBV-induced SLE comprising:
   a) mixing a test sample with the diagnostic reagents of claim 1,
   b) analyzing antibodies binding to the peptides antigens of the EBV antigen epitopes of claim 1,
   c) comparing the results obtained with control samples from individuals infected with Epstein-Barr virus but without evidence of SLE, and
   d) determining if levels of antibodies binding to each of the peptides antigens in the test sample are at least three standard deviations greater than the normal means of the levels of antibodies binding in the control samples, which indicates the individual has or may develop EBV-induced SLE.

* * * * *

UNITED STATES PATENT AND TRADEMARK OFFICE
CERTIFICATE OF CORRECTION

PATENT NO.        : 7,273,613 B1                                         Page 1 of 1
APPLICATION NO.   : 09/500904
DATED             : September 25, 2007
INVENTOR(S)       : John B. Harley et al.

It is certified that error appears in the above-identified patent and that said Letters Patent is hereby corrected as shown below:

Title Page, Item (63) Related U.S. Application Data, please insert --Continuation-in-part of application No. 08/781,296, filed January 13, 1997.--

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,273,613 B1 |
| APPLICATION NO. | : 09/500904 |
| DATED | : September 25, 2007 |
| INVENTOR(S) | : John B. Harley et al. |

It is certified that error appears in the above-identified patent and that said Letters Patent is hereby corrected as shown below:

Title Page, Item (73) Assignee, please delete "The Board of Regents, The University of Oklahoma, Norman, OK (US);".

Signed and Sealed this

Sixteenth Day of December, 2008

JON W. DUDAS
*Director of the United States Patent and Trademark Office*

SEQUENCE LISTING

<160> NUMBER OF SEQ ID NOS: 113

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:
      Epstein-Barr virus Nuclear Antigen-1 Protein

<400> SEQUENCE: 1

Pro Pro Pro Gly Arg Arg Pro
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:
      Epstein-Barr virus Nuclear Antigen-1 Protein

<400> SEQUENCE: 2

Gly Arg Gly Arg Gly Arg Gly Gly
 1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:
      Epstein-Barr virus Nuclear Antigen-1 Protein

<400> SEQUENCE: 3

Arg Gly Arg Gly Arg Glu Lys
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: autoantigen

<400> SEQUENCE: 4

Pro Pro Pro Gly Met Arg Pro Pro
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: autoantigen

<400> SEQUENCE: 5

Pro Pro Pro Gly Ile Arg Gly Pro
 1               5

<210> SEQ ID NO 6
<211> LENGTH: 8
<212> TYPE: PRT
<220> FEATURE:
<223> OTHER INFORMATION: Description of Artificial Sequence: autoantigen

```
<400> SEQUENCE: 6

Pro Ala Pro Gly Met Arg Pro Pro
  1               5

<210> SEQ ID NO 7
<211> LENGTH: 24
<212> TYPE: PRT
<213> ORGANISM: Artificial Sequence
<220> FEATURE:
<223> OTHER INFORMATION: Description of Artificial Sequence:
      Peptide from Epstein-Barr virus Nuclear Antigen-1

<400> SEQUENCE: 7

Gly Ala Gly Ala Gly Ala Gly Ala Gly Ala Gly Ala Gly Ala Gly Ala
  1               5                  10                  15

Gly Ala Gly Ala Gly Ala Gly Ala
             20

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: autoantigen

<400> SEQUENCE: 8

Pro Pro Pro Gly Met Arg Gly Pro
  1               5

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: a major
      antigenic epitope of Sm D

<400> SEQUENCE: 9

Gly Arg Gly Arg Gly Arg Gly Arg Gly Arg Gly Arg Gly Arg Gly Arg
  1               5                  10                  15

Gly Arg Gly Arg Gly Gly Pro Arg Arg Arg
             20                  25

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Phage

<400> SEQUENCE: 10

Gly Pro Pro Pro Gly Met Arg Pro Pro
  1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 11

Ser Pro Leu Ser Thr Leu Leu
  1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 12

Lys Ile Gly Phe Pro His Ile
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 13

Ile Pro Arg Pro Leu Asp Tyr
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 14

Met Lys Leu Lys His Pro Pro
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 15

Ile Leu Pro Pro Pro Gly Tyr
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 16

Ala Val Ile His Arg Pro Pro
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 17

Ala Leu Ile Gln Arg Pro Pro
 1               5
```

```
<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 18

Val Pro Leu Thr Val Leu Leu
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Phage

<400> SEQUENCE: 19

Ser Pro Pro Glu Leu Lys
  1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Phage

<400> SEQUENCE: 20

Lys Phe Leu Ala Pro Leu Gln
  1               5

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 21
ccagaggtaa gtggactt                                            18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22
gaccggtgcc ttcttagg                                            18

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: Probe

<400> SEQUENCE: 23
aagacgattc gggttgtgag gtggtgtggg tccgtgtgtg atgtgtgtgg gtgggcag    58

<210> SEQ ID NO 24
<211> LENGTH: 32
<212> TYPE: PRT
<213> ORGANISM: Artificial Sequence
```

```
<220> FEATURE:
<223> OTHER INFORMATION: Description of Artificial Sequence: Octapeptide
      from Epstein-Barr virus Nuclear Antigen-1

<400> SEQUENCE: 24

Gly Gly Ser Gly Pro Gln Arg Arg Gly Gly Asp Asn His Gly Arg Gly
 1               5                  10                  15

Arg Gly Arg Gly Arg Gly Arg Gly Gly Arg Pro Gly Ala Pro Gly
            20                  25                  30

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 25

Gly Gly Ser Gly Ser Gly Pro Arg His Arg Asp Gly Val Arg Arg Pro
 1               5                  10                  15

Gln Lys Arg Pro
            20

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 26

Arg Pro Gln Lys Arg Pro Ser Cys
 1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 27

Gln Lys Arg Pro Ser Cys Ile Gly Cys Lys Gly Thr His Gly Gly Thr
 1               5                  10                  15

Gly

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 28

Gly Thr Gly Ala Gly Ala Gly Ala Gly Gly
 1               5                  10

<210> SEQ ID NO 29
<211> LENGTH: 59
<212> TYPE: PRT
<213> ORGANISM: Artificial Sequence
<220> FEATURE:
```

-continued

```
<223> OTHER INFORMATION: Description of Artificial Sequence: Octapeptide
      from Epstein-Barr virus Nuclear Antigen-1

<400> SEQUENCE: 29

Gly Gly Arg Gly Arg Gly Gly Ser Gly Gly Arg Gly Arg Gly Gly Ser
1               5                   10                  15

Gly Gly Arg Gly Arg Gly Gly Ser Gly Gly Arg Arg Gly Arg Gly Arg
                20                  25                  30

Glu Arg Ala Arg Gly Gly Ser Arg Glu Arg Ala Arg Gly Arg Gly Arg
            35                  40                  45

Gly Arg Gly Glu Lys Arg Pro Arg Ser Pro Ser
        50                  55

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 30

Pro Arg Ser Pro Ser Ser Gln Ser
1               5

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 31

Gln Ser Ser Ser Ser Gly Ser Pro Pro Arg Arg Pro Pro Pro Gly Arg
1               5                   10                  15

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 32

Arg Pro Pro Pro Gly Arg Arg Pro Phe Phe His Pro Val Gly Glu Ala
1               5                   10                  15

Asp Tyr Phe Glu Tyr His Gln Glu Gly Gly Pro Asp Gly Glu Pro
                20                  25                  30

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 33

Pro Asp Val Pro Pro Gly Ala Ile
1               5

<210> SEQ ID NO 34
<211> LENGTH: 9
```

```
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 34

Pro Gly Ala Ile Glu Gln Gly Pro Ala
  1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 35

Asp Asp Pro Gly Glu Gly Pro Ser Thr Gly Pro
  1               5                  10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 36

Gly Pro Ser Thr Gly Pro Arg Gly Gln Gly
  1               5                  10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 37

Gly Gln Gly Asp Gly Gly Arg Arg Lys
  1               5

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 38

Asp Gly Gly Arg Arg Lys Lys Gly Gly Trp Phe Gly Lys His Arg
  1               5                  10                  15

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 39

Gly Lys His Arg Gly Gln Gly Gly Ser Asn Pro Lys
```

```
                1               5                    10
```

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 40

Gly Gly Ser Asn Pro Lys Phe Glu Asn Ile Ala
 1               5                   10

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 41

Arg Ser His Val Glu Arg Thr Thr Asp
 1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 42

Arg Thr Thr Asp Glu Gly Thr Trp Val Ala
 1               5                   10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 43

Gly Val Phe Val Tyr Gly Gly Ser
 1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Octapeptide
      from Epstein-Barr virus Nuclear Antigen-1

<400> SEQUENCE: 44

Phe Val Tyr Gly Gly Ser Lys Thr
 1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Octapeptide -continued from Epstein-Barr virus Nuclear Antigen-1

<400> SEQUENCE: 45

Tyr Gly Gly Ser Lys Thr Ser Leu Tyr Asn Leu
 1               5                  10

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Octapeptide
    from Epstein-Barr virus Nuclear Antigen-1

<400> SEQUENCE: 46

Gly Met Ala Pro Gly Pro Gly Pro
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Octapeptide
    from Epstein-Barr virus Nuclear Antigen-1

<400> SEQUENCE: 47

Pro Gln Pro Gly Pro Leu Arg Glu
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Octapeptide
    from Epstein-Barr virus Nuclear Antigen-1

<400> SEQUENCE: 48

Cys Asn Ile Arg Val Thr Val Cys
 1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Octapeptide
    from Epstein-Barr virus Nuclear Antigen-1

<400> SEQUENCE: 49

Arg Val Thr Val Cys Ser Phe Asp Asp Gly
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Octapeptide
    from Epstein-Barr virus Nuclear Antigen-1

<400> SEQUENCE: 50

Pro Pro Trp Phe Pro Pro Met Val Glu Gly
 1               5                  10

<210> SEQ ID NO 51

```
<211> LENGTH: 7
<212> TYPE: PRT
<213> ORGANISM: Artificial Sequence
<220> FEATURE:
<223> OTHER INFORMATION: Description of Artificial Sequence: Type III
      Peptide

<400> SEQUENCE: 51

Ser Pro Leu Asn Val Leu Met
 1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 52

Gln Leu Pro Pro Pro Gly Tyr
 1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 53

Ile Leu Pro Pro Ser Gly Tyr
 1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 54

Val Leu Pro Pro Pro Gly Tyr
 1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 55

Val Leu Ala Pro Pro Gly Tyr
 1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 56
```

```
Thr Leu Pro Pro Pro Gly Arg
 1               5
```

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 57

```
Ala Arg Ile Leu Tyr Pro Pro
 1               5
```

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 58

```
Ala Thr Ile Tyr Tyr Pro Asn
 1               5
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 59

```
Ala Val Ile Asn Arg Pro Pro
 1               5
```

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 60

```
Ala Ser Ile Leu Arg Pro Pro
 1               5
```

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 61

```
Ala Thr Ile Phe Arg Pro Ser
 1               5
```

<210> SEQ ID NO 62
<211> LENGTH: 7
<212> TYPE: PRT
<213> ORGANISM: Artificial Sequence
<220> FEATURE:

```
<223> OTHER INFORMATION: Description of Artificial Sequence: Phage
      Peptide

<400> SEQUENCE: 62

Ala Gln Ile Leu Arg Pro Leu
  1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 63

Gln Leu Pro Leu Ser Leu Val
  1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 64

Ser Pro Leu Ser Thr Leu Ile
  1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 65

Ser Pro Leu Thr Thr Leu Leu
  1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 66

Ser Pro Leu Ser Thr Leu Arg
  1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 67

Ser Pro Ile Ser Thr Leu Ala
  1               5
```

```
<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 68

Ser Pro Leu Ser Ser Leu Thr
  1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 69

Ser Pro His Thr Thr Leu Trp
  1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 70

Ser Pro Tyr Thr Ile Leu Thr
  1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 71

Gln His Phe Lys His Pro Pro
  1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 72

Met Gln Lys Val Lys His Pro
  1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 73
```

```
Ala Leu Lys Asp Lys Leu Pro
 1               5
```

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 74

```
Ala Asn Leu Asp Lys Leu Pro
 1               5
```

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 75

```
Ala Ala Gly Ile Lys Leu Pro
 1               5
```

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 76

```
Lys Ile Gly Phe Pro Ile Leu
 1               5
```

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 77

```
Tyr Leu Thr Pro Leu Gln Ile
 1               5
```

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 78

```
Ala Phe Leu Pro Thr Leu Gln
 1               5
```

<210> SEQ ID NO 79
<211> LENGTH: 7
<212> TYPE: PRT
<213> ORGANISM: Artificial Sequence

```
<220> FEATURE:
<223> OTHER INFORMATION: Description of Artificial Sequence: Phage
      Peptide

<400> SEQUENCE: 79

Ser Leu Phe Pro Trp Gln Arg
 1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Phage
      Peptide
<221> NAME/KEY: VARIANT
<222> LOCATION: (1)
<223> OTHER INFORMATION: XAA at position 1 represents any amino acid
<221> NAME/KEY: VARIANT
<222> LOCATION: (4)
<223> OTHER INFORMATION: XAA at position 4 represents any amino acid

<400> SEQUENCE: 80

Xaa Phe Leu Xaa Pro Leu Gln
 1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 81

Val Pro Arg Pro Leu Asp Ile
 1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 82

Asn His Ser Leu Pro Leu Pro
 1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Phage
      Peptide
<221> NAME/KEY: VARIANT
<222> LOCATION: (2)
<223> OTHER INFORMATION: XAA at position 2 represents any amino acid

<400> SEQUENCE: 83

Cys Xaa Leu Ser Val Leu Lys
 1               5

<210> SEQ ID NO 84
<211> LENGTH: 7
<212> TYPE: PRT
<213> ORGANISM: Artificial Sequence
```

```
<220> FEATURE:
<223> OTHER INFORMATION: Description of Artificial Sequence: Phage
      Peptide

<400> SEQUENCE: 84

Met Pro Tyr Met Met Tyr Gln
  1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 85

Ala Gly Arg Leu Gln Arg Thr
  1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Phage
      Peptide
<221> NAME/KEY: VARIANT
<222> LOCATION: (1)
<223> OTHER INFORMATION: XAA at position 1 represents any amino acid
<221> NAME/KEY: VARIANT
<222> LOCATION: (2)
<223> OTHER INFORMATION: XAA at position 2 represents any amino acid

<400> SEQUENCE: 86

Xaa Xaa Ile Gln Arg Pro Arg
  1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 87

Arg Gln Pro Cys Tyr Ala Pro
  1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 88

Gln Pro Thr Tyr Pro Thr Pro
  1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Phage
      Peptide
```

```
<221> NAME/KEY: VARIANT
<222> LOCATION: (5)
<223> OTHER INFORMATION: Xaa at position 5 represents any amino acid

<400> SEQUENCE: 89

Ala Thr Thr Gln Xaa Thr Trp
 1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 90

Ile Leu Pro Leu Arg Gly
 1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Phage
      Peptide
<221> NAME/KEY: VARIANT
<222> LOCATION: (1)
<223> OTHER INFORMATION: Xaa at position 1 represents any amino acid
<221> NAME/KEY: VARIANT
<222> LOCATION: (2)..
<223> OTHER INFORMATION: Xaa at position 2 represents any amino acid
<221> NAME/KEY: VARIANT
<222> LOCATION: (7)
<223> OTHER INFORMATION: Xaa at position 7 represents any amino acid

<400> SEQUENCE: 91

Xaa Xaa Leu Ala Pro Pro Xaa
 1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 92

Ala Lys Pro Phe Lys Thr Lys
 1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Phage
      Peptide

<400> SEQUENCE: 93

Met Pro Asn Pro Val Ser Gly
 1               5

<210> SEQ ID NO 94
<211> LENGTH: 7
<212> TYPE: PRT
<213> ORGANISM: Artificial Sequence
```

-continued

```
<220> FEATURE:
<223> OTHER INFORMATION: Description of Artificial Sequence: Phage
      peptide

<400> SEQUENCE: 94

His Pro His His Leu Pro Pro
  1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Type X
      Peptide

<400> SEQUENCE: 95

Ser Pro Pro Glu Trp Leu Lys
  1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: type X
      peptide followed by a glycine residue

<400> SEQUENCE: 96

Ser Pro Pro Glu Trp Leu Lys Gly
  1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: positive
      phage clone

<400> SEQUENCE: 97

Gly Pro Pro Pro Met Arg Pro Pro
  1               5

<210> SEQ ID NO 98
<211> LENGTH: 26
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 98

Gly Pro Gln Arg Arg Gly Gly Asp Asn His Gly Arg Gly Arg
  1               5                  10                  15

Gly Arg Gly Arg Gly Gly Gly Arg Pro Gly
              20                  25

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 99
```

-continued

```
Gly Thr Gly Ala Gly Ala Gly Ala Arg Gly Arg Gly Gly
 1               5                  10
```

```
<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 100
```

```
Ser Gly Gly Arg Gly Arg Gly Gly
 1               5
```

```
<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 101
```

```
Arg Gly Gly Ser Gly Gly Arg Arg Gly Arg Gly Arg
 1               5                  10
```

```
<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 102
```

```
Arg Ala Arg Gly Arg Gly Arg Gly Arg Gly Glu Lys Arg Pro Arg Ser
 1               5                  10                  15
```

```
<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 103
```

```
Ser Ser Ser Ser Gly Ser Pro Pro Arg Arg Pro Pro Pro Gly Arg
 1               5                  10                  15
```

```
<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 104
```

```
Arg Pro Pro Pro Gly Arg Arg Pro Phe Phe His Pro Val Gly Glu Ala
 1               5                  10                  15

Asp Tyr Phe Glu Tyr His Gln Glu Gly
                20                  25
```

```
<210> SEQ ID NO 105
<211> LENGTH: 8
```

```
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 105

Gly Pro Ser Thr Gly Pro Arg Gly
  1               5

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 106

Gly Lys His Arg Gly Gln Gly Gly Ser Asn
  1               5                  10

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 107

Gly Gln Gly Gly Ser Asn Pro Lys
  1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 108

Asn Pro Lys Phe Glu Asn Ile Ala
  1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 109

Arg Ser His Val Glu Arg Thr Thr
  1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 110

Val Phe Val Tyr Gly Gly Ser Lys Thr
```

-continued

```
<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Peptide
      from Epstein-Barr virus

<400> SEQUENCE: 111

Gly Ser Lys Thr Ser Leu Tyr Asn Leu
 1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Phage
      Peptides

<400> SEQUENCE: 112

Ala Leu Ile Leu Arg Pro Pro
 1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Phage
      Peptides

<400> SEQUENCE: 113

Ala Met Lys Leu Lys Leu Pro Pro
 1               5
```